United States Patent
Hatcher et al.

(10) Patent No.: US 11,858,897 B2
(45) Date of Patent: Jan. 2, 2024

(54) SUBSTITUTED 6,11-DIHYDRO-5H-BENZO[B]CARBAZOLES AS INHIBITORS OF ALK AND SRPK

(71) Applicant: DANA-FARBER CANCER INSTITUTE, INC., Boston, MA (US)

(72) Inventors: John Hatcher, Marlborough, MA (US); Nathanael S. Gray, Boston, MA (US); Hwangeun Choi, Seoul (KR); Pasi Janne, Needham, MA (US); Tinghu Zhang, Brookline, MA (US)

(73) Assignee: Dana-Farber Cancer Institute, Inc., Boston, MA (US)

(*) Notice: Subject to any disclaimer, the term of this patent is extended or adjusted under 35 U.S.C. 154(b) by 151 days.

(21) Appl. No.: 17/348,394

(22) Filed: Jun. 15, 2021

(65) Prior Publication Data

US 2021/0340102 A1 Nov. 4, 2021

Related U.S. Application Data

(63) Continuation of application No. 16/668,484, filed on Oct. 30, 2019, now Pat. No. 11,066,363, which is a continuation of application No. 15/761,939, filed as application No. PCT/US2016/053245 on Sep. 23, 2016, now Pat. No. 10,508,082.

(60) Provisional application No. 62/222,504, filed on Sep. 23, 2015, provisional application No. 62/356,066, filed on Jun. 29, 2016.

(51) Int. Cl.

| | |
|---|---|
| *A61K 31/403* | (2006.01) |
| *C07D 209/80* | (2006.01) |
| *C07D 401/14* | (2006.01) |
| *C07D 405/14* | (2006.01) |
| *C07D 401/04* | (2006.01) |
| *C07D 403/04* | (2006.01) |
| *C07D 405/04* | (2006.01) |
| *C07D 409/04* | (2006.01) |
| *C07D 413/04* | (2006.01) |
| *A61P 35/00* | (2006.01) |
| *C12N 9/12* | (2006.01) |
| *C12N 9/96* | (2006.01) |

(52) U.S. Cl.
CPC ........... *C07D 209/80* (2013.01); *A61P 35/00* (2018.01); *C07D 401/04* (2013.01); *C07D 401/14* (2013.01); *C07D 403/04* (2013.01); *C07D 405/04* (2013.01); *C07D 405/14* (2013.01); *C07D 409/04* (2013.01); *C07D 413/04* (2013.01); *C12N 9/12* (2013.01); *C12N 9/96* (2013.01); *C12Y 207/11001* (2013.01)

(58) Field of Classification Search
CPC ............................. A61K 31/403; C07D 209/80
USPC .......................................... 514/410; 548/420
See application file for complete search history.

(56) References Cited

FOREIGN PATENT DOCUMENTS

| | | |
|---|---|---|
| CN | 104177342 A | 12/2014 |
| JP | 2012126711 A | 7/2012 |
| WO | 2010/143664 A1 | 12/2010 |
| WO | 2017/053657 A1 | 3/2017 |

OTHER PUBLICATIONS

Gammons, M.V. et al., "Targeting SRPKI to control VEGF-mediated tumour angiogenesis in metastatic melanoma", Br J Cancer, 2014, 111:477-485.
Hackam, et al., JAMA, 2006, 296(14):1731-1732.
Jordan, V. C., "Nature Reviews: Drug Discovery", 2003, 2:205.
Katayama, R. et al., "Two Novel Alk Mutations Mediate Acquired Resistance to the Next-Generation ALK Inhibitor Alectinib", Clin Cancer Res, 2014, 20(22):5686-5696.
Kinoshita, K. et al., "Design and synthesis of a highly selective, orally active and potent anaplastic lymphoma kinase inhibitor (CH5424802)" Bioorg Med Chem, 2012, 20(3):1271-1280.
Sakamoto, H. et al., "CH5424802, a selective ALK inhibitor capable of blocking the resistant gatekeeper mutant", Cancer Cell, 2011, 19(5):679-690.
Vippagunta, et al., "Advanced Drug Delivery Reviews", 2001, 48:18.
Wolff, Manfred E., Ed. Burger's Medicinal Chemistry and Drug Discovery—Fifth Edition, vol. 1: Principles and Practice, New York: John Wiley & Sons, 1994, 975-977.

*Primary Examiner* — Douglas M Willis
(74) *Attorney, Agent, or Firm* — BURNS & LEVINSON, LLP; Daniel W. Clarke, J.D.; Shawn P. Foley

(57) ABSTRACT

The application relates to a compound of Formula (I):

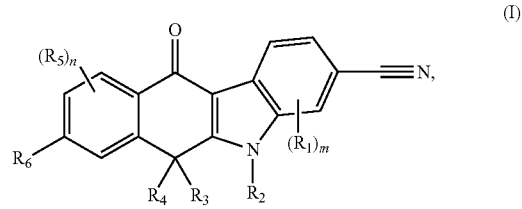

which modulates the activity of ALK or SRPK, a pharmaceutical composition comprising the compound, and a method of treating or preventing a disease in which ALK or SRPK plays a role.

7 Claims, 8 Drawing Sheets

Specification includes a Sequence Listing.

Wild Type

Mutant (G1202R)

Figure 2A
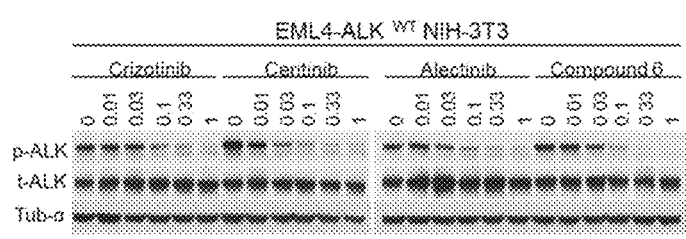
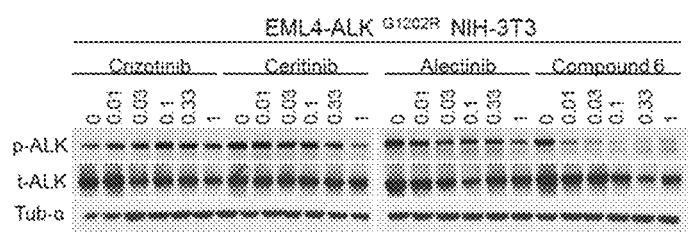
Figure 2B
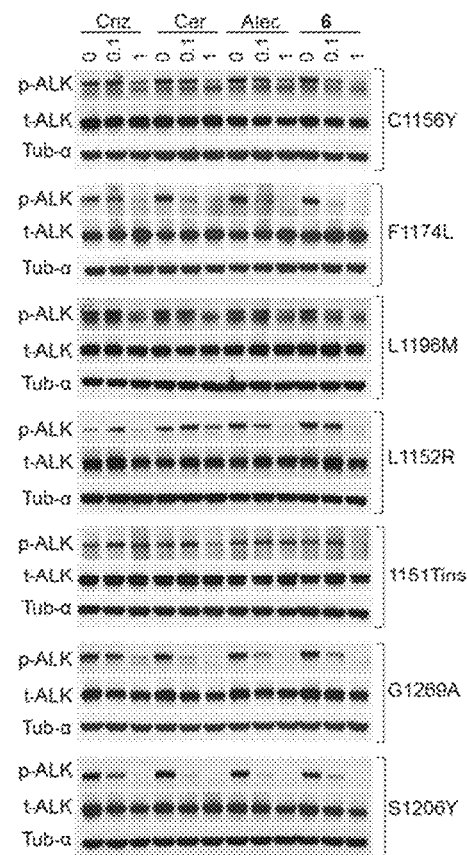

Figure 7

SEQ ID NO: 1

```
  1  MERKVLALQA  RKKRTKAKKD  KAQRKSETQH  RGSAPHSESD  LPEQEEEILG  SDDDEQEDPN
 61  DYCKGGYHLV  KIGDLFNGRY  HVIRKLGWGH  FSTVWLSWDI  QGKKFVAMKV  VKSAEHYTET
121  ALDEIRLLKS  VRNSDPNDPN  REMVVQLLDD  FKISGVNGTH  ICMVFEVLGH  HLLKWIIKSN
181  YQGLPLPCVK  KIIQQVLQGL  DYLHTKCRII  HTDIKPENIL  LSVNEQYIRR  LAAEATEWQR
241  SGAPPPSGSA  VSTAPQPKPA  DKMSKNKKKK  LKKKQKRQAE  LLEKRMQEIE  EMEKESGPGQ
301  KRPNKQEESE  SPVERPLKEN  PPNKMTQEKL  EESSTIGQDQ  TLMERDTEGG  AAEINCNGVI
361  EVINYTQNSN  NETLRHKEDL  HNANDCDVQN  LNQESSFLSS  QNGDSSTSQE  TDSCTPITSE
421  VSDTMVCQSS  STVGQSFSEQ  HISQLQESIR  AEIPCEDEQE  QEHNGPLDNK  GKSTAGNFLV
481  NPLEPKNAEK  LKVKIADLGN  ACWVHKHFTE  DIQTRQYRSL  EVLIGSGYNT  PADIWSTACM
541  AFELATGDYL  FEPHSGEEYT  RDEDHIALII  ELLGKVPRKL  IVAGKYSKEF  FTKKGDLKHI
601  TKLKPWGLFE  VLVEKYEWSQ  EEAAGFTDFL  LPMLELIPEK  RATAAECLRH  PWLNS
```

SUBSTITUTED 6,11-DIHYDRO-5H-BENZO[B]CARBAZOLES AS INHIBITORS OF ALK AND SRPK

RELATED APPLICATIONS

This application is a continuation of U.S. application Ser. No. 16/668,484, now allowed, filed Oct. 30, 2019, which is a continuation of U.S. application Ser. No. 15/761,939, now U.S. Pat. No. 10,508,082, issued Dec. 17, 2019, filed Mar. 21, 2018, which is a U.S. National Phase application, filed under 35 U.S.C. § 371, of International Application No. PCT/US2016/053245, filed Sep. 23, 2016, which claims the benefit of, and priority to, U.S. provisional application Nos. 62/222,504, filed Sep. 23, 2015, and 62/356,066, filed Jun. 29, 2016, the contents of each of which are incorporated herein by reference in their entireties.

GOVERNMENT SUPPORT

This invention was made with government support under grant numbers R01 CA136851 and R01 CA172592 awarded by The National Institutes of Health. The government has certain rights in the invention.

INCORPORATION BY REFERENCE OF SEQUENCE LISTING

The contents of the text file named "52095-656C02US-SL.txt," which was created on Jun. 14, 2021 and is 6.07 KB in size, are hereby incorporated by reference in their entirety.

BACKGROUND

Anaplastic lymphoma kinase (ALK) is a receptor tyrosine kinase in the insulin receptor superfamily. ALK plays an important role in the development of the brain and exerts its effects on specific neurons in the nervous system. Aberrant expression and hyperactivation of ALK due to translocations or point mutations have been shown to be oncogenic in a large variety of cancers, e.g., inflammatory myofibroblastic tumors, diffuse large B cell lymphoma, squamous cell carcinoma, and non-small-cell lung carcinoma. Lung cancers with ALK rearrangements are highly sensitive to ALK tyrosine kinase inhibition, underscoring that such cancers are addicted to ALK kinase activity. ALK is therefore widely recognized as an attractive target for the design and development of diagnostic or therapeutic agents. For example, the ALK inhibitor, Crizotinib was approved by the FDA to treat patients with advanced NSCLC harboring ALK rearrangements. However, despite a high response rate in ALK rearranged NSCLC, most patients develop resistance to Crizotinib after 1 year of treatment. In particular, the central nervous system (CNS) is one of the most common sites of relapse.
Studies of lung cancers harboring ALK rearrangements with acquired resistance to Crizotinib have identified ALK fusion gene amplification and secondary ALK kinase domain mutations. The most frequently identified secondary mutations are L1196M (gatekeeper mutation), G1269A, 1151T-ins, L1152R, C1156Y, G1202R, F1174L, and S1206. Several second generation ALK inhibitors have been developed in an attempt to overcome resistance due to these secondary mutants, however, the G1202R mutant confers resistance to all clinical stage ALK inhibitors. At present, suitable compounds targeting G1202R mutant ALK are not available.

Serine-arginine protein kinases (SRPKs) constitute a relatively novel subfamily of serine-threonine kinases (e.g., SRPK1 and SRPK2) that specifically phosphorylate serine residues residing in serine-arginine/arginine-serine dipeptide motifs. Serine-rich protein kinase-1 (SRPK1) has been identified as a regulator of pro-angiogenic vascular endothelial growth factor (VEGF) splicing by phosphorylating serine-rich splicing factor-1 (SRSF1), which binds to VEGF pre-mRNA. VEGF is alternatively spliced to form a family of multiple isoforms, each having different biological properties and activities. Most cells commonly express isoforms $VEGF_{121}$, $VEGF_{165}$, and $VEGF_{189}$, whereas $VEGF_{145}$ and $VEGF_{206}$ are comparatively rare. The majority of VEGF isoforms contain exons 1-5 and varying portions of exons 6 and 7. Knockdown of SRPK1 potently reduces VEGF mediated angiogenesis in tumors in vivo, and inhibition of SRPK 1 and 2 decreases angiogenesis in vivo. In addition, it is discovered that inhibition of SRPK1 can switch the splicing isoform pattern for VEGF from 165 (pro-angiogenic) to 165b (anti angiogenic).

Age-related macular degeneration (AMD) is the leading cause of blindness in people over 50 years of age. Choroidal neovascularization (CNV) is the abnormal growth of new vessels from the choroid into the retinal pigmented epithelium (RPE), and is thought to lead to visual loss due to the leakage of blood and serous fluid beneath the RPE. VEGF, a key factor in angiogenesis and vascular leakage is up-regulated during the progression of CNV, and has become a promising therapeutic target for the treatment of eye diseases associated with vascularization, such as AMD.

Thus, there is a need for novel and potent small molecule ALK inhibitors, such as inhibitors with activity against the G1202R mutation, as well as small molecule SRPK inhibitors. The present application addresses the need.

SUMMARY

The present application relates to a compound of Formula (I) or (Ia), as defined herein, that is capable of inhibiting ALK activity. The application features methods of treating or preventing a disease in which activated ALK plays a role in a subject in need thereof by administering to the subject a therapeutically effective amount of a compound of Formula (I) or (Ia), or a pharmaceutically acceptable salt, hydrate, solvate, prodrug, stereoisomer, or tautomer thereof, as defined herein.

The present application also relates to a compound of Formula (I) or (Ia), as defined herein, that is capable of inhibiting SRPK (e.g., SRPK1 and/or SRPK2) activity. The application features methods of treating or preventing a disease in which VEGF mediated angiogenesis plays a role in a subject in need thereof by administering to the subject a therapeutically effective amount of a compound of Formula (I) or (Ia), or a pharmaceutically acceptable salt, hydrate, solvate, prodrug, stereoisomer, or tautomer thereof, as defined herein.

A first aspect of the application relates to a compound of Formula (I):

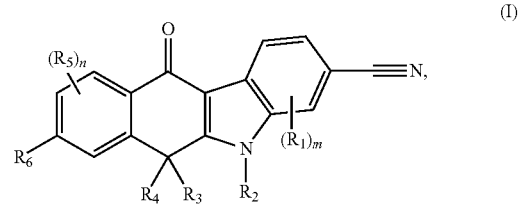

or a pharmaceutically acceptable salt, hydrate, solvate, prodrug, stereoisomer, or tautomer thereof, wherein $R_1$, $R_2$, $R_3$, $R_4$, $R_5$, $R_6$, m, and n are each described herein in detail below.

Another aspect of the present application relates to a pharmaceutical composition comprising a compound of Formula (I), or a pharmaceutically acceptable salt, hydrate, solvate, prodrug, stereoisomer, or tautomer thereof, and a pharmaceutically acceptable carrier.

Another aspect of the present application relates to a method of inhibiting a kinase (e.g., ALK or a mutant ALK (e.g., ALK G1202R), or SRPK (e.g., SRPK1 and/or SRPK2)). The method comprises administering to a subject in need thereof an effective amount of a compound of Formula (I), or a pharmaceutically acceptable salt, hydrate, solvate, prodrug, stereoisomer, or tautomer thereof.

Another aspect of the present application relates to a method of treating or preventing a disease or disorder (e.g., cancer) in which a kinase (e.g., ALK or a mutant ALK (e.g., ALK G1202R), or SRPK (e.g., SRPK1 and/or SRPK2)) plays a role. The method comprises administering to a subject in need thereof an effective amount of a compound that binds to ALK or the mutant ALK (e.g., at the ATP binding site of ALK or of the mutant ALK) or to SRPK (e.g., SRPK1 and/or SRPK2), such as a compound of Formula (I), or a pharmaceutically acceptable salt, hydrate, solvate, prodrug, stereoisomer, or tautomer thereof.

Another aspect of the present application relates to a method of inhibiting anaplastic lymphoma kinase (ALK) or a mutant ALK (e.g., ALK G1202R). The method comprises administering to a subject in need thereof an effective amount of a compound that binds to ALK or the mutant ALK (e.g., at the ATP binding site of ALK or of the mutant ALK), such as a compound of Formula (I), or a pharmaceutically acceptable salt, hydrate, solvate, prodrug, stereoisomer, or tautomer thereof.

Another aspect of the present application relates to a method of treating or preventing a disease or disorder (e.g., cancer) in which ALK or a mutant ALK (e.g., ALK G1202R) plays a role. The method comprises administering to a subject in need thereof an effective amount of a compound that binds to ALK or the mutant ALK (e.g., at the ATP binding site of ALK or of the mutant ALK), such as a compound of Formula (I), or a pharmaceutically acceptable salt, hydrate, solvate, prodrug, stereoisomer, or tautomer thereof.

Another aspect of the present application relates to a method of treating or preventing cancer, wherein the cancer cell comprises activated ALK. The method comprises administering to a subject in need thereof an effective amount of a compound that binds to ALK or a mutant ALK (e.g., ALK G1202R) (e.g., at the ATP binding site of ALK or of the mutant ALK), such as a compound of Formula (I), or a pharmaceutically acceptable salt, hydrate, solvate, prodrug, stereoisomer, or tautomer thereof.

Another aspect of the present application relates to a method of treating or preventing cancer in a subject, wherein the subject is identified as being in need of inhibition of ALK or a mutant ALK (e.g., ALK G1202R) for the treatment or prevention of cancer. The method comprises administering to the subject an effective amount of a compound that binds to ALK or the mutant ALK (e.g., at the ATP binding site of ALK or of the mutant ALK), such as a compound of Formula (I), or a pharmaceutically acceptable salt, hydrate, solvate, prodrug, stereoisomer, or tautomer thereof.

Another aspect of the present application relates to a method of treating or preventing a disease or disorder (e.g., cancer), wherein the disease or disorder is resistant to an ALK targeted therapy, such as a therapy with Alectinib (AF802), Ceritinib (LDK378), Brigatinib (AP26113), Crizotinib (Xalkori), and/or PF-06463922. The method comprises administering to a subject in need thereof an effective amount of a compound that binds to ALK or a mutant ALK (e.g., ALK G1202R) (e.g., at the ATP binding site of ALK or of the mutant ALK), such as a compound of Formula (I) or a compound of Formula (Ia):

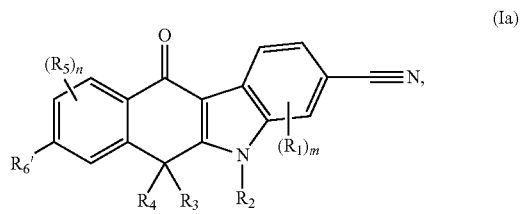

or a pharmaceutically acceptable salt, hydrate, solvate, prodrug, stereoisomer, or tautomer thereof, wherein $R_1$, $R_2$, $R_3$, $R_4$, $R_5$, $R_6'$, m, and n are each described herein in detail below.

Another aspect of the present application relates to a method of treating or preventing cancer, wherein the cancer cell comprises a mutant ALK (e.g., ALK G1202R). The method comprises administering to a subject in need thereof an effective amount of a compound that binds to ALK or the mutant ALK (e.g., at the ATP binding site of ALK or of the mutant ALK), such as a compound of Formula (I) or (Ia), or a pharmaceutically acceptable salt, hydrate, solvate, prodrug, stereoisomer, or tautomer thereof.

Another aspect of the present application relates to a method of inhibiting a mutant ALK (e.g., ALK G1202R). The method comprises administering to a subject in need thereof an effective amount of a compound that binds to ALK or the mutant ALK (e.g., at the ATP binding site of ALK or of the mutant ALK), such as a compound of Formula (Ia), or a pharmaceutically acceptable salt, hydrate, solvate, prodrug, stereoisomer, or tautomer thereof.

Another aspect of the present application relates to a method of treating or preventing a disease or disorder (e.g., cancer) in which a mutant ALK (e.g., ALK G1202R) plays a role. The method comprises administering to a subject in need thereof an effective amount of a compound that binds to ALK or the mutant ALK (e.g., at the ATP binding site of ALK or of the mutant ALK), such as a compound of Formula (Ia), or a pharmaceutically acceptable salt, hydrate, solvate, prodrug, stereoisomer, or tautomer thereof.

Another aspect of the present application relates to a method of treating or preventing cancer, wherein the cancer cell comprises a mutant ALK (e.g., ALK G1202R). The method comprises administering to a subject in need thereof an effective amount of a compound that binds to ALK or the mutant ALK (e.g., at the ATP binding site of ALK or of the mutant ALK), such as a compound of Formula (Ia), or a pharmaceutically acceptable salt, hydrate, solvate, prodrug, stereoisomer, or tautomer thereof.

Another aspect of the present application relates to a method of treating or preventing cancer in a subject, wherein the subject is identified as being in need of inhibition of a mutant ALK (e.g., ALK G1202R) for the treatment or prevention of cancer. The method comprises administering to the subject an effective amount of a compound that binds to ALK or the mutant ALK (e.g., at the ATP binding site of ALK or of the mutant ALK), such as a compound of Formula (Ia), or a pharmaceutically acceptable salt, hydrate, solvate, prodrug, stereoisomer, or tautomer thereof.

Another aspect of the present application relates to a method of inhibiting SRPK (e.g., SRPK1 and/or SRPK2). The method comprises administering to a subject in need thereof an effective amount of a compound of Formula (I) or (Ia), or a pharmaceutically acceptable salt, hydrate, solvate, prodrug, stereoisomer, or tautomer thereof.

Another aspect of the present application relates to a method of regulating (e.g., inhibiting) VEGF mediated angiogenesis. The method comprises administering to a subject in need thereof an effective amount of a compound that inhibits SRPK (e.g., SRPK1 and/or SRPK2), such as a compound of Formula (I) or (Ia), or a pharmaceutically acceptable salt, hydrate, solvate, prodrug, stereoisomer, or tautomer thereof.

Another aspect of the present application relates to a method of treating or preventing a disease or disorder in which VEGF mediated angiogenesis plays a role (e.g., AMD or angiogenesis-dependent cancers). The method comprises administering to a subject in need thereof an effective amount of a compound that inhibits SRPK (e.g., SRPK1 and/or SRPK2), such as a compound of Formula (I) or (Ia), or a pharmaceutically acceptable salt, hydrate, solvate, prodrug, stereoisomer, or tautomer thereof.

Another aspect of the present application relates to a method of treating or preventing AMD. The method comprises administering to a subject in need thereof an effective amount of a compound that inhibits SRPK (e.g., SRPK1 and/or SRPK2), such as a compound of Formula (I) or (Ia), or a pharmaceutically acceptable salt, hydrate, solvate, prodrug, stereoisomer, or tautomer thereof.

Another aspect of the present application relates to a method of treating or preventing AMD in a subject, wherein the subject is identified as being in need of regulation (e.g., inhibition) of VEGF mediated angiogenesis for the treatment or prevention of AMD. The method comprises administering to the subject an effective amount of a compound that inhibits SRPK (e.g., SRPK1 and/or SRPK2), such as a compound of Formula (I) or (Ia), or a pharmaceutically acceptable salt, hydrate, solvate, prodrug, stereoisomer, or tautomer thereof.

Another aspect of the present application relates to a method of treating or preventing an angiogenesis-dependent cancer (e.g., tumorous cancer). The method comprises administering to a subject in need thereof an effective amount of a compound that inhibits SRPK (e.g., SRPK1 and/or SRPK2), such as a compound of Formula (I) or (Ia), or a pharmaceutically acceptable salt, hydrate, solvate, prodrug, stereoisomer, or tautomer thereof.

Another aspect of the present application relates to a method of treating or preventing an angiogenesis-dependent cancer (e.g., tumorous cancer) in a subject, wherein the subject is identified as being in need of regulation (e.g., inhibition) of VEGF mediated angiogenesis for the treatment or prevention of an angiogenesis-dependent cancer. The method comprises administering to a subject in need thereof an effective amount of a compound that inhibits SRPK (e.g., SRPK1 and/or SRPK2), such as a compound of Formula (I) or (Ia), or a pharmaceutically acceptable salt, hydrate, solvate, prodrug, stereoisomer, or tautomer thereof.

Another aspect of the present application relates to a compound of Formula (I), or a pharmaceutically acceptable salt, hydrate, solvate, prodrug, stereoisomer, or tautomer thereof, for inhibiting a kinase (e.g., ALK or a mutant ALK (e.g., ALK G1202R), or SRPK (e.g., SRPK1 and/or SRPK2)).

Another aspect of the present application relates to a compound of Formula (I), or a pharmaceutically acceptable salt, hydrate, solvate, prodrug, stereoisomer, or tautomer thereof, for treating or preventing a disease or disorder (e.g., cancer) in which a kinase (e.g., ALK or a mutant ALK (e.g., ALK G1202R), or SRPK (e.g., SRPK1 and/or SRPK2)) plays a role.

Another aspect of the present application relates to a compound that binds to ALK or a mutant ALK (e.g., ALK G1202R) (e.g., at the ATP binding site of ALK or of the mutant ALK), such as a compound of Formula (I), or a pharmaceutically acceptable salt, hydrate, solvate, prodrug, stereoisomer, or tautomer thereof, for (1) inhibiting ALK or the mutant ALK, (2) treating or preventing a disease or disorder (e.g., cancer) in which ALK or the mutant ALK plays a role, (3) treating or preventing cancer, wherein the cancer cell comprises activated ALK, and/or (4) treating or preventing cancer in a subject identified as being in need of inhibition of ALK or the mutant ALK for the treatment or prevention of cancer.

Another aspect of the present application relates to a compound that binds to ALK or a mutant ALK (e.g., ALK G1202R) (e.g., at the ATP binding site of ALK or of the mutant ALK), such as a compound of Formula (I) or (Ia), or a pharmaceutically acceptable salt, hydrate, solvate, prodrug, stereoisomer, or tautomer thereof, for (1) treating or preventing a disease or disorder (e.g., cancer) resistant to an ALK targeted therapy, such as a therapy with Alectinib (AF802), Ceritinib (LDK378), Brigatinib (AP26113), Crizotinib (Xalkori), and/or PF-06463922, and/or (2) treating or preventing cancer, wherein the cancer cell comprises the mutant ALK.

Another aspect of the present application relates to a compound that binds to ALK or a mutant ALK (e.g., ALK G1202R) (e.g., at the ATP binding site of ALK or of the mutant ALK), such as a compound of Formula (Ia), or a pharmaceutically acceptable salt, hydrate, solvate, prodrug, stereoisomer, or tautomer thereof, for (1) inhibiting the mutant ALK, (2) treating or preventing a disease or disorder (e.g., cancer) in which the ALK mutant plays a role, (3) treating or preventing cancer, wherein the cancer cell comprises the mutant ALK, and/or (4) treating or preventing cancer in a subject identified as being in need of inhibition of the mutant ALK for the treatment or prevention of the cancer.

Another aspect of the present application relates to a compound of Formula (I) or (Ia), or a pharmaceutically acceptable salt, hydrate, solvate, prodrug, stereoisomer, or tautomer thereof, for (1) inhibiting SRPK (e.g., SRPK1 and/or SRPK2), (2) regulating (e.g., inhibiting) VEGF mediated angiogenesis, (3) treating or preventing a disease or disorder in which a VEGF mediated angiogenesis plays a role (e.g., AMD or angiogenesis-dependent cancers), (4) treating or preventing AMD, (5) treating or preventing AMD in a subject identified in need of regulation (e.g., inhibition) of VEGF mediated angiogenesis for the treatment or prevention of AMD, (6) treating or preventing an angiogenesis-dependent cancer (e.g., tumorous cancer), and/or (7) treating or preventing an angiogenesis-dependent cancer (e.g., tumorous cancer) in a subject identified in need of regulation of VEGF mediated angiogenesis for the treatment or prevention of an angiogenesis-dependent cancer.

Another aspect of the present application relates to use of a compound of Formula (I), or a pharmaceutically acceptable salt, hydrate, solvate, prodrug, stereoisomer, or tautomer thereof, in the manufacture of a medicament for inhibiting a kinase (e.g., ALK or a mutant ALK (e.g., ALK G1202R), or SRPK (e.g., SRPK1 and/or SRPK2)).

Another aspect of the present application relates to use of a compound of Formula (I), or a pharmaceutically acceptable salt, hydrate, solvate, prodrug, stereoisomer, or tautomer thereof, in the manufacture of a medicament for treating or preventing a disease or disorder (e.g., cancer) in which a kinase (e.g., ALK or a mutant ALK (e.g., ALK G1202R), or SRPK (e.g., SRPK1 and/or SRPK2)) plays a role.

Another aspect of the present application relates to use of a compound that binds to ALK or a mutant ALK (e.g., ALK G1202R) (e.g., at the ATP binding site of ALK or of the mutant ALK), such as a compound of Formula (I), or a pharmaceutically acceptable salt, hydrate, solvate, prodrug, stereoisomer, or tautomer thereof, in the manufacture of a medicament for (1) inhibiting ALK or the mutant ALK, (2) treating or preventing a disease or disorder (e.g., cancer) in which ALK or the mutant ALK plays a role, (3) treating or preventing cancer, wherein the cancer cell comprises activated ALK, and/or (4) treating or preventing cancer in a subject identified as being in need of inhibition of ALK or the mutant ALK for the treatment or prevention of cancer.

Another aspect of the present application relates to use of a compound that binds to ALK or a mutant ALK (e.g., ALK G1202R) (e.g., at the ATP binding site of ALK or of the mutant ALK), such as a compound of Formula (I) or (Ia), or a pharmaceutically acceptable salt, hydrate, solvate, prodrug, stereoisomer, or tautomer thereof, in the manufacture of a medicament for (1) treating or preventing a disease or disorder (e.g., cancer) resistant to an ALK targeted therapy, such as a therapy with Alectinib (AF802), Ceritinib (LDK378), Brigatinib (AP26113), Crizotinib (Xalkori), and/or PF-06463922, and/or (2) treating or preventing cancer, wherein the cancer cell comprises the mutant ALK.

Another aspect of the present application relates to use of a compound that binds to ALK or a mutant ALK (e.g., ALK G1202R) (e.g., at the ATP binding site of ALK or of the mutant ALK), such as a compound of Formula (Ia), or a pharmaceutically acceptable salt, hydrate, solvate, prodrug, stereoisomer, or tautomer thereof, in the manufacture of a medicament for (1) inhibiting the mutant ALK, (2) treating or preventing a disease or disorder (e.g., cancer) in which the ALK mutant plays a role, (3) treating or preventing cancer, wherein the cancer cell comprises the mutant ALK, and/or (4) treating or preventing cancer in a subject identified as being in need of inhibition of the mutant ALK for the treatment or prevention of the cancer.

Another aspect of the present application relates to use of a compound of Formula (I) or (Ia), or a pharmaceutically acceptable salt, hydrate, solvate, prodrug, stereoisomer, or tautomer thereof, in the manufacture of a medicament for (1) inhibiting SRPK (e.g., SRPK1 and/or SRPK2), (2) regulating (e.g., inhibiting) VEGF mediated angiogenesis, (3) treating or preventing a disease or disorder in which a VEGF mediated angiogenesis plays a role (e.g., AMD or angiogenesis-dependent cancers), (4) treating or preventing AMD, (5) treating or preventing AMD in a subject identified in need of regulation (e.g., inhibition) of VEGF mediated angiogenesis for the treatment or prevention of AMD, (6) treating or preventing an angiogenesis-dependent cancer (e.g., tumorous cancer), and/or (7) treating or preventing an angiogenesis-dependent cancer (e.g., tumorous cancer) in a subject identified in need of regulation of VEGF mediated angiogenesis for the treatment or prevention of an angiogenesis-dependent cancer.

Another aspect of the present application relates to labeling a SRPK protein, such as SRPK1, with a compound that is capable of binding to the SRPK protein (e.g., a compound of the present application), comprising interacting the SRPK protein with the compound.

The details of the application are set forth in the accompanying description below. Although methods and materials similar or equivalent to those described herein can be used in the practice or testing of the present application, illustrative methods and materials are now described. Other features, objects, and advantages of the application will be apparent from the description and from the claims. In the specification and the appended claims, the singular forms also include the plural unless the context clearly dictates otherwise. Unless defined otherwise, all technical and scientific terms used herein have the same meaning as commonly understood by one of ordinary skill in the art to which this application belongs. All patents and publications cited in this specification are incorporated herein by reference in their entireties.

The contents of all references (including literature references, issued patents, published patent applications, and co-pending patent applications) cited throughout this application are hereby expressly incorporated herein in their entireties by reference. Unless otherwise defined, all technical and scientific terms used herein are accorded the meaning commonly known to one with ordinary skill in the art.

BRIEF DESCRIPTION OF THE DRAWINGS

FIG. 1A: Binding conformation of Compound 6 in the ATP binding site of ALK-wt. Hydrogen bonds are indicated by dashed lines. FIG. 1B: Binding conformation of Compound 6 in the ATP binding site of ALK-G1202R. Hydrogen bonds are indicated by dashed lines.

FIG. 2A and FIG. 2B show Western blotting in NIH-3T3 cells transformed with wild-type EML4-ALK or its Crizotinib resistant secondary mutants. FIG. 2A: Western blotting of Crizotinib, Ceritinib, Alectinib, and Compound 6 against EML4-ALK$^{wt}$NIH-3T3 and EML4-ALK$^{G1202R}$ NIH-3T3. FIG. 2B: Western blotting of Crizotinib, Ceritinib, Alectinib, and Compound 6 against Crizotinib-resistant mutants.

FIG. 7 is the amino acid sequence of SRPK1 (SEQ ID NO: 1). Amino acid residue Y227 is underlined.

DETAILED DESCRIPTION

Compounds of the Application

Figure 1A:
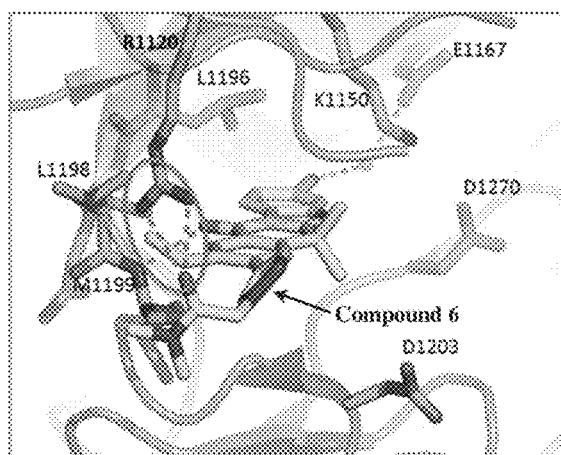
FIG. 1A and FIG. 1B show the detailed views of molecular docking of Compound 6 with wild-type ALK or G1202R ALK.

A first aspect of the application relates to a compound of Formula (I):

(I)

[Chemical structure of Formula (I)]

or a pharmaceutically acceptable salt, hydrate, solvate, prodrug, stereoisomer, or tautomer thereof, wherein:

each $R_1$ is independently $(C_1-C_6)$ alkyl, $(C_1-C_6)$ haloalkyl, $(C_1-C_6)$ alkoxy, $(C_1-C_6)$ haloalkoxy, halogen, NO2, NH2, OH, or CN;

$R_2$ is H or $(C_1-C_3)$ alkyl;

$R_3$ is H, $(C_1-C_6)$ alkyl, or $(C_1-C_6)$ haloalkyl;

$R_4$ is H, $(C_1-C_6)$ alkyl, or $(C_1-C_6)$ haloalkyl;

each $R_5$ is independently $(C_1-C_6)$ alkyl, $(C_1-C_6)$ haloalkyl, $(C_1-C_6)$ alkoxy, $(C_1-C_6)$ haloalkoxy, halogen, $NO_2$, $NH_2$, OH, or CN;

$R_6$ is CN, COOH, $N((C_1-C_6)$ alkyl)-$(CH_2)_{1-4}$—$N((C_1-C_6)$ alkyl)$_2$, $(C_1-C_6)$ alkyl substituted with at least one OH, $(C_2-C_6)$ alkenyl, $C_6-C_{10}$ aryl, heteroaryl comprising a 5- or 6-membered ring and 1-3 heteroatoms selected from N, O and S, or heterocyclyl comprising a 5-membered ring and 1-3 heteroatoms selected from N, O and S, wherein the $(C_2-C_6)$ alkenyl, aryl, heteroaryl, and heterocyclyl are each optionally substituted with one or more Q-T;

Q is a bond or $(C_1-C_6)$ alkyl linker;

T is $(C_1-C_6)$ alkyl, $(C_1-C_6)$ alkylamino, di$(C_1-C_6)$ alkylamino, amino, aminocarbonyl, $(C_1-C_6)$ alkylaminocarbonyl, di$(C_1-C_6)$ alkylaminocarbonyl, OH, $S(O)_qF$, or heterocyclyl comprising a 5 or 6-membered ring and 1-3 heteroatoms selected from N, O and S, wherein when $R_6$ is $(C_2-C_6)$ alkenyl, T is not $(C_1-C_6)$ alkyl;

q is 1 or 2;

m is 0, 1, 2, or 3; and n is 1, 2, or 3.

(1a) In some embodiments of Formula (I), m is 0.
(1b) In some embodiments of Formula (I), m is 1.
(1c) In some embodiments of Formula (I), m is 2.
(1d) In some embodiments of Formula (I), m is 3.
(2a) In some embodiments of Formula (I), at least one $R_1$ is $(C_1-C_6)$ alkyl (e.g., methyl, ethyl, n-propyl, i-propyl, n-butyl, i-butyl, t-butyl, pentyl, or hexyl).
(2b) In some embodiments of Formula (I), at least one $R_1$ is $(C_1-C_6)$ haloalkyl (e.g., $CH_2C_1$, $CHCl_2$, $CCl_3$, $CH_2F$, $CHF_2$, or $CF_3$).
(2c) In some embodiments of Formula (I), at least one $R_1$ is $(C_1-C_6)$ alkoxy (e.g., methoxy, ethoxy, n-propoxy, i-propoxy, n-butoxy, i-butoxy, t-butoxy, pentoxy, or hexyloxy).
(2d) In some embodiments of Formula (I), at least one $R_1$ is $(C_1-C_6)$ haloalkoxy (e.g., $C_1CH_2O$, $FCH_2O$, $Cl_2CHO$, $F_2CHO$, $Cl_3CO$, or $F_3CO$).
(2e) In some embodiments of Formula (I), at least one $R_1$ is halogen (e.g., F, $C_1$, Br, or I), $NO_2$, $NH_2$, OH, or CN.
(3a) In some embodiments of Formula (I), $R_2$ is H.
(3b) In some embodiments of Formula (I), $R_2$ is $(C_1-C_3)$ alkyl (e.g., methyl, ethyl, n-propyl, or i-propyl).
(4a) In some embodiments of Formula (I), $R_3$ is H.
(4b) In some embodiments of Formula (I), $R_3$ is $(C_1-C_6)$ alkyl (e.g., methyl, ethyl, n-propyl, i-propyl, n-butyl, i-butyl, t-butyl, pentyl, or hexyl) or $(C_1-C_6)$ haloalkyl (e.g., $CH_2C_1$, $CHCl_2$, $CCl_3$, $CH_2F$, $CHF_2$, or CF3).
(4c) In some embodiments of Formula (I), $R_3$ is $(C_1-C_6)$ alkyl (e.g., methyl, ethyl, n-propyl, i-propyl, n-butyl, i-butyl, t-butyl, pentyl, or hexyl).
(4d) In some embodiments of Formula (I), $R_3$ is $(C_1-C_3)$ alkyl (e.g., methyl, ethyl, n-propyl, or i-propyl). In further embodiments, $R_3$ is methyl.
(5a) In some embodiments of Formula (I), $R_4$ is H.
(5b) In some embodiments of Formula (I), $R_4$ is $(C_1-C_6)$ alkyl (e.g., methyl, ethyl, n-propyl, i-propyl, n-butyl, i-butyl, t-butyl, pentyl, or hexyl) or $(C_1-C_6)$ haloalkyl (e.g., $CH_2C_1$, $CHCl_2$, $CCl_3$, $CH_2F$, $CHF_2$, or CF3).
(5c) In some embodiments of Formula (I), $R_4$ is $(C_1-C_6)$ alkyl (e.g., methyl, ethyl, n-propyl, i-propyl, n-butyl, i-butyl, t-butyl, pentyl, or hexyl).
(5d) In some embodiments of Formula (I), $R_4$ is $(C_1-C_3)$ alkyl (e.g., methyl, ethyl, n-propyl, or i-propyl). In further embodiments, $R_4$ is methyl.
(6a) In some embodiments of Formula (I), $R_3$ and $R_4$ are each $(C_1-C_6)$ alkyl (e.g., methyl, ethyl, n-propyl, i-propyl, n-butyl, i-butyl, t-butyl, pentyl, or hexyl).
(6b) In some embodiments of Formula (I), $R_3$ and $R_4$ are each $(C_1-C_3)$ alkyl (e.g., methyl, ethyl, n-propyl, or i-propyl). In further embodiments, $R_3$ and $R_4$ are each methyl.
(7a) In some embodiments of Formula (I), n is 1.
(7b) In some embodiments of Formula (I), n is 2.
(7c) In some embodiments of Formula (I), n is 3.
(8a) In some embodiments of Formula (I), at least one $R_5$ is $(C_1-C_6)$ alkyl (e.g., methyl, ethyl, n-propyl, i-propyl, n-butyl, i-butyl, t-butyl, pentyl, or hexyl).
(8b) In some embodiments of Formula (I), at least one $R_5$ is $(C_1-C_3)$ alkyl (e.g., methyl, ethyl, n-propyl, or i-propyl). In further embodiments, at least one $R_5$ is methyl. In other further embodiments, at least one $R_5$ is ethyl. In other further embodiments at least one $R_5$ is propyl.
(8c) In some embodiments of Formula (I), at least one $R_5$ is $(C_1-C_6)$ haloalkyl (e.g., $CH_2C_1$, $CHCl_2$, $CCl_3$, $CH_2F$, $CHF_2$, or CF3).
(8d) In some embodiments of Formula (I), at least one $R_5$ is $(C_1-C_6)$ alkoxy (e.g., methoxy, ethoxy, n-propoxy, i-propoxy, n-butoxy, i-butoxy, t-butoxy, pentoxy, or hexyloxy).
(8e) In some embodiments of Formula (I), at least one $R_5$ is $(C_1-C_6)$ haloalkoxy (e.g., $C_1CH_2O$, $FCH_2O$, $C_{12}CHO$, $F_2CHO$, $C_{13}CO$, or $F_3CO$).
(8f) In some embodiments of Formula (I), at least one $R_5$ is halogen (e.g., F, $C_1$, Br, or I), $NO_2$, $NH_2$, OH, or CN.
(8g) In some embodiments of Formula (I), n is 2 or 3, and at least one $R_5$ is $(C_1-C_3)$ alkyl (e.g., methyl, ethyl, n-propyl, or i-propyl), and the remaining $R_5$ is $(C_1-C_3)$ alkyl (e.g., methyl, ethyl, n-propyl, or i-propyl), $(C_1-C_6)$ haloalkyl (e.g., $CH_2C_1$, $CHCl_2$, $CCl_3$, $CH_2F$, $CHF_2$, or $CF_3$), ($C_1$-$C_6$) alkoxy (e.g., methoxy, ethoxy, n-propoxy, i-propoxy, n-butoxy, i-butoxy, t-butoxy, pentoxy, or hexyloxy), ($C_1$-$C_6$) haloalkoxy (e.g., $C_1CH_2O$, $FCH_2O$, $C_{12}CHO$, $F_2CHO$, $C_{13}CO$, or $F_3CO$), halogen (e.g., F, $C_1$, Br, or I), $NO_2$, $NH_2$, OH, or CN. In further embodiments, n is 2 or 3, and at least one $R_5$ is methyl or ethyl, and the remaining $R_5$ is ($C_1$-$C_3$) alkyl (e.g., methyl, ethyl, n-propyl, or i-propyl), ($C_1$-$C_6$) haloalkyl (e.g., $CH_2C_1$, $CHCl_2$, $CCl_3$, $CH_2F$, $CHF_2$, or $CF_3$), ($C_1$-$C_6$) alkoxy (e.g., methoxy, ethoxy, n-propoxy, i-propoxy, n-butoxy, i-butoxy, t-butoxy, pentoxy, or hexyloxy), ($C_1$-$C_6$) haloalkoxy (e.g., $C_1CH_2O$, $FCH_2O$, $C_{12}CHO$, $F_2CHO$, $Cl_3CO$, or $F_3CO$), halogen (e.g., F, $C_1$, Br, or I), $NO_2$, $NH_2$, OH, or CN. In other further embodiments, n is 2 or 3, and at least one $R_5$ ethyl, and the remaining $R_5$ is ($C_1$-$C_6$) haloalkyl (e.g., $CH_2C_1$, $CHCl_2$, $CCl_3$, $CH_2F$, $CHF_2$, or $CF_3$), ($C_1$-$C_6$) alkoxy (e.g., methoxy, ethoxy, n-propoxy, i-propoxy, n-butoxy, i-butoxy, t-butoxy, pentoxy, or hexyloxy), ($C_1$-$C_6$) haloalkoxy (e.g., $C_1CH_2O$, $FCH_2O$, $C_{12}CHO$, $F_2CHO$, $C_{13}CO$, or $F_3CO$), halogen (e.g., F, $C_1$, Br, or I), $NO_2$, $NH_2$, OH, or CN.

(9) In some embodiments of Formula (I), $R_6$ is CN, COOH, N(($C_1$-$C_6$) alkyl)-$(CH_2)_{1-4}$—N($_4C_1$-$C_6$) alkyl)$_2$, ($C_1$-$C_6$) alkyl substituted with at least one OH, ($C_2$-$C_6$) alkenyl, heteroaryl comprising a 5- or 6-membered ring and 1-3 heteroatoms selected from N, O and S, or heterocyclyl comprising a 5-membered ring and 1-3 heteroatoms selected from N, O and S, wherein the ($C_2$-$C_6$) alkenyl, aryl, heteroaryl, and heterocyclyl are each optionally substituted with one or more Q-T.

(9a) In some embodiments of Formula (I), $R_6$ is CN.

(9b) In some embodiments of Formula (I), $R_6$ is COOH.

(9c) In some embodiments of Formula (I), $R_6$ is N(($C_1$-$C_6$) alkyl)-$(CH_2)_{1-4}$N(($C_1$-$C_6$) alkyl)$_2$, wherein the ($C_1$-$C_6$) alkyl is selected from methyl, ethyl, n-propyl, i-propyl, n-butyl, i-butyl, t-butyl, pentyl, and hexyl. In further embodiments, $R_6$ is N(($C_1$-$C_3$) alkyl)-$(CH_2)_{1-4}$—N(($C_1$-$C_3$) alkyl)$_2$, wherein the ($C_1$-$C_3$) alkyl is selected from methyl, ethyl, n-propyl, and i-propyl. In further embodiments, $R_6$ is N(($C_1$-$C_3$) alkyl)-$(CH_2)_{1-2}$—N(($C_1$-$C_3$) alkyl)$_2$, wherein the ($C_1$-$C_3$) alkyl is selected from methyl, ethyl, n-propyl, and i-propyl. In further embodiments, $R_6$ is N($CH_3$)$CH_2CH_2$N$(CH_3)_2$.

(9d) In some embodiments of Formula (I), $R_6$ is ($C_1$-$C_6$) alkyl (e.g., methyl, ethyl, n-propyl, i-propyl, n-butyl, i-butyl, t-butyl, pentyl, or hexyl) substituted with at least one OH (e.g., one OH, two OH, or three OH). In further embodiments, $R_6$ is ($C_1$-$C_3$) alkyl (e.g., methyl, ethyl, n-propyl, or i-propyl) substituted with at least one OH (e.g., one OH, two OH, or three OH). In further embodiments, $R_6$ is ethyl substituted with at least one OH. In further embodiments, $R_6$ is 1,2-dihydroxyethyl.

(9e) In some embodiments of Formula (I), $R_6$ is ($C_2$-$C_6$) alkenyl (e.g., ethenyl, propenyl, butenyl, pentenyl, or hexenyl), optionally substituted with one or more Q-T.

(9f) In some embodiments of Formula (I), $R_6$ is heteroaryl comprising a 5-membered ring and 1-3 heteroatoms selected from N, O and S (e.g., pyrrolyl, furanyl, thiophenyl, pyrazolyl, imidazolyl, oxazolyl, isoxazolyl, thiazolyl, isothiazolyl, triazolyl, oxadiazolyl, thiadiazolyl, tetrazolyl, etc.), optionally substituted with one or more Q-T. In further embodiments, $R_6$ is heteroaryl comprising a 5-membered ring and at least one nitrogen atom (e.g., pyrrolyl, pyrazolyl, imidazolyl, oxazolyl, isoxazolyl, thiazolyl, isothiazolyl, triazolyl, oxadiazolyl, thiadiazolyl, tetrazolyl, etc.), optionally substituted with one or more Q-T. In further embodiments, $R_6$ is furan-3-yl, thiophen-2-yl, pyrazol-3-yl, pyrazol-4-yl, isoxazol-4-yl, or 1,2,3-triazol-4-yl, optionally substituted with one or more Q-T. In further embodiments, $R_6$ is pyrazol-4-yl, optionally substituted with one or more Q-T.

(9g) In some embodiments of Formula (I), $R_6$ is a heteroaryl comprising a 6-membered ring and 1-3 heteroatoms selected from N, O and S (e.g., pyridinyl, pyridazinyl, pyrimidinyl, pyrazinyl, pyranyl, thiopyranyl, diazinyl, thiazinyl, dioxinyl, triazinyl, etc.), optionally substituted with one or more Q-T. In further embodiments, $R_6$ is heteroaryl comprising a 6-membered ring and at least one nitrogen atom (e.g., pyridinyl, pyridazinyl, pyrimidinyl, pyrazinyl, diazinyl, thiazinyl, triazinyl, etc.), optionally substituted with one or more Q-T. In further embodiments, $R_6$ is pyridin-4-yl, pyridin-3-yl, or pyrimidin-5-yl, optionally substituted with one or more Q-T.

(9h) In some embodiments of Formula (I), $R_6$ is heterocyclyl comprising a 5-membered ring and 1-3 heteroatoms selected from N, O and S (e.g., pyrrolidinyl, tetrahydrofuranyl, tetrahydrothiophenyl, pyrazolidinyl, imidazolidinyl, oxazolidinyl, isoxazolidinyl, thiazolidinyl, isothiazolidinyl, triazolidinyl, oxadiazolidinyl, isoxadiazolidinyl, thiadiazolidinyl, isothiadiazolidinyl, etc.), optionally substituted with one or more Q-T. In some embodiments of Formula (I), $R_6$ is heterocyclyl comprising a 5-membered ring and at least one nitrogen atom (e.g., pyrrolidinyl, pyrazolidinyl, imidazolidinyl, oxazolidinyl, isoxazolidinyl, thiazolidinyl, isothiazolidinyl, triazolidinyl, oxadiazolidinyl, isoxadiazolidinyl, thiadiazolidinyl, isothiadiazolidinyl, etc.), optionally substituted with one or more Q-T.

(9i) In some embodiments of Formula (I), $R_6$ is CN, COOH, N(($C_1$-$C_6$) alkyl)-$(CH_2)_{1-4}$—N(($C_1$-$C_6$) alkyl)$_2$, ($C_1$-$C_6$) alkyl substituted with at least one OH, heteroaryl comprising a 5- or 6-membered ring and 1-3 heteroatoms selected from N, O and S, or heterocyclyl comprising a 5-membered ring and 1-3 heteroatoms selected from N, O and S, wherein the heteroaryl and heterocyclyl are each optionally substituted with one or more Q-T, each of which may be selected from the substituents as described herein.

(9j) In some embodiments of Formula (I), $R_6$ is heteroaryl comprising a 5- or 6-membered ring and 1-3 heteroatoms selected from N, O and S, or heterocyclyl comprising a 5-membered ring and 1-3 heteroatoms selected from N, O and S, wherein the heteroaryl and heterocyclyl are each optionally substituted with one or more Q-T, each of which may be selected from the substituents as described herein.

(9k) In some embodiments of Formula (I), $R_6$ is heteroaryl comprising a 5- or 6-membered ring and 1-3 heteroatoms selected from N, O and S, wherein the heteroaryl is optionally substituted with one or more Q-T, each of which may be selected from the substituents as described herein.

(9l) In some embodiments of Formula (I), $R_6$ is $C_6$-$C_{10}$ aryl optionally substituted with one or more Q-T, each of which may be selected from the substituents as described herein. In some embodiments of Formula (I), $R_6$ is $C_6$-$C_{10}$ aryl optionally substituted with one or more Q-T, wherein T is $S(O)_qF$. In some embodiments of Formula (I), $R_6$ is $C_6$-$C_{10}$ aryl optionally substituted with one or more Q-T, wherein T is $S(O)_2F$.

(9m) In some embodiments of Formula (I), $R_6$ is phenyl optionally substituted with one or more Q-T, each of which may be selected from the substituents as described herein. In some embodiments of Formula (I), $R_6$ is phenyl optionally substituted with one or more Q-T, wherein T is $S(O)_qF$. In some embodiments of Formula (I), $R_6$ is phenyl optionally substituted with one or more Q-T, wherein T is $S(O)_2F$.

(10a) In some embodiments of Formula (I), Q is a bond.

(10b) In some embodiments of Formula (I), Q is a ($C_1$-$C_6$) alkyl linker (e.g., methyl linker (—$CH_2$—), ethyl linker (—$CH_2CH_2$— or —$CH(CH_3)$—), propyl linker (—$CH_2CH_2CH_2$—, —$CH(CH_3)CH_2$—, or —$C(CH_3)_2$—), butyl linker (—$CH_2CH_2CH_2CH_2$—, —$CH(CH_3)CH_2CH_2$—, —$CH_2CH(CH_3)CH_2$—, —$C(CH_3)_2CH_2$—, or —$CH(CH_3)CH(CH_3)$—), pentyl linker (—$CH_2CH_2CH_2CH_2CH_2$—, —$CH(CH_3)CH_2CH_2CH_2$—, —$CH_2CH(CH_3)CH_2CH_2$—, —$C(CH_3)_2CH_2CH_2$—, or —$CH_2C(CH_3)_2CH_2$—), or hexyl linker (—$CH_2CH_2CH_2CH_2CH_2CH_2$—). In further embodiments, Q is a ($C_1$-$C_3$) alkyl linker (e.g., methyl linker (—$CH_2$—), ethyl linker (—$CH_2CH_2$— or —$CH(CH_3)$—), or propyl linker (—$CH_2CH_2CH_2$—, —$CH(CH_3)CH_2$—, or —$C(CH_3)_2$—)). In further embodiments, Q is —$CH_2$—, —$CH_2CH_2$—, —$CH_2CH_2CH_2$—, or —$C(CH_3)_2$—.

(11) In some embodiments of Formula (I), T is ($C_1$-$C_6$) alkyl, ($C_1$-$C_6$) alkylamino, di($C_1$-$C_6$) alkylamino, amino, aminocarbonyl, ($C_1$-$C_6$) alkylaminocarbonyl, di($C_1$-$C_6$) alkylaminocarbonyl, OH, or heterocyclyl comprising a 5 or 6-membered ring and 1-3 heteroatoms selected from N, O and S, wherein when $R_6$ is ($C_2$-$C_6$) alkenyl, T is not ($C_1$-$C_6$) alkyl.

(11a) In some embodiments of Formula (I), T is ($C_1$-$C_6$) alkyl (e.g., methyl, ethyl, n-propyl, i-propyl, n-butyl, i-butyl, t-butyl, pentyl, or hexyl). In further embodiments, T is ($C_1$-$C_3$) alkyl (e.g., methyl, ethyl, n-propyl, or i-propyl). In further embodiments, T is methyl.

(11b) In some embodiments of Formula (I), T is ($C_1$-$C_6$) alkylamino (e.g., methylamino, ethylamino, propylamino, butylamino, pentylamino, or hexylamino).

(11c) In some embodiments of Formula (I), T is di($C_1$-$C_6$) alkylamino (e.g., dimethylamino, diethylamino, dipropylamino, dibutylamino, dipentylamino, or dihexylamino). In further embodiments, T is di($C_1$-$C_3$) alkylamino (e.g., dimethylamino, diethylamino, or dipropylamino). In further embodiments, T is dimethylamino.

(11d) In some embodiments of Formula (I), T is amino.

(11e) In some embodiments of Formula (I), T is aminocarbonyl (i.e., $NH_2C(O)$).

(11f) In some embodiments of Formula (I), T is ($C_1$-$C_6$) alkylaminocarbonyl (e.g., methylaminocarbonyl, ethylaminocarbonyl, propylaminocarbonyl, butylaminocarbonyl, pentylaminocarbonyl, or hexylaminocarbonyl). In further embodiments, T is methylaminocarbonyl (i.e., $CH_3NHC(O)$).

(11g) In some embodiments of Formula (I), T is di ($C_1$-$C_6$) alkylaminocarbonyl (e.g., dimethylaminocarbonyl, diethylaminocarbonyl, dipropylaminocarbonyl, dibutylaminocarbonyl, dipentylaminocarbonyl, or dihexylaminocarbonyl). In further embodiments, T is dimethylaminocarbonyl (i.e., $(CH_3)_2NC(O)$).

(11h) In some embodiments of Formula (I), T is OH.

(11i) In some embodiments of Formula (I), T is heterocyclyl comprising a 5-membered ring and 1-3 heteroatoms selected from N, O and S (e.g., pyrrolidinyl, tetrahydrofuranyl, tetrahydrothiophenyl, pyrazolidinyl, imidazolidinyl, oxazolidinyl, isoxazolidinyl, thiazolidinyl, isothiazolidinyl, triazolidinyl, oxadiazolidinyl, isoxadiazolidinyl, thiadiazolidinyl, isothiadiazolidinyl, etc.).

(11j) In some embodiments of Formula (I), T is heterocyclyl comprising a 6-membered ring and 1-3 heteroatoms selected from N, O and S (e.g., piperidinyl, tetrahydropyranyl, piperazinyl, morpholinyl, thiomorpholinyl, dioxanyl, etc.). In further embodiments, T is morpholinyl. In other further embodiments, T is tetrahydropyranyl. In other further embodiments, T is piperidinyl.

(11k) In some embodiments of Formula (I), T is S(O)F. In some embodiments of Formula (I), T is $S(O)_2F$.

In some embodiments of Formula (I), each of the substituents defined for any one of $R_1$, $R_2$, $R_3$, $R_4$, $R_5$, $R_6$, Q, T, q, m, and n can be combined with any of the substituents defined for the remainder of $R_1$, $R_2$, $R_3$, $R_4$, $R_5$, $R_6$, Q, T, q, m, and n.

(12) In some embodiments, m is 0, and $R_2$ is H.

(13) In some embodiments, m is 0, $R_3$ is ($C_1$-$C_3$) alkyl (e.g., methyl, ethyl, n-propyl, or i-propyl), and $R_4$ is ($C_1$-$C_3$) alkyl (e.g., methyl, ethyl, n-propyl, or i-propyl). In further embodiments, m is 0, and $R_3$ and $R_4$ are each methyl.

(14) In some embodiments, $R_2$ is H, $R_3$ is ($C_1$-$C_3$) alkyl (e.g., methyl, ethyl, n-propyl, or i-propyl), and $R_4$ is ($C_1$-$C_3$) alkyl (e.g., methyl, ethyl, n-propyl, or i-propyl). In further embodiments, $R_2$ is H, and $R_3$ and $R_4$ are each methyl.

(15) In some embodiments, m is 0, $R_2$ is H, $R_3$ is ($C_1$-$C_3$) alkyl (e.g., methyl, ethyl, n-propyl, or i-propyl), and $R_4$ is ($C_1$-$C_3$) alkyl (e.g., methyl, ethyl, n-propyl, or i-propyl). In further embodiments, m is 0, $R_2$ is H, and $R_3$ and $R_4$ are each methyl.

(16) In some embodiments, m is 0, and n is 1.

(17) In some embodiments, $R_2$ is H, and n is 1.

(18) In some embodiments, $R_3$ is ($C_1$-$C_3$) alkyl (e.g., methyl, ethyl, n-propyl, or i-propyl), $R_4$ is ($C_1$-$C_3$) alkyl (e.g., methyl, ethyl, n-propyl, or i-propyl), and n is 1. In further embodiments, $R_3$ and $R_4$ are each methyl, and n is 1.

(19) In some embodiments, m is 0, $R_2$ is H, and n is 1.

(20) In some embodiments, m is 0, $R_3$ is ($C_1$-$C_3$) alkyl (e.g., methyl, ethyl, n-propyl, or i-propyl), $R_4$ is ($C_1$-$C_3$) alkyl (e.g., methyl, ethyl, n-propyl, or i-propyl), and n is 1. In further embodiments, m is 0, $R_3$ and $R_4$ are each methyl, and n is 1.

(21) In some embodiments, $R_2$ is H, $R_3$ is ($C_1$-$C_3$) alkyl (e.g., methyl, ethyl, n-propyl, or i-propyl), $R_4$ is ($C_1$-$C_3$) alkyl (e.g., methyl, ethyl, n-propyl, or i-propyl), and n is 1. In further embodiments, $R_2$ is H, $R_3$ and $R_4$ are each methyl, and n is 1.

(22) In some embodiments, m is 0, $R_2$ is H, $R_3$ is ($C_1$-$C_3$) alkyl (e.g., methyl, ethyl, n-propyl, or i-propyl), $R_4$ is ($C_1$-$C_3$) alkyl (e.g., methyl, ethyl, n-propyl, or i-propyl), and n is 1. In further embodiments, m is 0, $R_2$ is H, $R_3$ and $R_4$ are each methyl, and n is 1.

(23) In some embodiments, n is 1, and $R_5$ is ($C_1$-$C_3$) alkyl (e.g., methyl, ethyl, n-propyl, or i-propyl). In further embodiments, n is 1, and $R_5$ is ethyl.

(24) In some embodiments, m is 0, n is 1, and $R_5$ is ($C_1$-$C_3$) alkyl (e.g., methyl, ethyl, n-propyl, or i-propyl). In further embodiments, m is 0, n is 1, and $R_5$ is ethyl.

(25) In some embodiments, $R_2$ is H, n is 1, and $R_5$ is ($C_1$-$C_3$) alkyl (e.g., methyl, ethyl, n-propyl, or i-propyl). In further embodiments, $R_2$ is H, n is 1, and $R_5$ is ethyl.

(26) In some embodiments, $R_3$ is ($C_1$-$C_3$) alkyl (e.g., methyl, ethyl, n-propyl, or i-propyl), $R_4$ is ($C_1$-$C_3$) alkyl (e.g., methyl, ethyl, n-propyl, or i-propyl), n is 1, and $R_5$ is ($C_1$-$C_3$) alkyl (e.g., methyl, ethyl, n-propyl, or i-propyl). In further embodiments, $R_3$ and $R_4$ are each methyl, n is 1, and $R_5$ is ethyl.

(27) In some embodiments, m is 0, $R_3$ is ($C_1$-$C_3$) alkyl (e.g., methyl, ethyl, n-propyl, or i-propyl), $R_4$ is ($C_1$-$C_3$) alkyl (e.g., methyl, ethyl, n-propyl, or i-propyl), n is 1, and $R_5$ is ($C_1$-$C_3$) alkyl (e.g., methyl, ethyl, n-propyl, or i-propyl). In further embodiments, m is 0, $R_3$ and $R_4$ are each methyl, n is 1, and $R_5$ is ethyl.

(28) In some embodiments, $R_2$ is H, $R_3$ is ($C_1$-$C_3$) alkyl (e.g., methyl, ethyl, n-propyl, or i-propyl), $R_4$ is ($C_1$-$C_3$) alkyl (e.g., methyl, ethyl, n-propyl, or i-propyl), n is 1, and $R_5$ is ($C_1$-$C_3$) alkyl (e.g., methyl, ethyl, n-propyl, or i-propyl). In further embodiments, $R_2$ is H, $R_3$ and $R_4$ are each methyl, n is 1, and $R_5$ is ethyl.

(29) In some embodiments, m is 0, $R_2$ is H, n is 1, and $R_5$ is ($C_1$-$C_3$) alkyl (e.g., methyl, ethyl, n-propyl, or i-propyl). In further embodiments, m is 0, $R_2$ is H, n is 1, and $R_5$ is ethyl.

(30) In some embodiments, m is 0, $R_2$ is H, $R_3$ is ($C_1$-$C_3$) alkyl (e.g., methyl, ethyl, n-propyl, or i-propyl), $R_4$ is ($C_1$-$C_3$) alkyl (e.g., methyl, ethyl, n-propyl, or i-propyl), n is 1, and $R_5$ is ($C_1$-$C_3$) alkyl (e.g., methyl, ethyl, n-propyl, or i-propyl). In further embodiments, m is 0, $R_2$ is H, $R_3$ and $R_4$ are each methyl, n is 1, and $R_5$ is ethyl.

(31) In some embodiments, n is 2 or 3, and at least one $R_5$ is ($C_1$-$C_3$) alkyl (e.g., methyl, ethyl, n-propyl, or i-propyl). In further embodiments, n is 2 or 3, and at least one $R_5$ is ethyl.

(32) In some embodiments, m is 0, n is 2 or 3, and at least one $R_5$ is ($C_1$-$C_3$) alkyl (e.g., methyl, ethyl, n-propyl, or i-propyl). In further embodiments, m is 0, n is 2 or 3, and at least one $R_5$ is ethyl.

(33) In some embodiments, $R_2$ is H, n is 2 or 3, and at least one $R_5$ is ($C_1$-$C_3$) alkyl (e.g., methyl, ethyl, n-propyl, or i-propyl). In further embodiments, $R_2$ is H, n is 2 or 3, and at least one $R_5$ is ethyl.

(34) In some embodiments, $R_3$ is ($C_1$-$C_3$) alkyl (e.g., methyl, ethyl, n-propyl, or i-propyl), $R_4$ is ($C_1$-$C_3$) alkyl (e.g., methyl, ethyl, n-propyl, or i-propyl), n is 2 or 3, and at least one $R_5$ is ($C_1$-$C_3$) alkyl (e.g., methyl, ethyl, n-propyl, or i-propyl). In further embodiments, $R_3$ and $R_4$ are each methyl, n is 2 or 3, and at least one $R_5$ is ethyl.

(35) In some embodiments, m is 0, $R_3$ is ($C_1$-$C_3$) alkyl (e.g., methyl, ethyl, n-propyl, or i-propyl), $R_4$ is ($C_1$-$C_3$) alkyl (e.g., methyl, ethyl, n-propyl, or i-propyl), n is 2 or 3, and at least one $R_5$ is ($C_1$-$C_3$) alkyl (e.g., methyl, ethyl, n-propyl, or i-propyl). In further embodiments, m is 0, $R_3$ and $R_4$ are each methyl, n is 2 or 3, and at least one $R_5$ is ethyl.

(36) In some embodiments, $R_2$ is H, $R_3$ is ($C_1$-$C_3$) alkyl (e.g., methyl, ethyl, n-propyl, or i-propyl), $R_4$ is ($C_1$-$C_3$) alkyl (e.g., methyl, ethyl, n-propyl, or i-propyl), n is 2 or 3, and at least one $R_5$ is ($C_1$-$C_3$) alkyl (e.g., methyl, ethyl, n-propyl, or i-propyl). In further embodiments, $R_2$ is H, $R_3$ and $R_4$ are each methyl, n is 2 or 3, and at least one $R_5$ is ethyl.

(37) In some embodiments, m is 0, $R_2$ is H, n is 2 or 3, and at least one $R_5$ is ($C_1$-$C_3$) alkyl (e.g., methyl, ethyl, n-propyl, or i-propyl). In further embodiments, m is 0, $R_2$ is H, n is 2 or 3, and at least one $R_5$ is ethyl.

(38) In some embodiments, m is 0, $R_2$ is H, $R_3$ is ($C_1$-$C_3$) alkyl (e.g., methyl, ethyl, n-propyl, or i-propyl), $R_4$ is ($C_1$-$C_3$) alkyl (e.g., methyl, ethyl, n-propyl, or i-propyl), n is 2 or 3, and at least one $R_5$ is ($C_1$-$C_3$) alkyl (e.g., methyl, ethyl, n-propyl, or i-propyl). In further embodiments, m is 0, $R_2$ is H, $R_3$ and $R_4$ are each methyl, n is 2 or 3, and at least one $R_5$ is ethyl.

(39) In some embodiments, $R_1$, $R_2$, $R_3$, $R_4$, $R_5$, q, m, and n are each as described in any one of (12)-(38), and $R_6$ is described in any one of (9)-(9m).

(40) In some embodiments, $R_1$, $R_2$, $R_3$, $R_4$, $R_5$, q, m, and n are each as described in any one of (12)-(38), and $R_6$ is as described in any one of (9a)-(9k).

(41) In some embodiments, $R_1$, $R_2$, $R_3$, $R_4$, $R_5$, q, m, and n are each as described in any one of (12)-(38), and $R_6$ is as described in any one of (9i)-(9k).

(42) In some embodiments, $R_1$, $R_2$, $R_3$, $R_4$, $R_5$, q, m, and n are each as described in any one of (12)-(38), and $R_6$ is as described in any one of (9f)-(9h).

(43) In some embodiments, $R_1$, $R_2$, $R_3$, $R_4$, $R_5$, q, m, and n are each as described in any one of (12)-(38), and $R_6$ is as described in (9f).

(44) In some embodiments, $R_1$, $R_2$, $R_3$, $R_4$, $R_5$, q, m, and n are each as described in any one of (12)-(38), and $R_6$ is as described in (9l) or (9m).

(45) In some embodiments, $R_1$, $R_2$, $R_3$, $R_4$, $R_5$, q, m, and n are each as described in any one of (12)-(38), and $R_6$ is as described in (9m).

In some embodiments, the compound of Formula (I) has the structure of Formula (II):

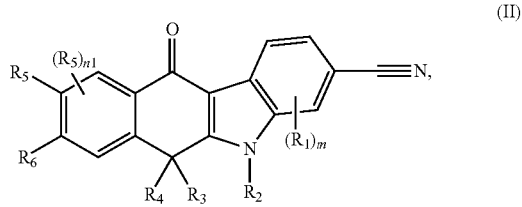

(II)

or a pharmaceutically acceptable salt, hydrate, solvate, prodrug, stereoisomer, or tautomer thereof, wherein n1 is 0, 1, or 2, and $R_1$, $R_2$, $R_3$, $R_4$, $R_5$, $R_6$, Q, T, and m are each as defined herein above in Formula (I).

In some embodiments of Formula (II), n1 is 0.
In some embodiments of Formula (II), n1 is 1.
In some embodiments of Formula (II), n1 is 2.
In some embodiments of Formula (II), each of $R_1$, $R_2$, $R_3$, $R_4$, $R_5$, $R_6$, Q, T, q, and m can be selected from the substituent groups described above in Formula (I).

In some embodiments of Formula (II), each of the substituents defined for any one of $R_1$, $R_2$, $R_3$, $R_4$, $R_5$, $R_6$, Q, T, q, m, and n1 can be combined with any of the substituents defined for the remainder of $R_1$, $R_2$, $R_3$, $R_4$, $R_5$, $R_6$, Q, T, q, m, and n1.

In some embodiments, the compound of Formula (I) has the structure of Formula (IIa) or (IIb):

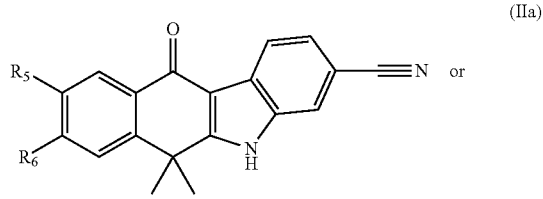

(IIa)

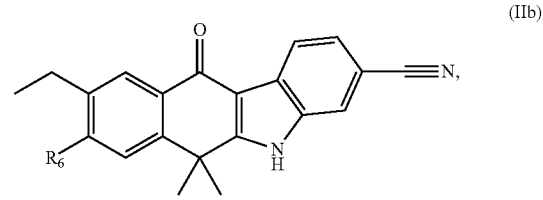

(IIb)

or a pharmaceutically acceptable salt, hydrate, solvate, prodrug, stereoisomer, or tautomer thereof, wherein $R_5$ and $R_6$ are each as defined herein above in Formula (I).

In some embodiments of Formula (IIa), $R_5$ is ($C_1$-$C_6$) alkyl (e.g., methyl, ethyl, n-propyl, i-propyl, n-butyl, i-butyl, t-butyl, pentyl, or hexyl).

In some embodiments of Formula (IIa), $R_5$ is ($C_1$-$C_3$) alkyl (e.g., methyl, ethyl, n-propyl, or i-propyl). In further embodiments, $R_5$ is methyl. In other further embodiments, $R_5$ is ethyl. In other further embodiments $R_5$ is propyl.

In some embodiments of Formula (IIa), $R_5$ is ethyl.

In some embodiments of Formula (IIa), $R_5$ is ($C_1$-$C_6$) haloalkyl (e.g., $CH_2Cl$, $CHCl_2$, $CCl_3$, $CH_2F$, $CHF_2$, or $CF_3$).

In some embodiments of Formula (IIa), $R_5$ is ($C_1$-$C_6$) alkoxy (e.g., methoxy, ethoxy, n-propoxy, i-propoxy, n-butoxy, i-butoxy, t-butoxy, pentoxy, or hexyloxy).

In some embodiments of Formula (IIa), $R_5$ is ($C_1$-$C_6$) haloalkoxy (e.g., $ClCH_2O$, $FCH_2O$, $Cl_2CHO$, $F_2CHO$, $Cl_3CO$, or $F_3CO$).

In some embodiments of Formula (IIa), $R_5$ is halogen (e.g., F, Cl, Br, or I), $NO_2$, $NH_2$, OH, or CN.

In some embodiments of Formula (IIa) or (IIb), $R_6$ is CN.

In some embodiments of Formula (IIa) or (IIb), $R_6$ is COOH.

In some embodiments of Formula (IIa) or (IIb), $R_6$ is N(($C_1$-$C_6$) alkyl)-$(CH_2)_{1-4}$—N(($C_1$-$C_6$) alkyl)$_2$, wherein the ($C_1$-$C_6$) alkyl is selected from methyl, ethyl, n-propyl, propyl, n-butyl, i-butyl, t-butyl, pentyl, and hexyl. In further embodiments, $R_6$ is N(($C_1$-$C_3$) alkyl)-$(CH_2)_{1-4}$—N(($C_1$-$C_3$) alkyl)$_2$, wherein the ($C_1$-$C_3$) alkyl is selected from methyl, ethyl, n-propyl, and i-propyl. In further embodiments, $R_6$ is N(($C_1$-$C_3$) alkyl)-$(CH_2)_{1-2}$—N(($C_1$-$C_3$) alkyl)$_2$, wherein the ($C_1$-$C_3$) alkyl is selected from methyl, ethyl, n-propyl, and i-propyl. In further embodiments, $R_6$ is $N(CH_3)CH_2CH_2N(CH_3)_2$.

In some embodiments of Formula (IIa) or (IIb), $R_6$ is ($C_1$-$C_6$) alkyl (e.g., methyl, ethyl, n-propyl, i-propyl, n-butyl, i-butyl, t-butyl, pentyl, or hexyl) substituted with at least one OH (e.g., one OH, two OH, or three OH). In further embodiments, $R_6$ is ($C_1$-$C_3$) alkyl (e.g., methyl, ethyl, n-propyl, or i-propyl) substituted with at least one OH (e.g., one OH, two OH, or three OH). In further embodiments, $R_6$ is ethyl substituted with at least one OH. In further embodiments, $R_6$ is 1,2-dihydroxyethyl.

In some embodiments of Formula (IIa) or (IIb), $R_6$ is ($C_2$-$C_6$) alkenyl (e.g., ethenyl, propenyl, butenyl, pentenyl, or hexenyl), optionally substituted with one or more Q-T.

In some embodiments of Formula (IIa) or (IIb), $R_6$ is heteroaryl comprising a 5-membered ring and 1-3 heteroatoms selected from N, O and S (e.g., pyrrolyl, furanyl, thiophenyl, pyrazolyl, imidazolyl, oxazolyl, isoxazolyl, thiazolyl, isothiazolyl, triazolyl, oxadiazolyl, thiadiazolyl, tetrazolyl, etc.), optionally substituted with one or more Q-T. In further embodiments, $R_6$ is heteroaryl comprising a 5-membered ring and at least one nitrogen atom (e.g., pyrrolyl, pyrazolyl, imidazolyl, oxazolyl, isoxazolyl, thiazolyl, isothiazolyl, triazolyl, oxadiazolyl, thiadiazolyl, tetrazolyl, etc.), optionally substituted with one or more Q-T. In further embodiments, $R_6$ is furan-3-yl, thiophen-2-yl, pyrazol-3-yl, pyrazol-4-yl, isoxazol-4-yl, or 1,2,3-triazol-4-yl, optionally substituted with one or more Q-T. In further embodiments, $R_6$ is pyrazol-4-yl, optionally substituted with one or more Q-T.

In some embodiments of Formula (IIa) or (IIb), $R_6$ is a heteroaryl comprising a 6-membered ring and 1-3 heteroatoms selected from N, O and S (e.g., pyridinyl, pyridazinyl, pyrimidinyl, pyrazinyl, pyranyl, thiopyranyl, diazinyl, thiazinyl, dioxinyl, triazinyl, etc.), optionally substituted with one or more Q-T. In further embodiments, $R_6$ is heteroaryl comprising a 6-membered ring and at least one nitrogen atom (e.g., pyridinyl, pyridazinyl, pyrimidinyl, pyrazinyl, diazinyl, thiazinyl, triazinyl, etc.), optionally substituted with one or more Q-T. In further embodiments, $R_6$ is pyridin-4-yl, pyridin-3-yl, or pyrimidin-5-yl, optionally substituted with one or more Q-T.

In some embodiments of Formula (IIa) or (IIb), $R_6$ is heterocyclyl comprising a 5-membered ring and 1-3 heteroatoms selected from N, O and S (e.g., pyrrolidinyl, tetrahydrofuranyl, tetrahydrothiophenyl, pyrazolidinyl, imidazolidinyl, oxazolidinyl, isoxazolidinyl, thiazolidinyl, isothiazolidinyl, triazolidinyl, oxadiazolidinyl, isoxadiazolidinyl, thiadiazolidinyl, isothiadiazolidinyl, etc.), optionally substituted with one or more Q-T. In some embodiments of Formula (IIa) or (IIb), $R_6$ is heterocyclyl comprising a 5-membered ring and at least one nitrogen atom (e.g., pyrrolidinyl, pyrazolidinyl, imidazolidinyl, oxazolidinyl, isoxazolidinyl, thiazolidinyl, isothiazolidinyl, triazolidinyl, oxadiazolidinyl, isoxadiazolidinyl, thiadiazolidinyl, isothiadiazolidinyl, etc.), optionally substituted with one or more Q-T.

In some embodiments of Formula (IIa) or (IIb), $R_6$ is CN, COOH, N(($C_1$-$C_6$) alkyl)-$(CH_2)_{1-4}$—N(($C_1$-$C_6$) alkyl)$_2$, ($C_1$-$C_6$) alkyl substituted with at least one OH, heteroaryl comprising a 5- or 6-membered ring and 1-3 heteroatoms selected from N, O and S, or heterocyclyl comprising a 5-membered ring and 1-3 heteroatoms selected from N, O and S, wherein the heteroaryl and heterocyclyl are each optionally substituted with one or more Q-T, each of which may be selected from the substituents as described herein.

In some embodiments of Formula (IIa) or (IIb), $R_6$ is heteroaryl comprising a 5- or 6-membered ring and 1-3 heteroatoms selected from N, O and S, or heterocyclyl comprising a 5-membered ring and 1-3 heteroatoms selected from N, O and S, wherein the heteroaryl and heterocyclyl are each optionally substituted with one or more Q-T, each of which may be selected from the substituents as described herein.

In some embodiments of Formula (IIa) or (IIb), $R_6$ is heteroaryl comprising a 5- or 6-membered ring and 1-3 heteroatoms selected from N, O and S, wherein the heteroaryl is optionally substituted with one or more Q-T, each of which may be selected from the substituents as described herein.

In some embodiments of Formula (IIa) or (IIb), $R_6$ is $C_6$-$C_{10}$ aryl optionally substituted with one or more Q-T, each of which may be selected from the substituents as described herein. In some embodiments of Formula (I), $R_6$ is $C_6$-$C_{10}$ aryl optionally substituted with one or more Q-T, wherein T is $S(O)_qF$. In some embodiments of Formula (I), $R_6$ is $C_6$-$C_{10}$ aryl optionally substituted with one or more Q-T, wherein T is $S(O)_2F$.

In some embodiments of Formula (IIa) or (IIb), $R_6$ is phenyl optionally substituted with one or more Q-T, each of which may be selected from the substituents as described herein. In some embodiments of Formula (I), $R_6$ is phenyl optionally substituted with one or more Q-T, wherein T is $S(O)_qF$. In some embodiments of Formula (I), $R_6$ is phenyl optionally substituted with one or more Q-T, wherein T is $S(O)_2F$.

In some embodiments of Formula (IIa) or (IIb), Q is a bond.

In some embodiments of Formula (IIa) or (IIb), Q is a ($C_1$-$C_6$) alkyl linker (e.g., methyl linker (—$CH_2$—), ethyl linker (—$CH_2CH_2$— or —$CH(CH_3)$—), propyl linker (—$CH_2CH_2CH_2$—, —$CH(CH_3)CH_2$—, or —$C(CH_3)_2$—), butyl linker (—$CH_2CH_2CH_2CH_2$—, —$CH(CH_3)CH_2CH_2$—, —$CH_2CH(CH_3)CH_2$—, —$C(CH_3)_2CH_2$—, or —CH(CH₃)CH(CH₃)—), pentyl linker (—CH₂CH₂CH₂CH₂CH₂—, —CH(CH₃)CH₂CH₂CH₂—, —CH₂CH(CH₃)CH₂CH₂—, —C(CH₃)₂CH₂CH₂—, or —CH₂C(CH₃)₂CH₂—), or hexyl linker (—CH₂CH₂CH₂CH₂CH₂CH₂—). In further embodiments, Q is a ($C_1$-$C_3$) alkyl linker (e.g., methyl linker (—CH₂—), ethyl linker (—CH₂CH₂— or —CH(CH₃)—), or propyl linker (—CH₂CH₂CH₂—, —CH(CH₃)CH₂—, or —C(CH₃)₂—)). In further embodiments, Q is —CH₂—, —CH₂CH₂—, —CH₂CH₂CH₂—, or —C(CH₃)₂—.

In some embodiments of Formula (IIa) or (IIb), T is ($C_1$-$C_6$) alkyl (e.g., methyl, ethyl, n-propyl, i-propyl, n-butyl, i-butyl, t-butyl, pentyl, or hexyl). In further embodiments, T is ($C_1$-$C_3$) alkyl (e.g., methyl, ethyl, n-propyl, or i-propyl). In further embodiments, T is methyl.

In some embodiments of Formula (IIa) or (IIb), T is ($C_1$-$C_6$) alkylamino (e.g., methylamino, ethylamino, propylamino, butylamino, pentylamino, or hexylamino).

In some embodiments of Formula (IIa) or (IIb), T is di($C_1$-$C_6$) alkylamino (e.g., dimethylamino, diethylamino, dipropylamino, dibutylamino, dipentylamino, or dihexylamino). In further embodiments, T is di($C_1$-$C_3$) alkylamino (e.g., dimethylamino, diethylamino, or dipropylamino). In further embodiments, T is dimethylamino.

In some embodiments of Formula (IIa) or (IIb), T is amino.

In some embodiments of Formula (IIa) or (IIb), T is aminocarbonyl (i.e., NH₂C(O)).

In some embodiments of Formula (IIa) or (IIb), T is ($C_1$-$C_6$) alkylaminocarbonyl (e.g., methylaminocarbonyl, ethylaminocarbonyl, propylaminocarbonyl, butylaminocarbonyl, pentylaminocarbonyl, or hexylaminocarbonyl). In further embodiments, T is methylaminocarbonyl (i.e., CH₃NHC(O)).

In some embodiments of Formula (IIa) or (IIb), T is di ($C_1$-$C_6$) alkylaminocarbonyl (e.g., dimethylaminocarbonyl, diethylaminocarbonyl, dipropylaminocarbonyl, dibutylaminocarbonyl, dipentylaminocarbonyl, or dihexylaminocarbonyl). In further embodiments, T is dimethylaminocarbonyl (i.e., (CH₃)₂NC(O)).

In some embodiments of Formula (IIa) or (IIb), T is OH.

In some embodiments of Formula (IIa) or (IIb), T is heterocyclyl comprising a 5-membered ring and 1-3 heteroatoms selected from N, O and S (e.g., pyrrolidinyl, tetrahydrofuranyl, tetrahydrothiophenyl, pyrazolidinyl, imidazolidinyl, oxazolidinyl, isoxazolidinyl, thiazolidinyl, isothiazolidinyl, triazolidinyl, oxadiazolidinyl, isoxadiazolidinyl, thiadiazolidinyl, isothiadiazolidinyl, etc.).

In some embodiments of Formula (IIa) or (IIb), T is heterocyclyl comprising a 6-membered ring and 1-3 heteroatoms selected from N, O and S (e.g., piperidinyl, tetrahydropyranyl, piperazinyl, morpholinyl, thiomorpholinyl, dioxanyl, etc.). In further embodiments, T is morpholinyl. In other further embodiments, T is tetrahydropyranyl. In other further embodiments, T is piperidinyl.

In some embodiments of Formula (IIa) or (IIb), T is S(O)F. In some embodiments of Formula (IIa) or (IIb), T is S(O)₂F.

In some embodiments of Formula (IIa) or (IIb), each of the substituents defined for any one of $R_5$, $R_6$, Q, T, and q can be combined with any of the substituents defined for the remainder of $R_5$, $R_6$, Q, T, and q.

Another aspect of the application relates to a compound of Formula (Ia):

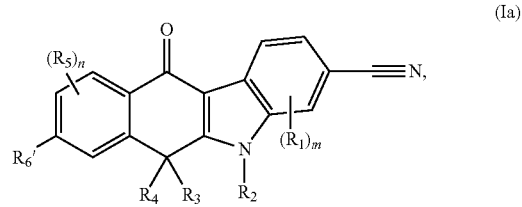

or a pharmaceutically acceptable salt, hydrate, solvate, prodrug, stereoisomer, or tautomer thereof, for
  inhibiting a mutant ALK (e.g., ALK G1202R);
  treating or preventing a disease or disorder (e.g., cancer) in which a mutant ALK (e.g., ALK G1202R) plays a role;
  treating or preventing cancer in a subject identified as being in need of inhibition of a mutant ALK (e.g., ALK G1202R) for the treatment or prevention of the cancer;
  treating or preventing a disease or disorder (e.g., cancer) resistant to an ALK targeted therapy, such as a therapy with Alectinib (AF802), Ceritinib (LDK378), Brigatinib (AP26113), Crizotinib (Xalkori), and/or PF-06463922;
  treating or preventing cancer, wherein the cancer cell comprises the mutant ALK (e.g., ALK G1202R);
  inhibiting SRPK (e.g., SRPK1 and/or SRPK2);
  regulating (e.g., inhibiting) VEGF mediated angiogenesis;
  treating or preventing a disease or disorder in which a VEGF mediated angiogenesis plays a role (e.g., AMD or angiogenesis-dependent cancers);
  treating or preventing AMD (e.g., in a subject identified in need of regulation (e.g., inhibition) of VEGF mediated angiogenesis for the treatment or prevention of AMD); or
  treating or preventing an angiogenesis-dependent cancer (e.g., tumorous cancer) (e.g., in a subject identified in need of regulation of VEGF mediated angiogenesis for the treatment or prevention of an angiogenesis-dependent cancer),
wherein:
  each $R_1$ is independently ($C_1$-$C_6$) alkyl, ($C_1$-$C_6$) haloalkyl, ($C_1$-$C_6$) alkoxy, ($C_1$-$C_6$) haloalkoxy, halogen, NO₂, NH₂, OH, or CN;
  $R_2$ is H or ($C_1$-$C_3$) alkyl;
  $R_3$ is H, ($C_1$-$C_6$) alkyl, or ($C_1$-$C_6$) haloalkyl;
  $R_4$ is H, ($C_1$-$C_6$) alkyl, or ($C_1$-$C_6$) haloalkyl;
  each $R_5$ is independently ($C_1$-$C_6$) alkyl, ($C_1$-$C_6$) haloalkyl, ($C_1$-$C_6$) alkoxy, ($C_1$-$C_6$) haloalkoxy, halogen, NO₂, NH₂, OH, or CN;
  $R_6'$ is CN, COOH, N(($C_1$-$C_6$) alkyl)-(CH₂)$_{1-4}$—N(($C_1$-$C_6$) alkyl)₂, ($C_1$-$C_6$) alkyl substituted with at least one OH, ($C_2$-$C_6$) alkenyl, $C_6$-$C_{10}$ aryl, heteroaryl comprising a 5- or 6-membered ring and 1-3 heteroatoms selected from N, O and S, or heterocyclyl comprising a 5- or 6-membered ring and 1-3 heteroatoms selected from N, O and S, wherein the ($C_2$-$C_6$) alkenyl, aryl, heteroaryl, and heterocyclyl are each optionally substituted with one or more Q-T;
  Q is a bond or ($C_1$-$C_6$) alkyl linker;
  T is ($C_1$-$C_6$) alkyl, ($C_1$-$C_6$) alkylamino, di($C_1$-$C_6$) alkylamino, amino, aminocarbonyl, ($C_1$-$C_6$) alkylaminocarbonyl, di($C_1$-$C_6$) alkylaminocarbonyl, OH, S(O)$_q$F, or heterocyclyl comprising a 5 or 6-membered ring and 1-3 heteroatoms selected from N, O and S, wherein when $R_6'$ is ($C_2$-$C_6$) alkenyl, T is not ($C_1$-$C_6$) alkyl;
  q is 1 or 2;
  m is 0, 1, 2, or 3; and
  n is 1, 2, or 3.

In some embodiments of Formula (Ia), each of $R_1$, $R_2$, $R_3$, $R_4$, $R_5$, Q, T, m, and n can be selected from the substituents as defined for $R_1$, $R_2$, $R_3$, $R_4$, $R_5$, Q, T, m, and n in Formula (I).

In some embodiments of Formula (Ia), m is as defined in (1a)-(1d) of Formula (I).

In some embodiments of Formula (Ia), $R_1$ is as defined in (2a)-(2e) of Formula (I).

In some embodiments of Formula (Ia), $R_2$ is as defined in (3a)-(3b) of Formula (I).

In some embodiments of Formula (Ia), $R_3$ is as defined in (4a)-(4d) and (6a)-(6b) of Formula (I).

In some embodiments of Formula (Ia), $R_4$ is as defined in (5a)-(5d) and (6a)-(6b) of Formula (I).

In some embodiments of Formula (Ia), n is as defined in (7a)-(7c) and (8g) of Formula (I).

In some embodiments of Formula (Ia), $R_5$ is as defined in (8a)-(8g) of Formula (I).

In some embodiments of Formula (Ia), Q is as defined in (10a)-(10b) of Formula (I).

In some embodiments of Formula (Ia), T is as defined in (11)-(11m) of Formula (I).

In some embodiments of Formula (Ia), $R_6'$ can be selected from the substituents as defined in (9)-(9m) for $R_6$ in Formula (I).

In some embodiments of Formula (Ia), $R_6'$ is heterocyclyl comprising a 6-membered ring and 1-3 heteroatoms selected from N, O and S (e.g., piperidinyl, tetrahydropyranyl, piperazinyl, morpholinyl, thiomorpholinyl, dioxanyl, etc.), optionally substituted with one or more Q-T. In some embodiments of Formula (Ia), $R_6'$ is heterocyclyl comprising a 5-membered ring and at least one nitrogen atom (e.g., piperidinyl, piperazinyl, morpholinyl, etc.), optionally substituted with one or more Q-T.

In some embodiments of Formula (Ia), each of the substituents defined for any one of $R_1$, $R_2$, $R_3$, $R_4$, $R_5$, $R_6'$, Q, T, q, m, and n can be combined with any of the substituents defined for the remainder of $R_1$, $R_2$, $R_3$, $R_4$, $R_5$, $R_6'$, Q, T, q, m, and n.

In some embodiments of Formula (Ia), $R_1$, $R_2$, $R_3$, $R_4$, $R_5$, q, m, and n can be combined as described in (12)-(38) in Formula (I), and $R_6'$ is as described above.

In some embodiments of Formula (Ia), $R_1$, $R_2$, $R_3$, $R_4$, $R_5$, $R_6'$, Q, T, q, m, and n can be combined as described above.

In some embodiments, a compound of Formula (Ia) is for inhibiting SRPK (e.g., SRPK1 and/or SRPK2), regulating (e.g., inhibiting) VEGF mediated angiogenesis, or treating or preventing AMD (e.g., in a subject identified in need of regulation (e.g., inhibition) of VEGF mediated angiogenesis for the treatment or prevention of AMD).

Another aspect of the application relates to a method of
inhibiting a mutant ALK (e.g., ALK G1202R);
treating or preventing a disease or disorder (e.g., cancer) in which a mutant ALK (e.g., ALK G1202R) plays a role;
treating or preventing cancer in a subject identified as being in need of inhibition of a mutant ALK (e.g., ALK G1202R) for the treatment or prevention of the cancer;
treating or preventing a disease or disorder (e.g., cancer) resistant to an ALK targeted therapy, such as a therapy with Alectinib (AF802), Ceritinib (LDK378), Brigatinib (AP26113), Crizotinib (Xalkori), and/or PF-06463922;
treating or preventing cancer, wherein the cancer cell comprises the mutant ALK (e.g., ALK G1202R);
inhibiting SRPK (e.g., SRPK1 and/or SRPK2);
regulating (e.g., inhibiting) VEGF mediated angiogenesis;
treating or preventing a disease or disorder in which a VEGF mediated angiogenesis plays a role (e.g., AMD or angiogenesis-dependent cancers);
treating or preventing AMD (e.g., in a subject identified in need of regulation (e.g., inhibition) of VEGF mediated angiogenesis for the treatment or prevention of AMD); or
treating or preventing an angiogenesis-dependent cancer (e.g., tumorous cancer) (e.g., in a subject identified in need of regulation of VEGF mediated angiogenesis for the treatment or prevention of an angiogenesis-dependent cancer), comprising administering to a subject in need thereof an effective amount of a compound of Formula (Ia), or a pharmaceutically acceptable salt, hydrate, solvate, prodrug, stereoisomer, or tautomer thereof.

In some embodiments, the application relates to a method of inhibiting SRPK (e.g., SRPK1 and/or SRPK2), regulating (e.g., inhibiting) VEGF mediated angiogenesis, or treating or preventing AMD (e.g., in a subject identified in need of regulation (e.g., inhibition) of VEGF mediated angiogenesis for the treatment or prevention of AMD).

In some embodiments, the application relates to a compound of Formula (Ia), of the following structure:

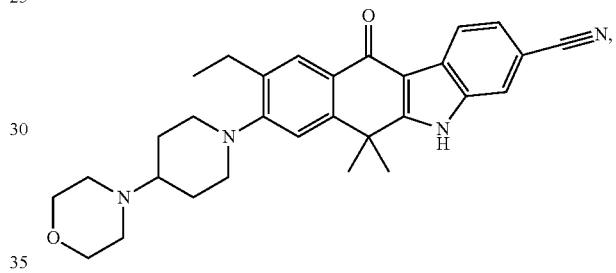

or a pharmaceutically acceptable salt, hydrate, solvate, prodrug, stereoisomer, or tautomer thereof, for
inhibiting a mutant ALK (e.g., ALK G1202R);
treating or preventing a disease or disorder (e.g., cancer) in which a mutant ALK (e.g., ALK G1202R) plays a role;
treating or preventing cancer in a subject identified as being in need of inhibition of a mutant ALK (e.g., ALK G1202R) for the treatment or prevention of the cancer;
treating or preventing a disease or disorder (e.g., cancer) resistant to an ALK targeted therapy, such as a therapy with Alectinib (AF802), Ceritinib (LDK378), Brigatinib (AP26113), Crizotinib (Xalkori), and/or PF-06463922;
treating or preventing cancer, wherein the cancer cell comprises the mutant ALK (e.g., ALK G1202R);
inhibiting SRPK (e.g., SRPK1 and/or SRPK2);
regulating (e.g., inhibiting) VEGF mediated angiogenesis;
treating or preventing a disease or disorder in which a VEGF mediated angiogenesis plays a role (e.g., AMD or angiogenesis-dependent cancers);
treating or preventing AMD (e.g., in a subject identified in need of regulation (e.g., inhibition) of VEGF mediated angiogenesis for the treatment or prevention of AMD); or
treating or preventing an angiogenesis-dependent cancer (e.g., tumorous cancer) (e.g., in a subject identified in need of regulation of VEGF mediated angiogenesis for the treatment or prevention of an angiogenesis-dependent cancer).

In some embodiments, the application relates to a compound of Formula (Ia), of the following structure:

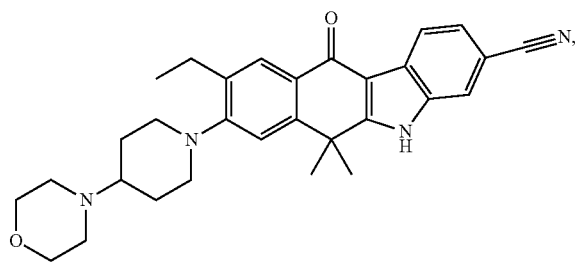 [SMILES: CCc1cc2c(cc1N1CCC(N3CCOCC3)CC1)C(C)(C)c1[nH]c3cc(C#N)ccc3c1C2=O]

or a pharmaceutically acceptable salt, hydrate, solvate, prodrug, stereoisomer, or tautomer thereof, for inhibiting SRPK (e.g., SRPK1 and/or SRPK2), regulating (e.g., inhibiting) VEGF mediated angiogenesis, or treating or preventing AMD (e.g., in a subject identified in need of regulation (e.g., inhibition) of VEGF mediated angiogenesis for the treatment or prevention of AMD).

Another aspect of the application relates to a method of inhibiting a mutant ALK (e.g., ALK G1202R);

treating or preventing a disease or disorder (e.g., cancer) in which a mutant ALK (e.g., ALK G1202R) plays a role;

treating or preventing cancer in a subject identified as being in need of inhibition of a mutant ALK (e.g., ALK G1202R) for the treatment or prevention of the cancer;

treating or preventing a disease or disorder (e.g., cancer) resistant to an ALK targeted therapy, such as a therapy with Alectinib (AF802), Ceritinib (LDK378), Brigatinib (AP26113), Crizotinib (Xalkori), and/or PF-06463922;

treating or preventing cancer, wherein the cancer cell comprises the mutant ALK (e.g., ALK G1202R);

inhibiting SRPK (e.g., SRPK1 and/or SRPK2);

regulating (e.g., inhibiting) VEGF mediated angiogenesis;

treating or preventing a disease or disorder in which a VEGF mediated angiogenesis plays a role (e.g., AMD or angiogenesis-dependent cancers);

treating or preventing AMD (e.g., in a subject identified in need of regulation (e.g., inhibition) of VEGF mediated angiogenesis for the treatment or prevention of AMD); or treating or preventing an angiogenesis-dependent cancer (e.g., tumorous cancer) (e.g., in a subject identified in need of regulation of VEGF mediated angiogenesis for the treatment or prevention of an angiogenesis-dependent cancer), comprising administering to a subject in need thereof an effective amount of a compound of the following structure:

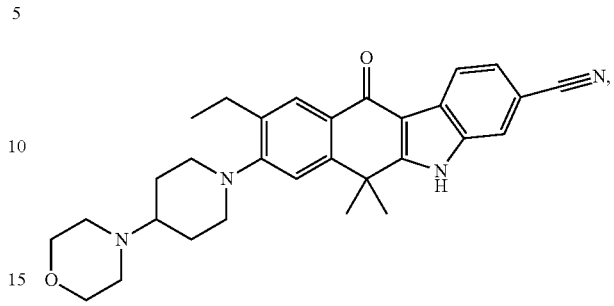

or a pharmaceutically acceptable salt, hydrate, solvate, prodrug, stereoisomer, or tautomer thereof.

In some embodiments, the application relates to a method of inhibiting SRPK (e.g., SRPK1 and/or SRPK2), regulating (e.g., inhibiting) VEGF mediated angiogenesis, or treating or preventing AMD (e.g., in a subject identified in need of regulation (e.g., inhibition) of VEGF mediated angiogenesis for the treatment or prevention of AMD), comprising administering to a subject in need thereof an effective amount of a compound of the following structure:

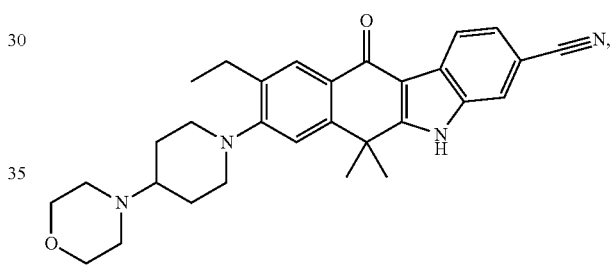

or a pharmaceutically acceptable salt, hydrate, solvate, prodrug, stereoisomer, or tautomer thereof.

Non-limiting illustrative compounds of the application include:

| Cmpd No. | Structure | Compound Name |
|---|---|---|
| 6 | 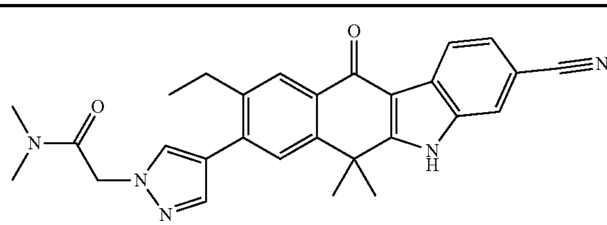 | 2-(4-(3-cyano-9-ethyl-6,6-dimethyl-11-oxo-6,11-dihydro-5H-benzo[b]carbazol-8-yl)-1H-pyrazol-1-yl)-N,N-dimethylacetamide |
| 7 | 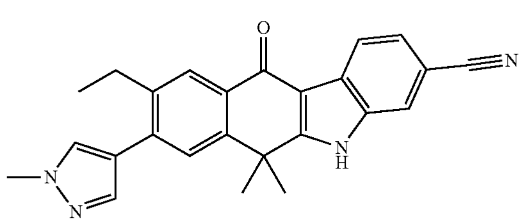 [SMILES: CCc1cc2c(cc1-c1cnn(C)c1)C(C)(C)c1[nH]c3cc(C#N)ccc3c1C2=O] | 9-ethyl-6,6-dimethyl-8-(1-methyl-1H-pyrazol-4-yl)-11-oxo-6,11-dihydro-5H-benzo[b]carbazole-3-carbonitrile |

-continued

| Cmpd No. | Structure | Compound Name |
|---|---|---|
| 8 | 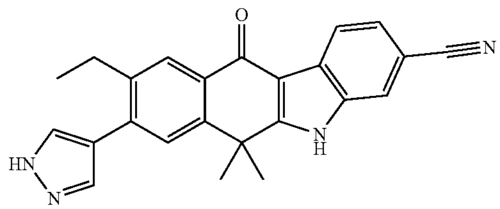 [SMILES: CCc1cc2c(cc1-c1cn[nH]c1)C(C)(C)c1[nH]c3cc(C#N)ccc3c1C2=O] | 9-ethyl-6,6-dimethyl-11-oxo-8-(1H-pyrazol-4-yl)-6,11-dihydro-5H-benzo[b]carbazole-3-carbonitrile |
| 9 | 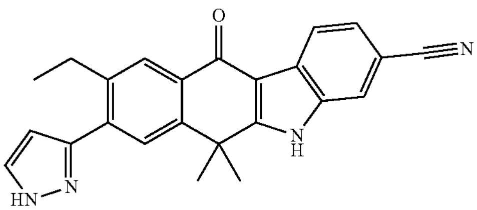 [SMILES: CCc1cc2c(cc1-c1cc[nH]n1)C(C)(C)c1[nH]c3cc(C#N)ccc3c1C2=O] | 9-ethyl-6,6-dimethyl-11-oxo-8-(1H-pyrazol-3-yl)-6,11-dihydro-5H-benzo[b]carbazole-3-carbonitrile |
| 10 | 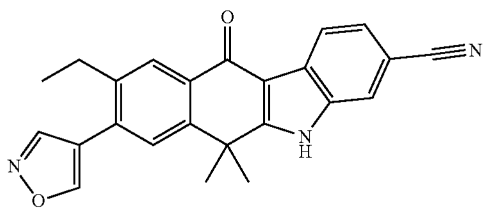 [SMILES: CCc1cc2c(cc1-c1cnoc1)C(C)(C)c1[nH]c3cc(C#N)ccc3c1C2=O] | 9-ethyl-8-(isoxazol-4-yl)-6,6-dimethyl-11-oxo-6,11-dihydro-5H-benzo[b]carbazole-3-carbonitrile |
| 11 | 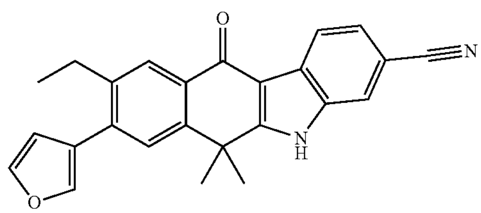 [SMILES: CCc1cc2c(cc1-c1ccoc1)C(C)(C)c1[nH]c3cc(C#N)ccc3c1C2=O] | 9-ethyl-8-(furan-3-yl)-6,6-dimethyl-11-oxo-6,11-dihydro-5H-benzo[b]carbazole-3-carbonitrile |
| 12 | 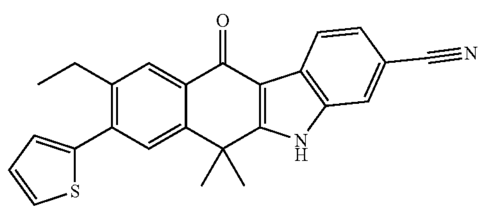 [SMILES: CCc1cc2c(cc1-c1cccs1)C(C)(C)c1[nH]c3cc(C#N)ccc3c1C2=O] | 9-ethyl-6,6-dimethyl-11-oxo-8-(thiophen-2-yl)-6,11-dihydro-5H-benzo[b]carbazole-3-carbonitrile |
| 13 | 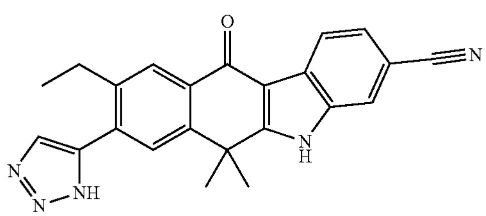 [SMILES: CCc1cc2c(cc1-c1cnn[nH]1)C(C)(C)c1[nH]c3cc(C#N)ccc3c1C2=O] | 9-ethyl-6,6-dimethyl-11-oxo-8-(1H-1,2,3-triazol-5-yl)-6,11-dihydro-5H-benzo[b]carbazole-3-carbonitrile |
| 14 | 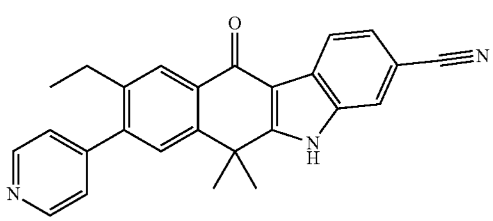 [SMILES: CCc1cc2c(cc1-c1ccncc1)C(C)(C)c1[nH]c3cc(C#N)ccc3c1C2=O] | (9-ethyl-6,6-dimethyl-11-oxo-8-(pyridin-4-yl)-6,11-dihydro-5H-benzo[b]carbazole-3-carbonitrile |

-continued

| Cmpd No. | Structure | Compound Name |
|---|---|---|
| 15 | 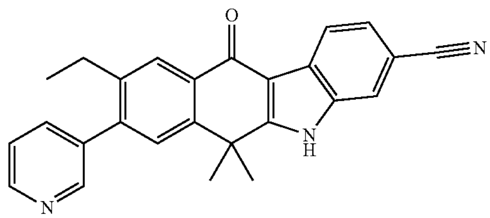 [SMILES: CCc1cc2c(cc1-c1cccnc1)C(C)(C)c1[nH]c3cc(C#N)ccc3c1C2=O] | 9-ethyl-6,6-dimethyl-11-oxo-8-(pyridin-3-yl)-6,11-dihydro-5H-benzo[b]carbazole-3-carbonitrile |
| 16 | 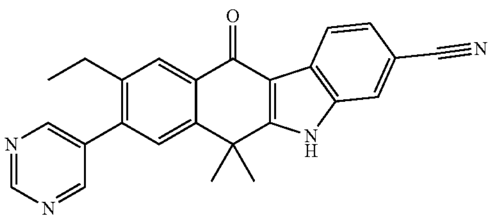 [SMILES: CCc1cc2c(cc1-c1cncnc1)C(C)(C)c1[nH]c3cc(C#N)ccc3c1C2=O] | 9-ethyl-6,6-dimethyl-11-oxo-8-(pyrimidin-5-yl)-6,11-dihydro-5H-benzo[b]carbazole-3-carbonitrile |
| 17 | 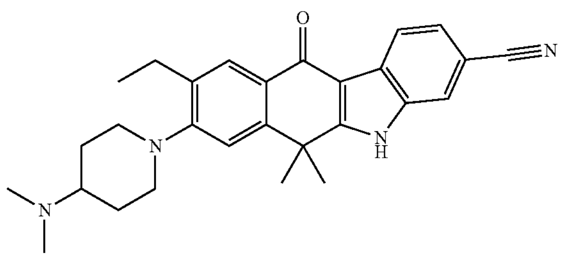 [SMILES: CCc1cc2c(cc1N1CCC(N(C)C)CC1)C(C)(C)c1[nH]c3cc(C#N)ccc3c1C2=O] | 8-(4-(dimethylamino)piperidin-1-yl)-9-ethyl-6,6-dimethyl-11-oxo-6,11-dihydro-5H-benzo[b]carbazole-3-carbonitrile |
| 18 | 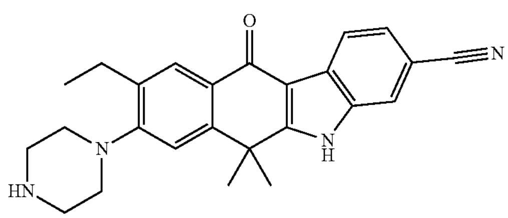 [SMILES: CCc1cc2c(cc1N1CCNCC1)C(C)(C)c1[nH]c3cc(C#N)ccc3c1C2=O] | 9-ethyl-6,6-dimethyl-11-oxo-8-(piperazin-1-yl)-6,11-dihydro-5H-benzo[b]carbazole-3-carbonitrile |
| 19 | 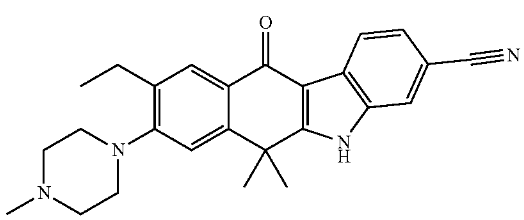 [SMILES: CCc1cc2c(cc1N1CCN(C)CC1)C(C)(C)c1[nH]c3cc(C#N)ccc3c1C2=O] | 9-ethyl-6,6-dimethyl-8-(4-methylpiperazin-1-yl)-11-oxo-6,11-dihydro-5H-benzo[b]carbazole-3-carbonitrile |
| 20 | 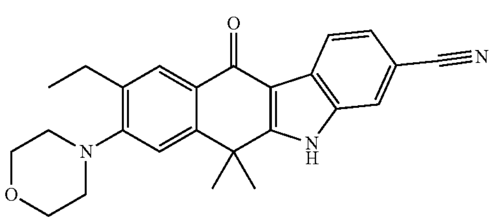 [SMILES: CCc1cc2c(cc1N1CCOCC1)C(C)(C)c1[nH]c3cc(C#N)ccc3c1C2=O] | 9-ethyl-6,6-dimethyl-8-morpholino-11-oxo-6,11-dihydro-5H-benzo[b]carbazole-3-carbonitrile |
| 21 | 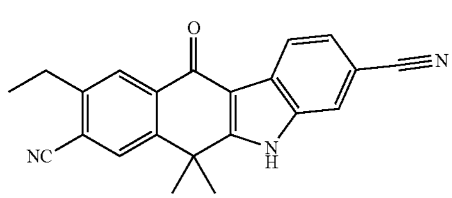 [SMILES: CCc1cc2c(cc1C#N)C(C)(C)c1[nH]c3cc(C#N)ccc3c1C2=O] | 9-ethyl-6,6-dimethyl-11-oxo-6,11-dihydro-5H-benzo[b]carbazole-3,8-dicarbonitrile |

-continued

| Cmpd No. | Structure | Compound Name |
|---|---|---|
| 22 | 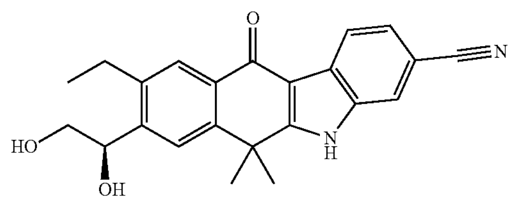 [SMILES: CCc1cc2c(cc1[C@@H](O)CO)C(C)(C)c1[nH]c3cc(C#N)ccc3c1C2=O] | (R)-8-(1,2-dihydroxyethyl)-9-ethyl-6,6-dimethyl-11-oxo-6,11-dihydro-5H-benzo[b]carbazole-3-carbonitrile |
| 23 | 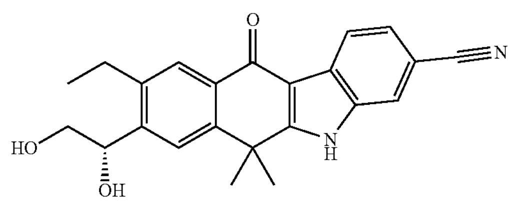 [SMILES: CCc1cc2c(cc1[C@H](O)CO)C(C)(C)c1[nH]c3cc(C#N)ccc3c1C2=O] | (S)-8-(1,2-dihydroxyethyl)-9-ethyl-6,6-dimethyl-11-oxo-6,11-dihydro-5H-benzo[b]carbazole-3-carbonitrile |
| 24 | 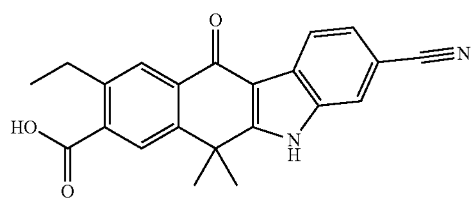 [SMILES: CCc1cc2c(cc1C(=O)O)C(C)(C)c1[nH]c3cc(C#N)ccc3c1C2=O] | 3-cyano-9-ethyl-6,6-dimethyl-11-oxo-6,11-dihydro-5H-benzo[b]carbazole-8-carboxylic acid |
| 25 | 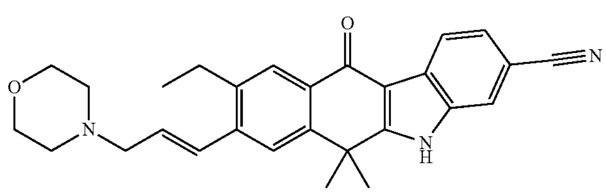 [SMILES: CCc1cc2c(cc1/C=C/CN1CCOCC1)C(C)(C)c1[nH]c3cc(C#N)ccc3c1C2=O] | (E)-9-ethyl-6,6-dimethyl-8-(3-morpholinoprop-1-en-1-yl)-11-oxo-6,11-dihydro-5H-benzo[b]carbazole-3-carbonitrile |
| 26 | 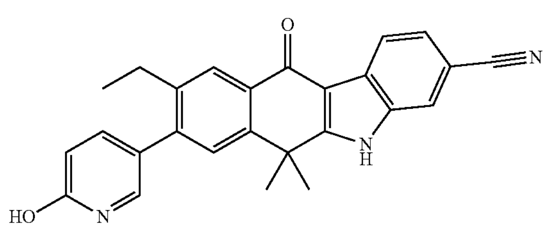 [SMILES: CCc1cc2c(cc1-c1ccc(O)nc1)C(C)(C)c1[nH]c3cc(C#N)ccc3c1C2=O] | 9-ethyl-8-(6-hydroxypyridin-3-yl)-6,6-dimethyl-11-oxo-6,11-dihydro-5H-benzo[b]carbazole-3-carbonitrile |
| 27 | 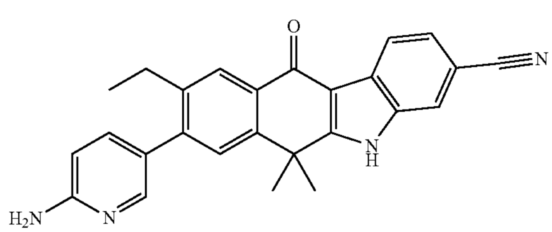 [SMILES: CCc1cc2c(cc1-c1ccc(N)nc1)C(C)(C)c1[nH]c3cc(C#N)ccc3c1C2=O] | 8-(6-aminopyridin-3-yl)-9-ethyl-6,6-dimethyl-11-oxo-6,11-dihydro-5H-benzo[b]carbazole-3-carbonitrile |
| 28 | 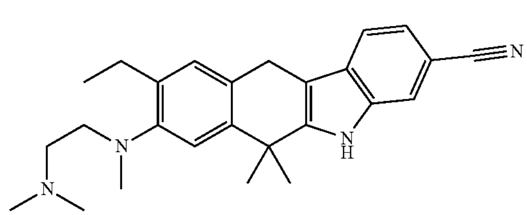 [SMILES: CCc1cc2c(cc1N(C)CCN(C)C)C(C)(C)c1[nH]c3cc(C#N)ccc3c1C2] | 8-((2 (dimethylamino)ethyl)(methyl)amino)-9-ethyl-6,6-dimethyl-11-oxo-6,11-dihydro-5H-benzo[b]carbazole-3-carbonitrile |

-continued

| Cmpd No. | Structure | Compound Name |
|---|---|---|
| 29 | 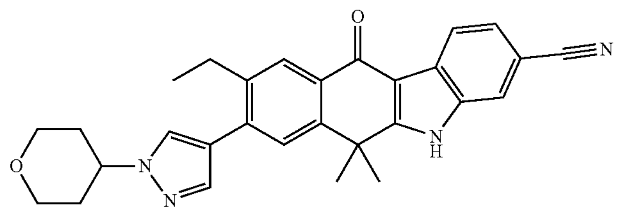 [SMILES: CCc1cc2c(cc1-c1cnn(C3CCOCC3)c1)C(C)(C)c1[nH]c3cc(C#N)ccc3c1C2=O] | 9-ethyl-6,6-dimethyl-11-oxo-8-(1-(tetrahydro-2H-pyran-4-yl)-1H-pyrazol-4-yl)-6,11-dihydro-5H-benzo[b]carbazole-3-carbonitrile |
| 30 | 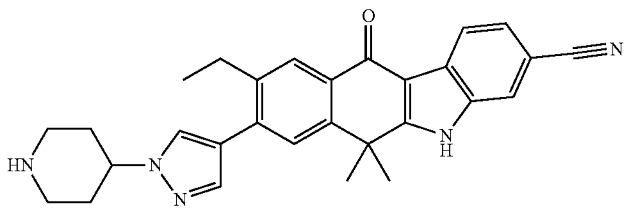 [SMILES: CCc1cc2c(cc1-c1cnn(C3CCNCC3)c1)C(C)(C)c1[nH]c3cc(C#N)ccc3c1C2=O] | 9-ethyl-6,6-dimethyl-11-oxo-8-(1-(piperidin-4-yl)-1H-pyrazol-4-yl)-6,11-dihydro-5H-benzo[b]carbazole-3-carbonitrile |
| 31 | 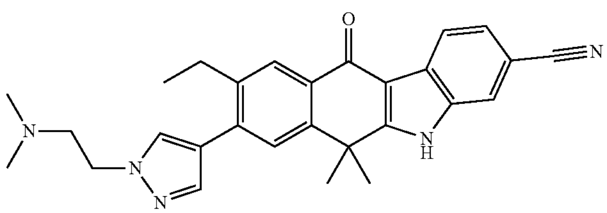 [SMILES: CCc1cc2c(cc1-c1cnn(CCN(C)C)c1)C(C)(C)c1[nH]c3cc(C#N)ccc3c1C2=O] | 8-(1-(2-(dimethylamino)ethyl)-1H-pyrazol-4-yl)-9-ethyl-6,6-dimethyl-11-oxo-6,11-dihydro-5H-benzo[b]carbazole-3-carbonitrile |
| 32 | 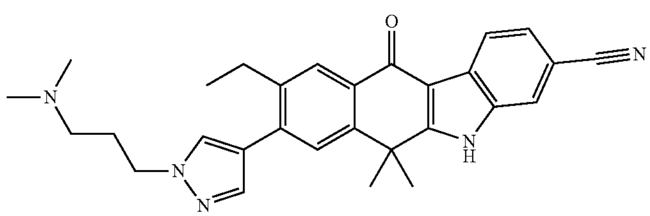 [SMILES: CCc1cc2c(cc1-c1cnn(CCCN(C)C)c1)C(C)(C)c1[nH]c3cc(C#N)ccc3c1C2=O] | 8-(1-(3-(dimethylamino)propyl)-1H-pyrazol-4-yl)-9-ethyl-6,6-dimethyl-11-oxo-6,11-dihydro-5H-benzo[b]carbazole-3-carbonitrile |
| 33 | 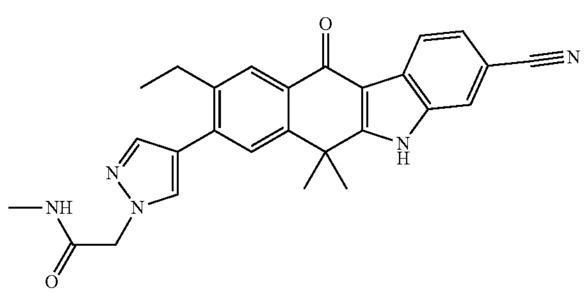 [SMILES: CCc1cc2c(cc1-c1cnn(CC(=O)NC)c1)C(C)(C)c1[nH]c3cc(C#N)ccc3c1C2=O] | 2-(4-(3-cyano-9-ethyl-6,6-dimethyl-11-oxo-6,11-dihydro-5H-benzo[b]carbazol-8-yl)-1H-pyrazol-1-yl)-N-methylacetamide |
| 34 | 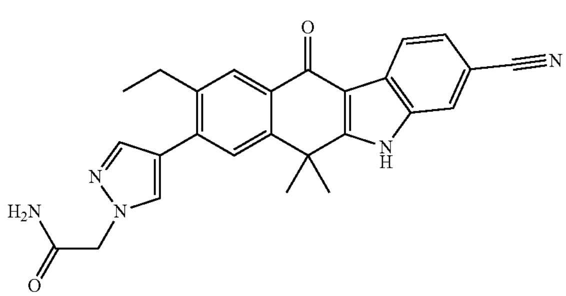 [SMILES: CCc1cc2c(cc1-c1cnn(CC(N)=O)c1)C(C)(C)c1[nH]c3cc(C#N)ccc3c1C2=O] | 2-(4-(3-cyano-9-ethyl-6,6-dimethyl-11-oxo-6,11-dihydro-5H-benzo[b]carbazol-8-yl)-1H-pyrazol-1-yl)acetamide |

-continued

| Cmpd No. | Structure | Compound Name |
|---|---|---|
| 35 | 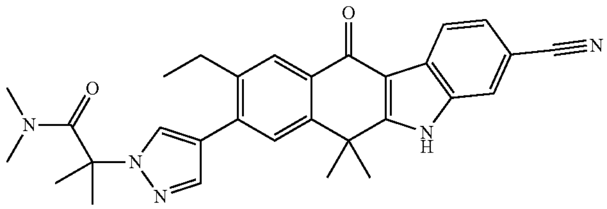 [SMILES: CCc1cc2c(cc1-c1cnn(C(C)(C)C(=O)N(C)C)c1)C(C)(C)c1[nH]c3cc(C#N)ccc3c1C2=O] | 2-(4-(3-cyano-9-ethyl-6,6-dimethyl-11-oxo-6,11-dihydro-5H-benzo[b]carbazol-8-yl)-1H-pyrazol-1-yl)-N,N,2-trimethylpropanamide |
| 36 | 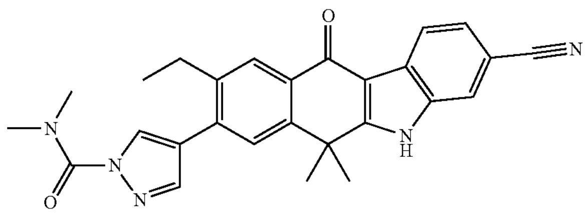 [SMILES: CCc1cc2c(cc1-c1cnn(C(=O)N(C)C)c1)C(C)(C)c1[nH]c3cc(C#N)ccc3c1C2=O] | 4-(3-cyano-9-ethyl-6,6-dimethyl-11-oxo-6,11-dihydro-5H-benzo[b]carbazol-8-yl)-N,N-dimethyl-1H-pyrazole-1-carboxamide |
| 37 | 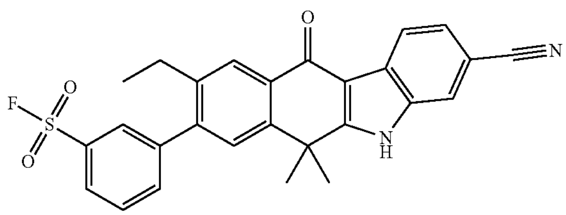 [SMILES: CCc1cc2c(cc1-c1cccc(S(=O)(=O)F)c1)C(C)(C)c1[nH]c3cc(C#N)ccc3c1C2=O] | 3-(3-cyano-9-ethyl-6,6-dimethyl-11-oxo-6,11-dihydro-5H-benzo[b]carbazol-8-yl)benzenesulfonyl fluoride |
| 38 | 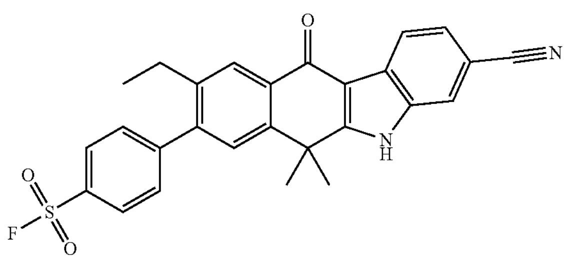 [SMILES: CCc1cc2c(cc1-c1ccc(S(=O)(=O)F)cc1)C(C)(C)c1[nH]c3cc(C#N)ccc3c1C2=O] | 4-(3-cyano-9-ethyl-6,6-dimethyl-11-oxo-6,11-dihydro-5H-benzo[b]carbazol-8-yl)benzenesulfonyl fluoride |

A compound of the present application is capable of binding to the ATP binding site in ALK. In some embodiments, a compound of the present application is capable of binding to the ATP binding site in a wild-type ALK. In some embodiments, a compound of the present application is capable of binding to the ATP binding site in ALK comprising one or more mutations. In some embodiments, a compound of the present application is capable of modulating (e.g., inhibiting or decreasing) the activity of a wild-type ALK and/or ALK comprising one or more mutations. In some embodiments, the mutant ALK comprises one or more mutations selected from C1156Y, F1174L, L1196M, L1152R, 1151 Tins, G1202R, G1269A, and S1206Y. In some embodiments, the mutant ALK comprises at least the mutation G1202R, optionally in combination with one or more other ALK mutations (e.g., C1156Y, F1174L, L1196M, L1152R, 1151 Tins, G1269A, and S1206Y). In further embodiments, a compound of the present application is capable of modulating (e.g., inhibiting or decreasing) the activity of a wild-type ALK and/or an ALK mutant comprising one or more mutations selected from C1156Y, F1174L, L1196M, L1152R, 1151 Tins, G1202R, G1269A, and S1206Y. In further embodiments, a compound of the present application is capable of modulating (e.g., inhibiting or decreasing) the activity of a wild-type ALK and/or a mutant ALK comprising at least the mutation G1202R, optionally in combination with one or more other ALK mutations (e.g., C1156Y, F1174L, L1196M, L1152R, 1151 Tins, G1269A, and S1206Y).

In some embodiments, a compound of the present application is capable of modulating (e.g., inhibiting or decreasing) the activity of SRPK (e.g., SRPK1 and/or SRPK2). In still further embodiments, modulation of SRPK (e.g., SRPK1 and/or SRPK2) activity may regulate VEGF mediated angiogenesis.

In some embodiments, the inhibition of SRPK (e.g., SRPK1 and/or SRPK2), ALK and ALK mutants by a compound of the present application is measured by $IC_{50}$.

In some embodiments, the inhibition of SRPK (e.g., SRPK1 and/or SRPK2), ALK and ALK mutants by a compound of the present application is measured by $EC_{50}$.

Potency of the inhibitor can be determined by $EC_{50}$ value. A compound with a lower $EC_{50}$ value, as determined under substantially similar conditions, is a more potent inhibitor relative to a compound with a higher $EC_{50}$ value. In some embodiments, the substantially similar conditions comprise determining an ALK-dependent phosphorylation level, in vitro or in vivo (e.g., in $Ba/F_3$ cells or a tumor cell transduced with a wild-type ALK, a mutant ALK, or a fragment of thereof). In some embodiments, the substantially similar conditions comprise determining an SRPK (e.g., SRPK1 and/or SRPK2)-dependent phosphorylation level, in vitro or in vivo.

Potency of the inhibitor can also be determined by $IC_{50}$ value. A compound with a lower $IC_{50}$ value, as determined under substantially similar conditions, is a more potent inhibitor relative to a compound with a higher $IC_{50}$ value. In some embodiments, the substantially similar conditions comprise determining an ALK-dependent phosphorylation level, in vitro or in vivo (e.g., in Ba/$F_3$ cells or a tumor cell transduced with a wild-type ALK, a mutant ALK, or a fragment of thereof). In some embodiments, the substantially similar conditions comprise determining an SRPK (e.g., SRPK1 and/or SRPK2)-dependent phosphorylation level, in vitro or in vivo.

The inhibition of wild-type ALK and ALK comprising one or more mutations by a compound of the present application can also be measured using cellular proliferation assays where cell proliferation is dependent on kinase activity. For example, Ba/$F_3$ cells or cancer cell lines (e.g., NSCLC) transfected with a wild-type ALK, or an ALK mutant comprising one or more mutations selected from C1156Y, F1174L, L1196M, L1152R, 1151 Tins, G1202R, G1269A, and S1206Y can be used. Proliferation assays are performed at a range of inhibitor concentrations and $EC_{50}$'s or $IC_{50}$'s are calculated.

An alternative method to measure effects on ALK activity is to assay ALK phosphorylation. For example, a wild-type ALK or mutant ALK (e.g., C1156Y, F1174L, L1196M, L1152R, 1151 Tins, G1202R, G1269A, and/or S1206Y) can be transfected into Ba/$F_3$ cells or cancer cell lines (e.g., NSCLC) (which may or may not normally express endogenous ALK), and the ability of the inhibitor to inhibit ALK phosphorylation can be assayed. The effects on ALK phosphorylation can be measured by Western blotting using phospho-specific ALK antibodies.

The inhibition of SRPK (e.g., SRPK1 and/or SRPK2) by a compound of the present application can also be measured using cell vascularization assays (e.g., choroid neovasculariation assay) where vascularization is dependent on SRPK (e.g., SRPK1 and/or SRPK2) activity. Alternatively, The inhibition of SRPK (e.g., SRPK1 and/or SRPK2) by a compound of the present application can also be evaluated by measuring VEGF splicing.

In some embodiments, a compound of the application exhibits greater inhibition of ALK comprising one or more mutations as described herein relative to a wild-type ALK. In certain embodiments, a compound of the application exhibits at least 2-fold, 3-fold, 5-fold, 10-fold, 25-fold, 50-fold or 100-fold greater inhibition of ALK comprising one or more mutations as described herein relative to a wild-type ALK.

In some embodiments, a compound of present application is more potent than one or more known ALK inhibitors, including but not limited to, Alectinib (AF802), Ceritinib (LDK378), Brigatinib (AP26113), Crizotinib (Xalkori), and/or PF-06463922, at inhibiting the activity of a wild-type ALK. For example, the compounds can be at least about 2-fold, about 3-fold, about 5-fold, about 10-fold, about 25-fold, about 50-fold or about 100-fold more potent (e.g., as measured by $IC_{50}$) than Alectinib, Ceritinib, Brigatinib, Crizotinib, and/or PF-06463922, at inhibiting the activity of a wild-type ALK.

In some embodiments, a compound of present application is more potent than one or more known ALK inhibitors, including but not limited to, Alectinib (AF802), Ceritinib (LDK378), Brigatinib (AP26113), Crizotinib (Xalkori), and/or PF-06463922, at inhibiting the activity of ALK comprising one or more mutations as described herein. For example, the compounds can be at least about 2-fold, about 3-fold, about 5-fold, about 10-fold, about 25-fold, about 50-fold or about 100-fold more potent (e.g., as measured by $IC_{50}$) than Alectinib, Ceritinib, Brigatinib, Crizotinib, and/or PF-06463922, at inhibiting the activity of ALK comprising one or more mutations as described herein.

In some embodiments, a compound of present application is more potent than one or more known ALK inhibitors, including but not limited to, Alectinib (AF802), Ceritinib (LDK378), Brigatinib (AP26113), Crizotinib (Xalkori), and/or PF-06463922, at inhibiting the activity of ALK containing at least the G1202R mutation. For example, the compounds can be at least about 2-fold, about 3-fold, about 5-fold, about 10-fold, about 25-fold, about 50-fold or about 100-fold more potent (e.g., as measured by $IC_{50}$) than Alectinib, Ceritinib, Brigatinib, Crizotinib, and/or PF-06463922, at inhibiting the activity of ALK containing at least the G1202R mutation.

In some embodiments, a compound of present application is more potent at inhibiting the activity of ALK comprising one or more mutations as described herein, but less potent at inhibiting the activity of a wild-type ALK, than one or more known ALK inhibitors, including but not limited to, Alectinib (AF802), Ceritinib (LDK378), Brigatinib (AP26113), Crizotinib (Xalkori), and/or PF-06463922. For example, the compounds can be at least about 2-fold, about 3-fold, about 5-fold, about 10-fold, about 25-fold, about 50-fold or about 100-fold more potent (e.g., as measured by $IC_{50}$) at inhibiting the activity of ALK comprising one or more mutations as described herein, but at least about 2-fold, about 3-fold, about 5-fold, about 10-fold, about 25-fold, about 50-fold or about 100-fold less potent (e.g., as measured by $IC_{50}$) at inhibiting the activity of a wild-type ALK, than Alectinib, Ceritinib, Brigatinib, Crizotinib, and/or PF-06463922.

In some embodiments, a compound of present application is more potent at inhibiting the activity of ALK containing at least the G1202R mutation, but less potent at inhibiting the activity of a wild-type ALK, than one or more known ALK inhibitors, including but not limited to, Alectinib (AF802), Ceritinib (LDK378), Brigatinib (AP26113), Crizotinib (Xalkori), and/or PF-06463922. For example, the compounds can be at least about 2-fold, about 3-fold, about 5-fold, about 10-fold, about 25-fold, about 50-fold or about 100-fold more potent (e.g., as measured by $IC_{50}$) at inhibiting the activity of ALK containing at least the G1202R mutation, but at least about 2-fold, about 3-fold, about 5-fold, about 10-fold, about 25-fold, about 50-fold or about 100-fold less potent (e.g., as measured by $IC_{50}$) at inhibiting the activity of a wild-type ALK, than Alectinib, Ceritinib, Brigatinib, Crizotinib, and/or PF-06463922.

In some embodiments, a compound of present application is more potent at inhibiting the activity of ALK comprising one or more mutations as described herein, and more potent at inhibiting the activity of a wild-type ALK, than one or more known ALK inhibitors, including but not limited to, Alectinib (AF802), Ceritinib (LDK378), Brigatinib (AP26113), Crizotinib (Xalkori), and/or PF-06463922. For example, the compounds can be at least about 2-fold, about 3-fold, about 5-fold, about 10-fold, about 25-fold, about 50-fold or about 100-fold more potent (e.g., as measured by $IC_{50}$) at inhibiting the activity of ALK comprising one or more mutations as described herein, and at least about 2-fold, about 3-fold, about 5-fold, about 10-fold, about 25-fold, about 50-fold or about 100-fold more potent (e.g., as measured by $IC_{50}$) at inhibiting the activity of a wild-type ALK, than Alectinib, Ceritinib, Brigatinib, Crizotinib, and/or PF-06463922.

In some embodiments, a compound of present application is more potent at inhibiting the activity of ALK containing at least the G1202R mutation, and more potent at inhibiting the activity of a wild-type ALK, than one or more known ALK inhibitors, including but not limited to, Alectinib (AF802), Ceritinib (LDK378), Brigatinib (AP26113), Crizotinib (Xalkori), and/or PF-06463922. For example, the compounds can be at least about 2-fold, about 3-fold, about 5-fold, about 10-fold, about 25-fold, about 50-fold or about 100-fold more potent (e.g., as measured by $IC_{50}$) at inhibiting the activity of ALK containing at least the G1202R mutation, and at least about 2-fold, 3-fold, 5-fold, 10-fold, 25-fold, 50-fold or about 100-fold more potent (e.g., as measured by $IC_{50}$) at inhibiting the activity of a wild-type ALK, than Alectinib, Ceritinib, Brigatinib, Crizotinib, and/or PF-06463922.

In some embodiments, a compound of the application displays high brain exposure (or brain permeability). Brain exposure can be measured by various methods known in the art. For example, brain exposure can be measured by calculating the ratio between the concentration of a compound of the application in the brain and the concentration of the compound in the plasma (i.e., B:P ratio). In some embodiments, a compound of the application has a B:P ratio of at least 0.1, 0.2, 0.3, 0.4, 0.5, 0.6, 0.7, 0.8, 0.9, or 1.0 at 2 hours after administration of the compound to a subject.

In some embodiments, a compound of the application displays higher brain exposure than one or more known ALK inhibitors, including but not limited to, Alectinib (AF802), Ceritinib (LDK378), Brigatinib (AP26113), Crizotinib (Xalkori), and/or PF-06463922. In some embodiments, a compound of the application has a B:P ratio that is at least about 2-fold, 3-fold, 5-fold, 10-fold, 25-fold, 50-fold or about 100-fold of the B:P ratio of one or more known ALK inhibitors.

Definitions

Listed below are definitions of various terms used to describe this application. These definitions apply to the terms as they are used throughout this specification and claims, unless otherwise limited in specific instances, either individually or as part of a larger group.

The term "alkyl," as used herein, refers to saturated, straight- or branched-chain hydrocarbon radicals containing, in certain embodiments, between one and six, or one and eight carbon atoms, respectively. Examples of $C_1$-$C_6$ alkyl radicals include, but are not limited to, methyl, ethyl, propyl, isopropyl, n-butyl, tert-butyl, neopentyl, n-hexyl radicals; and examples of $C_1$-$C_8$ alkyl radicals include, but are not limited to, methyl, ethyl, propyl, isopropyl, n-butyl, tert-butyl, neopentyl, n-hexyl, heptyl, octyl radicals.

The term "alkenyl," as used herein, denotes a monovalent group derived from a hydrocarbon moiety containing, in certain embodiments, from two to six, or two to eight carbon atoms having at least one carbon-carbon double bond. The double bond may or may not be the point of attachment to another group. Alkenyl groups include, but are not limited to, for example, ethenyl, propenyl, butenyl, 1-methyl-2-buten-1-yl, heptenyl, octenyl and the like.

The term "alkoxy" refers to an —O-alkyl radical.

The term "heteroaryl," as used herein, refers to a mono- or poly-cyclic (e.g., bi-, or tri-cyclic or more) fused or non-fused, radical or ring system having at least one aromatic ring, having from five to ten ring atoms of which at least one ring atom is selected from S, O, and N; zero, one, or two ring atoms are additional heteroatoms independently selected from S, O, and N; and the remaining ring atoms are carbon. Heteroaryl includes, but is not limited to, pyridinyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, isoquinolinyl, benzimidazolyl, benzooxazolyl, quinoxalinyl, and the like.

In accordance with the application, any of the heteroaryls and substituted heteroaryls described herein, can be any aromatic group. Aromatic groups can be substituted or unsubstituted.

The term "heterocyclyl," as used herein, refers to a non-aromatic 3-, 4-, 5-, 6- or 7-membered ring or a bi- or tri-cyclic group fused of non-fused system, where (i) each ring contains between one and three heteroatoms independently selected from oxygen, sulfur and nitrogen, (ii) each 5-membered ring has 0 to 1 double bonds and each 6-membered ring has 0 to 2 double bonds, (iii) the nitrogen and sulfur heteroatoms may optionally be oxidized, and (iv) the nitrogen heteroatom may optionally be quaternized. Representative heterocyclyl groups include, but are not limited to, [1,3]dioxolane, pyrrolidinyl, pyrazolinyl, pyrazolidinyl, imidazolinyl, imidazolidinyl, piperidinyl, piperazinyl, oxazolidinyl, isoxazolidinyl, morpholinyl, thiazolidinyl, isothiazolidinyl, and tetrahydrofuryl.

The term "alkylamino" refers to a group having the structure —NH($C_1$-$C_{12}$ alkyl), e.g., —NH($C_1$-$C_6$ alkyl), where $C_1$-$C_6$ alkyl is as previously defined.

The term "dialkylamino" refers to a group having the structure —N($C_1$-$C_{12}$alkyl)$_2$, e.g., —N($C_1$-$C_6$ alkyl)$_2$, where $C_1$-$C_6$ alkyl is as previously defined.

The terms "hal," "halo," and "halogen," as used herein, refer to an atom selected from fluorine, chlorine, bromine, and iodine.

The term "alkyl linker" is intended to include $C_1$, $C_2$, $C_3$, $C_4$, $C_5$ or $C_6$ straight chain (linear) saturated aliphatic hydrocarbon groups and $C_3$, $C_4$, $C_5$ or $C_6$ branched saturated aliphatic hydrocarbon groups. For example, $C_1$-$C_6$ alkyl linker is intended to include $C_1$, $C_2$, $C_3$, $C_4$, $C_5$ and $C_6$ alkyl linker groups. Examples of alkyl linker include, moieties having from one to six carbon atoms, such as, but not limited to, methyl linker (—$CH_2$—), ethyl linker (—$CH_2CH_2$— or —CH($CH_3$)—), propyl linker (—$CH_2CH_2CH_2$—, —CH($CH_3$)$CH_2$—, or —C($CH_3$)$_2$—), butyl linker (—$CH_2CH_2CH_2CH_2$—, —CH($CH_3$)$CH_2CH_2$—, —$CH_2$CH($CH_3$)$CH_2$—, —C($CH_3$) 2$CH_2$—, or —CH($CH_3$)CH($CH_3$)—), pentyl linker (—$CH_2CH_2CH_2CH_2CH_2$—, —CH($CH_3$)$CH_2CH_2CH_2$—, —$CH_2$CH($CH_3$)$CH_2CH_2$—, —C($CH_3$)$_2CH_2CH_2$—, or —$CH_2$C($CH_3$)$_2CH_2$—), and hexyl linker (—$CH_2CH_2CH_2CH_2CH_2CH_2$—).

As described herein, a compound of the application may optionally be substituted with one or more substituents, such as are illustrated generally above, or as exemplified by particular classes, subclasses, and species of the application. It will be appreciated that the phrase "optionally substituted" is used interchangeably with the phrase "substituted or unsubstituted." In general, the term "substituted", whether preceded by the term "optionally" or not, refers to the replacement of hydrogen in a given structure with the radical of a specified substituent. Unless otherwise indicated, an optionally substituted group may have a substituent at each substitutable position of the group, and when more than one position in any given structure may be substituted with more than one substituent selected from a specified group, and the substituent may be either the same or different at every position.

It is understood that the aryls, heteroaryls, alkyls, and the like can be substituted.

The term "cancer" includes, but is not limited to, the following cancers: epidermoid Oral: buccal cavity, lip, tongue, mouth, pharynx; Cardiac: sarcoma (angiosarcoma, fibrosarcoma, rhabdomyosarcoma, liposarcoma), myxoma, rhabdomyoma, fibroma, lipoma, and teratoma; Lung: bronchogenic carcinoma (squamous cell or epidermoid, undifferentiated small cell, undifferentiated large cell, adenocarcinoma), alveolar (bronchiolar) carcinoma, bronchial adenoma, sarcoma, lymphoma, chondromatous hamartoma, mesothelioma; Gastrointestinal: esophagus (squamous cell carcinoma, larynx, adenocarcinoma, leiomyosarcoma, lymphoma), stomach (carcinoma, lymphoma, leiomyosarcoma), pancreas (ductal adenocarcinoma, insulinoma, glucagonoma, gastrinoma, carcinoid tumors, vipoma), small bowel or small intestines (adenocarcinoma, lymphoma, carcinoid tumors, Karposi's sarcoma, leiomyoma, hemangioma, lipoma, neurofibroma, fibroma), large bowel or large intestines (adenocarcinoma, tubular adenoma, villous adenoma, hamartoma, leiomyoma), colon, colon-rectum, colorectal, rectum; Genitourinary tract: kidney (adenocarcinoma, Wilm's tumor (nephroblastoma), lymphoma, leukemia), bladder and urethra (squamous cell carcinoma, transitional cell carcinoma, adenocarcinoma), prostate (adenocarcinoma, sarcoma), testis (seminoma, teratoma, embryonal carcinoma, teratocarcinoma, choriocarcinoma, sarcoma, interstitial cell carcinoma, fibroma, fibroadenoma, adenomatoid tumors, lipoma); Liver: hepatoma (hepatocellular carcinoma), cholangiocarcinoma, hepatoblastoma, angiosarcoma, hepatocellular adenoma, hemangioma, biliary passages; Bone: osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochronfroma (osteocartilaginous exostoses), benign chondroma, chondroblastoma, chondromyxofibroma, osteoid osteoma and giant cell tumors; Nervous system: skull (osteoma, hemangioma, granuloma, xanthoma, osteitis deformans), meninges (meningioma, meningiosarcoma, gliomatosis), brain (astrocytoma, medulloblastoma, glioma, ependymoma, germinoma (pinealoma), glioblastoma multiform, oligodendroglioma, schwannoma, retinoblastoma, congenital tumors), spinal cord neurofibroma, meningioma, glioma, sarcoma); Gynecological: uterus (endometrial carcinoma), cervix (cervical carcinoma, pre-tumor cervical dysplasia), ovaries (ovarian carcinoma (serous cystadenocarcinoma, mucinous cystadenocarcinoma, unclassified carcinoma), granulosa-thecal cell tumors, Sertoli-Leydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma (embryonal rhabdomyosarcoma), fallopian tubes (carcinoma), breast; Hematologic: blood (myeloid leukemia (acute and chronic), acute lymphoblastic leukemia, chronic lymphocytic leukemia, myeloproliferative diseases, multiple myeloma, myelodysplastic syndrome), Hodgkin's disease, non-Hodgkin's lymphoma (malignant lymphoma) hairy cell; lymphoid disorders; Skin: malignant melanoma, basal cell carcinoma, squamous cell carcinoma, Karposi's sarcoma, keratoacanthoma, moles dysplastic nevi, lipoma, angioma, dermatofibroma, keloids, psoriasis, Thyroid gland: papillary thyroid carcinoma, follicular thyroid carcinoma; medullary thyroid carcinoma, undifferentiated thyroid cancer, multiple endocrine neoplasia type 2A, multiple endocrine neoplasia type 2B, familial medullary thyroid cancer, pheochromocytoma, paraganglioma; and Adrenal glands: neuroblastoma. Thus, the term "cancerous cell" as provided herein, includes a cell afflicted by any one of the above-identified conditions.

The term "AMD" herein refers to age related macular degeneration.

The term "ALK" herein refers to anaplastic lymphoma kinase.

The term "SRPK1" herein refers to serine-rich protein kinase-1.

The term "SRPK2" herein refers to serine-rich protein kinase-1.

The term "VEGF" herein refers to vascular endothelial growth factor.

The term "subject" as used herein refers to a mammal. A subject therefore refers to, for example, dogs, cats, horses, cows, pigs, guinea pigs, and the like. Preferably the subject is a human. When the subject is a human, the subject may be referred to herein as a patient.

"Treat", "treating", and "treatment" refer to a method of alleviating or abating a disease and/or its attendant symptoms.

As used herein, "preventing" or "prevent" describes reducing or eliminating the onset of the symptoms or complications of the disease, condition, or disorder.

As used herein the term "AF802" or "Alectinib" refers to a compound having the chemical structure:

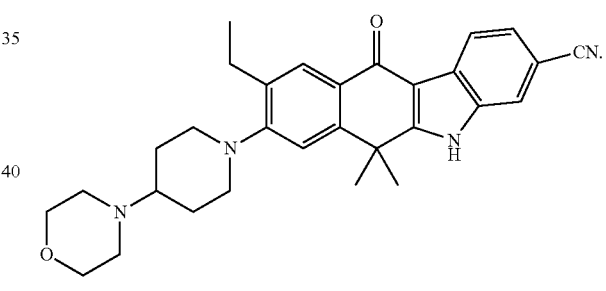

As used herein the term "LDK378" or "Ceritinib" refers to a compound having the chemical structure:

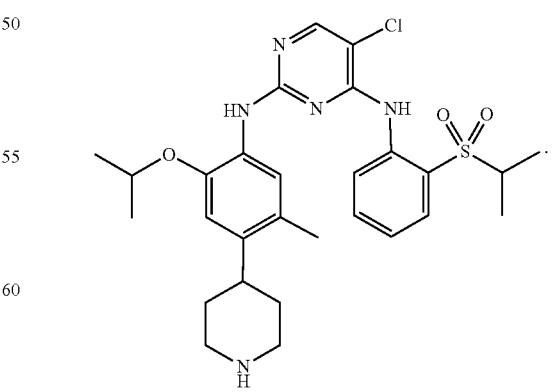

As used herein the term "AP26113" or "Brigatinib" refers to a compound having the chemical structure:

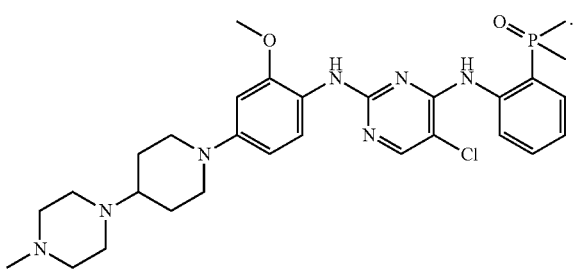

As used herein the term "Crizotinib" or "Xalkori" refers to a compound having the chemical structure:

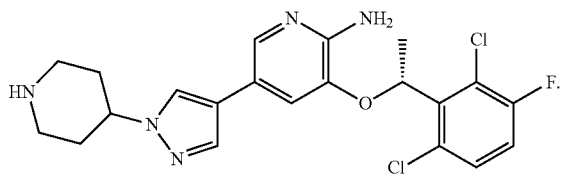 [SMILES: C[C@@H](Oc1cc(-c2cnn(C3CCNCC3)c2)cnc1N)c1c(Cl)ccc(F)c1Cl]

As used herein the term "PF-06463922" refers to a compound having the chemical structure:

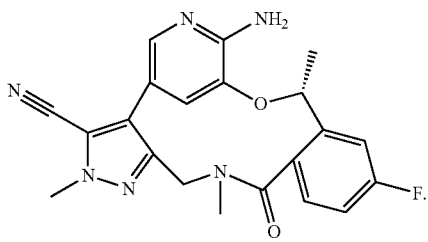 [SMILES: C[C@H]1Oc2cc(cnc2N)-c2c(nn(C)c2C#N)CN(C)C(=O)c2ccc(F)cc21]

As used herein, the term "pharmaceutically acceptable salt" refers to those salts of the compounds formed by the process of the present application which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge, et al. describes pharmaceutically acceptable salts in detail in J. Pharmaceutical Sciences, 66: 1-19 (1977). The salts can be prepared in situ during the final isolation and purification of a compound of the application, or separately by reacting the free base function with a suitable organic acid.

Examples of pharmaceutically acceptable salts include, but are not limited to, salts formed with inorganic acids such as hydrochloric acid, hydrobromic acid, phosphoric acid, sulfuric acid, and perchloric acid, or with organic acids such as acetic acid, maleic acid, tartaric acid, citric acid, succinic acid, or malonic acid, or by using other methods used in the art such as ion exchange. Other pharmaceutically acceptable salts include, but are not limited to, adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, alkyl having from 1 to 6 carbon atoms, sulfonate and aryl sulfonate.

As used herein, the term "pharmaceutically acceptable ester" refers to esters of the compounds formed by the process of the present application which hydrolyze in vivo and include those that break down readily in the human body to leave the parent compound or a salt thereof. Suitable ester groups include, for example, those derived from pharmaceutically acceptable aliphatic carboxylic acids, particularly alkanoic, alkenoic, cycloalkanoic, and alkanedioic acids, in which each alkyl or alkenyl moiety advantageously has not more than 6 carbon atoms. Examples of particular esters include, but are not limited to, formates, acetates, propionates, butyrates, acrylates and ethylsuccinates.

The term "pharmaceutically acceptable prodrugs" as used herein refers to those prodrugs of the compounds formed by the process of the present application which are, within the scope of sound medical judgment, suitable for use in contact with the tissues of humans and lower animals with undue toxicity, irritation, allergic response, and the like, commensurate with a reasonable benefit/risk ratio, and effective for their intended use, as well as the zwitterionic forms, where possible, of a compound of the present application. "Prodrug", as used herein means a compound which is convertible in vivo by metabolic means (e.g., by hydrolysis) to afford any compound delineated by the formulae of the instant application. Various forms of prodrugs are known in the art, for example, as discussed in Bundgaard, (ed.), Design of Prodrugs, Elsevier (1985); Widder, et al. (ed.), Methods in Enzymology, vol. 4, Academic Press (1985); Krogsgaard-Larsen, et al., (ed). "Design and Application of Prodrugs, Textbook of Drug Design and Development, Chapter 5, 113-191 (1991); Bundgaard, et al., Journal of Drug Deliver Reviews, 8:1-38(1992); Bundgaard, J. of Pharmaceutical Sciences, 77:285 et seq. (1988); Higuchi and Stella (eds.) Prodrugs as Novel Drug Delivery Systems, American Chemical Society (1975); and Bernard Testa & Joachim Mayer, "Hydrolysis In Drug And Prodrug Metabolism: Chemistry, Biochemistry And Enzymology," John Wiley and Sons, Ltd. (2002).

This application also encompasses pharmaceutical compositions containing, and methods of treating disorders through administering, pharmaceutically acceptable prodrugs of a compound of the application. For example, a compound of the application having free amino, amido, hydroxy or carboxylic groups can be converted into prodrugs. Prodrugs include compounds wherein an amino acid residue, or a polypeptide chain of two or more (e.g., two, three or four) amino acid residues is covalently joined through an amide or ester bond to a free amino, hydroxy or carboxylic acid group of a compound of the application. The amino acid residues include but are not limited to the 20 naturally occurring amino acids commonly designated by three letter symbols and also includes 4-hydroxyproline, hydroxylysine, demosine, isodemosine, 3-methylhistidine, norvalin, beta-alanine, gamma-aminobutyric acid, citrulline, homocysteine, homoserine, ornithine and methionine sulfone. Additional types of prodrugs are also encompassed. For instance, free carboxyl groups can be derivatized as amides or alkyl esters. Free hydroxy groups may be derivatized using groups including but not limited to hemisuccinates, phosphate esters, dimethylaminoacetates, and phosphoryloxymethyloxy carbonyls, as outlined in Advanced Drug Delivery Reviews, 1996, 19, 1 15. Carbamate prodrugs of hydroxy and amino groups are also included, as are carbonate prodrugs, sulfonate esters and sulfate esters of hydroxy groups. Derivatization of hydroxy groups as (acyloxy)methyl and (acyloxy)ethyl ethers wherein the acyl group may be an alkyl ester, optionally substituted with groups including but not limited to ether, amine and carboxylic acid functionalities, or where the acyl group is an amino acid ester as described above, are also encompassed. Prodrugs of this type are described in J. Med. Chem. 1996, 39, 10. Free amines can also be derivatized as amides, sulfonamides or phosphonamides. All of these prodrug moieties may incorporate groups including but not limited to ether, amine and carboxylic acid functionalities.

Combinations of substituents and variables envisioned by this application are only those that result in the formation of stable compounds. The term "stable", as used herein, refers to compounds which possess stability sufficient to allow manufacture and which maintains the integrity of the compound for a sufficient period of time to be useful for the purposes detailed herein (e.g., therapeutic or prophylactic administration to a subject).

The application also provides for a pharmaceutical composition comprising a compound disclosed herein, or a pharmaceutically acceptable ester, salt, or prodrug thereof, together with a pharmaceutically acceptable carrier.

In another aspect, the application provides a method of synthesizing a compound disclosed herein. The synthesis of a compound of the application can be found herein and in the Examples below.

Another aspect is an isotopically labeled compound of any of the formulae delineated herein. Such compounds have one or more isotope atoms which may or may not be radioactive (e.g., $^3H$, $^2H$, $^{14}C$, $^{13}C$, $^{18}F$, $^{35}S$, $^{32}P$, $^{125}I$, and $^{131}I$) introduced into the compound. Such compounds are useful for drug metabolism studies and diagnostics, as well as therapeutic applications.

A compound of the application can be prepared as a pharmaceutically acceptable acid addition salt by reacting the free base form of the compound with a pharmaceutically acceptable inorganic or organic acid. Alternatively, a pharmaceutically acceptable base addition salt of a compound of the application can be prepared by reacting the free acid form of the compound with a pharmaceutically acceptable inorganic or organic base.

Alternatively, the salt forms of a compound of the application can be prepared using salts of the starting materials or intermediates.

The free acid or free base forms of a compound of the application can be prepared from the corresponding base addition salt or acid addition salt from, respectively. For example a compound of the application in an acid addition salt form can be converted to the corresponding free base by treating with a suitable base (e.g., ammonium hydroxide solution, sodium hydroxide, and the like). A compound of the application in a base addition salt form can be converted to the corresponding free acid by treating with a suitable acid (e.g., hydrochloric acid, etc.).

Prodrugs of a compound of the application can be prepared by methods known to those of ordinary skill in the art (e.g., for further details see Saulnier et al., (1994), Bioorganic and Medicinal Chemistry Letters, Vol. 4, p. 1985). For example, appropriate prodrugs can be prepared by reacting a non-derivatized compound of the application with a suitable carbamylating agent (e.g., 1,1-acyloxyalkylcarbanochloridate, para-nitrophenyl carbonate, or the like).

Protected derivatives of a compound of the application can be made by means known to those of ordinary skill in the art. A detailed description of techniques applicable to the creation of protecting groups and their removal can be found in T. W. Greene, "Protecting Groups in Organic Chemistry", 3rd edition, John Wiley and Sons, Inc., 1999.

Acids and bases useful in the methods herein are known in the art. Acid catalysts are any acidic chemical, which can be inorganic (e.g., hydrochloric, sulfuric, nitric acids, aluminum trichloride) or organic (e.g., camphorsulfonic acid, p-toluenesulfonic acid, acetic acid, ytterbium triflate) in nature. Acids are useful in either catalytic or stoichiometric amounts to facilitate chemical reactions. Bases are any basic chemical, which can be inorganic (e.g., sodium bicarbonate, potassium hydroxide) or organic (e.g., triethylamine, pyridine) in nature. Bases are useful in either catalytic or stoichiometric amounts to facilitate chemical reactions.

In addition, some of a compound of this application have one or more double bonds, or one or more asymmetric centers. Such compounds can occur as racemates, racemic mixtures, single enantiomers, individual diastereomers, diastereomeric mixtures, and cis- or trans- or E- or Z-double isomeric forms, and other stereoisomeric forms that may be defined, in terms of absolute stereochemistry, as (R)- or (S)-, or as (D)- or (L)- for amino acids. All such isomeric forms of these compounds are expressly included in the present application.

Optical isomers may be prepared from their respective optically active precursors by the procedures described herein, or by resolving the racemic mixtures. The resolution can be carried out in the presence of a resolving agent, by chromatography or by repeated crystallization or by some combination of these techniques which are known to those skilled in the art. Further details regarding resolutions can be found in Jacques, et al., Enantiomers, Racemates, and Resolutions (John Wiley & Sons, 1981).

"Isomerism" means compounds that have identical molecular formulae but differ in the sequence of bonding of their atoms or in the arrangement of their atoms in space. Isomers that differ in the arrangement of their atoms in space are termed "stereoisomers". Stereoisomers that are not mirror images of one another are termed "diastereoisomers", and stereoisomers that are non-superimposable mirror images of each other are termed "enantiomers" or sometimes optical isomers. A mixture containing equal amounts of individual enantiomeric forms of opposite chirality is termed a "racemic mixture".

A carbon atom bonded to four non-identical substituents is termed a "chiral center".

"Chiral isomer" means a compound with at least one chiral center. Compounds with more than one chiral center may exist either as an individual diastereomer or as a mixture of diastereomers, termed "diastereomeric mixture". When one chiral center is present, a stereoisomer may be characterized by the absolute configuration (R or S) of that chiral center. Absolute configuration refers to the arrangement in space of the substituents attached to the chiral center. The substituents attached to the chiral center under consideration are ranked in accordance with the Sequence Rule of Cahn, Ingold and Prelog. (Cahn et al., Angew. Chem. Inter. Edit. 1966, 5, 385; errata 511; Cahn et al., Angew. Chem. 1966, 78, 413; Cahn and Ingold, J. Chem. Soc. 1951 (London), 612; Cahn et al., Experientia 1956, 12, 81; Cahn, J. Chem. Educ. 1964, 41, 116).

"Geometric isomer" means the diastereomers that owe their existence to hindered rotation about double bonds. These configurations are differentiated in their names by the prefixes cis and trans, or Z and E, which indicate that the groups are on the same or opposite side of the double bond in the molecule according to the Cahn-Ingold-Prelog rules.

Furthermore, the structures and other compounds discussed in this application include all atropic isomers thereof "Atropic isomers" are a type of stereoisomer in which the atoms of two isomers are arranged differently in space. Atropic isomers owe their existence to a restricted rotation caused by hindrance of rotation of large groups about a central bond. Such atropic isomers typically exist as a mixture, however as a result of recent advances in chromatography techniques; it has been possible to separate mixtures of two atropic isomers in select cases.

"Tautomer" is one of two or more structural isomers that exist in equilibrium and is readily converted from one isomeric form to another. This conversion results in the formal migration of a hydrogen atom accompanied by a switch of adjacent conjugated double bonds. Tautomers exist as a mixture of a tautomeric set in solution. In solid form, usually one tautomer predominates. In solutions where tautomerization is possible, a chemical equilibrium of the tautomers will be reached. The exact ratio of the tautomers depends on several factors, including temperature, solvent and pH. The concept of tautomers that are interconvertable by tautomerizations is called tautomerism.

Of the various types of tautomerism that are possible, two are commonly observed. In keto-enol tautomerism a simultaneous shift of electrons and a hydrogen atom occurs. Ring-chain tautomerism arises as a result of the aldehyde group (—CHO) in a sugar chain molecule reacting with one of the hydroxy groups (—OH) in the same molecule to give it a cyclic (ring-shaped) form as exhibited by glucose. Common tautomeric pairs are: ketone-enol, amide-nitrile, lactam-lactim, amide-imidic acid tautomerism in heterocyclic rings (e.g., in nucleobases such as guanine, thymine and cytosine), amine-enamine and enamine-enamine.

A compound of this application may also be represented in multiple tautomeric forms, in such instances, the application expressly includes all tautomeric forms of the compounds described herein (e.g., alkylation of a ring system may result in alkylation at multiple sites, the application expressly includes all such reaction products). When the compounds described herein contain olefinic double bonds or other centers of geometric asymmetry, and unless specified otherwise, it is intended that the compounds include both E and Z geometric isomers. Likewise, all tautomeric forms are also intended to be included. The configuration of any carbon-carbon double bond appearing herein is selected for convenience only and is not intended to designate a particular configuration unless the text so states; thus a carbon-carbon double bond depicted arbitrarily herein as trans may be cis, trans, or a mixture of the two in any proportion. All such isomeric forms of such compounds are expressly included in the present application.

In the present specification, the structural formula of the compound represents a certain isomer for convenience in some cases, but the present application includes all isomers, such as geometrical isomers, optical isomers based on an asymmetrical carbon, stereoisomers, tautomers, and the like.

Additionally, a compound of the present application, for example, the salts of the compounds, can exist in either hydrated or unhydrated (the anhydrous) form or as solvates with other solvent molecules. Non-limiting examples of hydrates include monohydrates, dihydrates, etc. Non-limiting examples of solvates include ethanol solvates, acetone solvates, etc.

A compound of the present application can be conveniently prepared, or formed during the process of the application, as solvates (e.g., hydrates). Hydrates of a compound of the present application can be conveniently prepared by recrystallization from an aqueous/organic solvent mixture, using organic solvents such as dioxin, tetrahydrofuran or methanol.

"Solvate" means solvent addition forms that contain either stoichiometric or non stoichiometric amounts of solvent. Some compounds have a tendency to trap a fixed molar ratio of solvent molecules in the crystalline solid state, thus forming a solvate. If the solvent is water the solvate formed is a hydrate; and if the solvent is alcohol, the solvate formed is an alcoholate. Hydrates are formed by the combination of one or more molecules of water with one molecule of the substance in which the water retains its molecular state as $H_2O$.

The synthesized compounds can be separated from a reaction mixture and further purified by a method such as column chromatography, high pressure liquid chromatography, or recrystallization. As can be appreciated by the skilled artisan, further methods of synthesizing a compound of the formulae herein will be evident to those of ordinary skill in the art. Additionally, the various synthetic steps may be performed in an alternate sequence or order to give the desired compounds. In addition, the solvents, temperatures, reaction durations, etc. delineated herein are for purposes of illustration only and one of ordinary skill in the art will recognize that variation of the reaction conditions can produce the desired bridged macrocyclic products of the present application. Synthetic chemistry transformations and protecting group methodologies (protection and deprotection) useful in synthesizing the compounds described herein are known in the art and include, for example, those such as described in R. Larock, Comprehensive Organic Transformations, VCH Publishers (1989); T. W. Greene and P. G. M. Wuts, Protective Groups in Organic Synthesis, 2d. Ed., John Wiley and Sons (1991); L. Fieser and M. Fieser, Fieser and Fieser's Reagents for Organic Synthesis, John Wiley and Sons (1994); and L. Paquette, ed., Encyclopedia of Reagents for Organic Synthesis, John Wiley and Sons (1995), and subsequent editions thereof.

A compound of this application may be modified by appending various functionalities via any synthetic means delineated herein to enhance selective biological properties. Such modifications are known in the art and include those which increase biological penetration into a given biological system (e.g., blood, lymphatic system, central nervous system), increase oral availability, increase solubility to allow administration by injection, alter metabolism and alter rate of excretion.

A compound of the application is defined herein by their chemical structures and/or chemical names. Where a compound is referred to by both a chemical structure and a chemical name, and the chemical structure and chemical name conflict, the chemical structure is determinative of the compound's identity.

The recitation of a listing of chemical groups in any definition of a variable herein includes definitions of that variable as any single group or combination of listed groups.

The recitation of an embodiment for a variable herein includes that embodiment as any single embodiment or in combination with any other embodiments or portions thereof.

Methods of Synthesizing the Compounds

A compound of the present application may be made by a variety of methods, including standard chemistry. The synthetic processes of the application can tolerate a wide variety of functional groups, therefore various substituted starting materials can be used. The processes generally provide the desired final compound at or near the end of the overall process, although it may be desirable in certain instances to further convert the compound to a pharmaceutically acceptable salt, ester, or prodrug thereof. Suitable synthetic routes are depicted in the schemes below.

A compound of the present application can be prepared in a variety of ways using commercially available starting materials, compounds known in the literature, or from readily prepared intermediates, by employing standard synthetic methods and procedures either known to those skilled in the art, or which will be apparent to the skilled artisan in light of the teachings herein. Standard synthetic methods and procedures for the preparation of organic molecules and functional group transformations and manipulations can be obtained from the relevant scientific literature or from standard textbooks in the field. Although not limited to any one or several sources, classic texts such as Smith, M. B., March, J., March's Advanced Organic Chemistry: Reactions, Mechanisms, and Structure, $5^{th}$ edition, John Wiley & Sons: New York, 2001; and Greene, T. W., Wuts, P. G. M., Protective Groups in Organic Synthesis, $3^{rd}$ edition, John Wiley & Sons: New York, 1999, incorporated by reference herein, are useful and recognized reference textbooks of organic synthesis known to those in the art. The following descriptions of synthetic methods are designed to illustrate, but not to limit, general procedures for the preparation of a compound of the present application.

A compound disclosed herein may be prepared by methods known in the art of organic synthesis as set forth in part by the following synthetic schemes. In the schemes described below, it is well understood that protecting groups for sensitive or reactive groups are employed where necessary in accordance with general principles or chemistry. Protecting groups are manipulated according to standard methods of organic synthesis (T. W. Greene and P. G. M. Wuts, "Protective Groups in Organic Synthesis", Third edition, Wiley, New York 1999). These groups are removed at a convenient stage of the compound synthesis using methods that are readily apparent to those skilled in the art. The selection processes, as well as the reaction conditions and order of their execution, shall be consistent with the preparation of a compound disclosed herein.

Those skilled in the art will recognize if a stereocenter exists in a compound disclosed herein. Accordingly, the present application includes both possible stereoisomers (unless specified in the synthesis) and includes not only racemic compounds but the individual enantiomers and/or diastereomers as well. When a compound is desired as a single enantiomer or diastereomer, it may be obtained by stereospecific synthesis or by resolution of the final product or any convenient intermediate. Resolution of the final product, an intermediate, or a starting material may be affected by any suitable method known in the art. See, for example, "Stereochemistry of Organic Compounds" by E. L. Eliel, S. H. Wilen, and L. N. Mander (Wiley-Interscience, 1994).

The compounds described herein may be made from commercially available starting materials or synthesized using known organic, inorganic, and/or enzymatic processes.

All the abbreviations used in this application are found in "Protective Groups in Organic Synthesis" by John Wiley & Sons, Inc, or the MERCK INDEX by MERCK & Co., Inc, or other chemistry books or chemicals catalogs by chemicals vendor such as Aldrich, or according to usage know in the art.

A compound of the present application can be prepared in a number of ways well known to those skilled in the art of organic synthesis. By way of example, a compound of the present application can be synthesized using the methods described below, together with synthetic methods known in the art of synthetic organic chemistry, or variations thereon as appreciated by those skilled in the art. Preferred methods include but are not limited to those methods described below. A compound of the present application can be synthesized by following the steps outlined in General Scheme A. Starting materials are either commercially available or made by known procedures in the reported literature or as illustrated.

General Scheme A

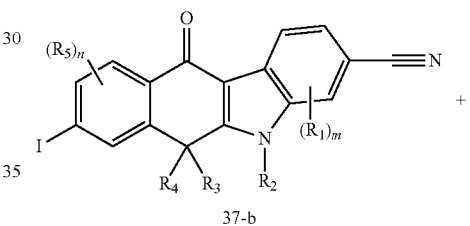

37-b

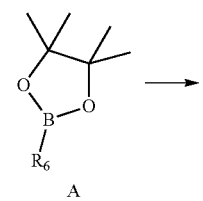

A

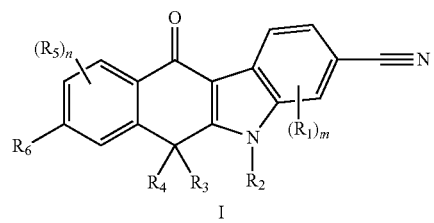

I

The general way of preparing a compound of Formula (I) is exemplified in General Scheme A. Compound 37-b is reacted with Compound A in a suitable solvent, e.g., 1,4-dioxane, through Suzuki coupling to yield a compound of Formula (I).

General Scheme A1

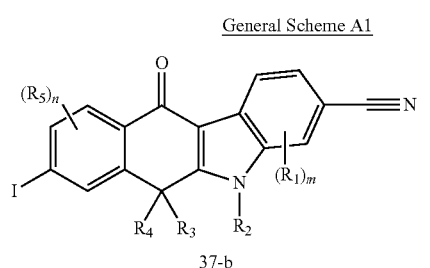

37-b

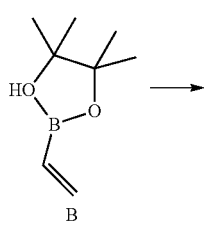

B

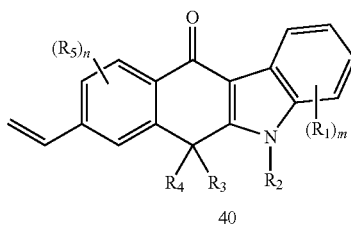

40

Compound 37-b is reacted with Compound B in a suitable solvent, e.g., 1,4-dioxane, through Suzuki coupling to yield Compound 40, which can be used as an intermediate to prepare other compounds of Formula (I).

Synthetic Scheme 1

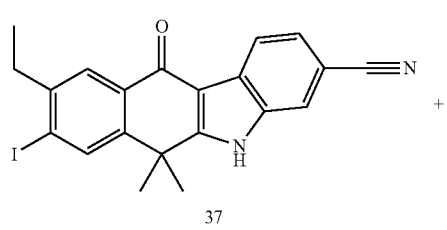

37

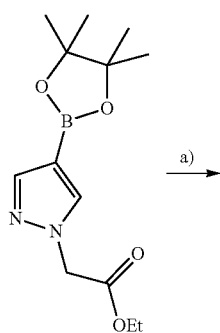

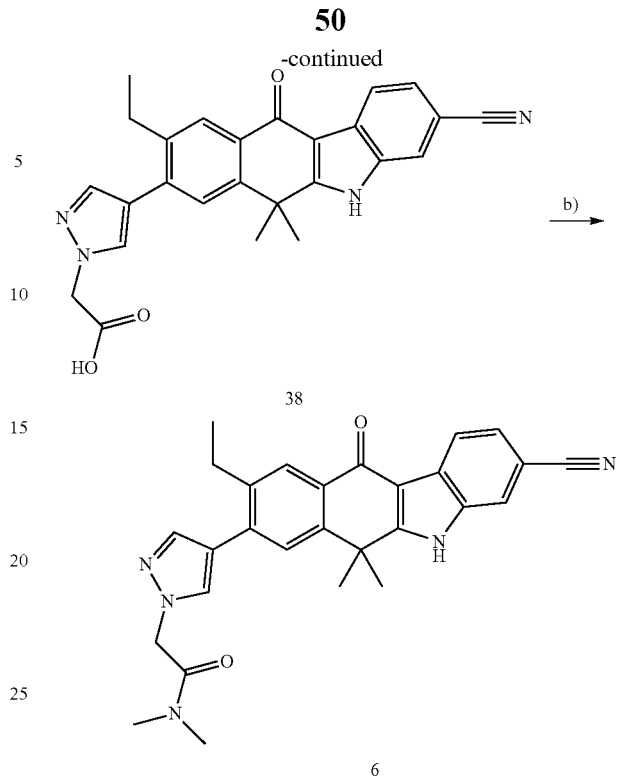

a) 6 mol % Pd(Dppf)Cl₂, 8 mol % t-BuXphos, 5 equi. 2M aq Na₂CO₃, 1,4-Dioxane 100° C., 1 h, then 2 equi. LiOH, H₂O, rt
b) 1.2 equi. dimethylamine HCl, 2 equi. HATU, 5 equi. DIEA, DMF 54%

Scheme 1 shows the synthetic route to Compound 6. Starting material Compound 37 (commercially available) is subjected to Suzuki coupling conditions followed by ester hydrolysis to afford the carboxylic acid Compound 38. Compound 38 is then reacted with dimethyalmine HCl and HATU to provide Compound 6.

Synthetic Scheme 2

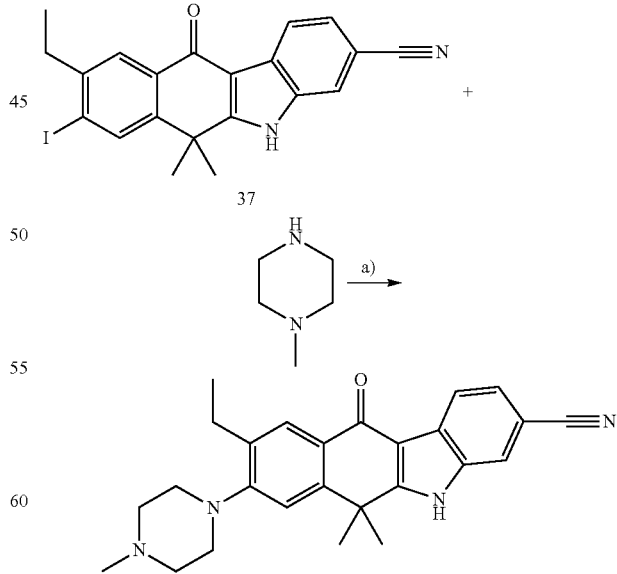

a) 6 mol % Pd₂(dba)₃, 9 mol % Tri (o-tolyl), 8 equi. NaOt-bu, 1,4-Dioxane 110° C., 2 h, 48%

Compounds with an alkyl heterocyclic ring substituent are prepared by subjecting Compound 37 to Buchwald-Hartwig coupling conditions using the desired amine (Scheme 2).

Synthetic Scheme 3

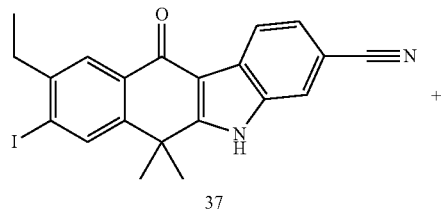

37

+

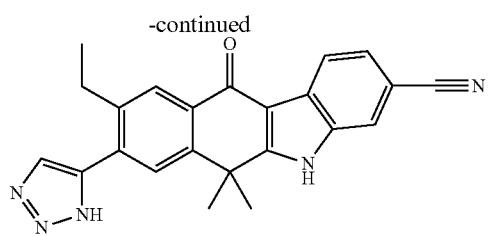

13 a) 5 mol % Pd(OAc)$_2$, 12 mol % PPh$_3$, 11 mol % CuI, Et$_2$NH, 90° C., 4 h, then 3 equi. TBAF, THF, 4 h
b) 1.5 equi. TMS—N$_3$, 5 mol % CuI, DMF, MeOH, 100° C., 4 h, 36%

Scheme 3 provides the synthetic route to prepare Compound 13 and a compound of the present application with similar structures.

Synthetic Scheme 4

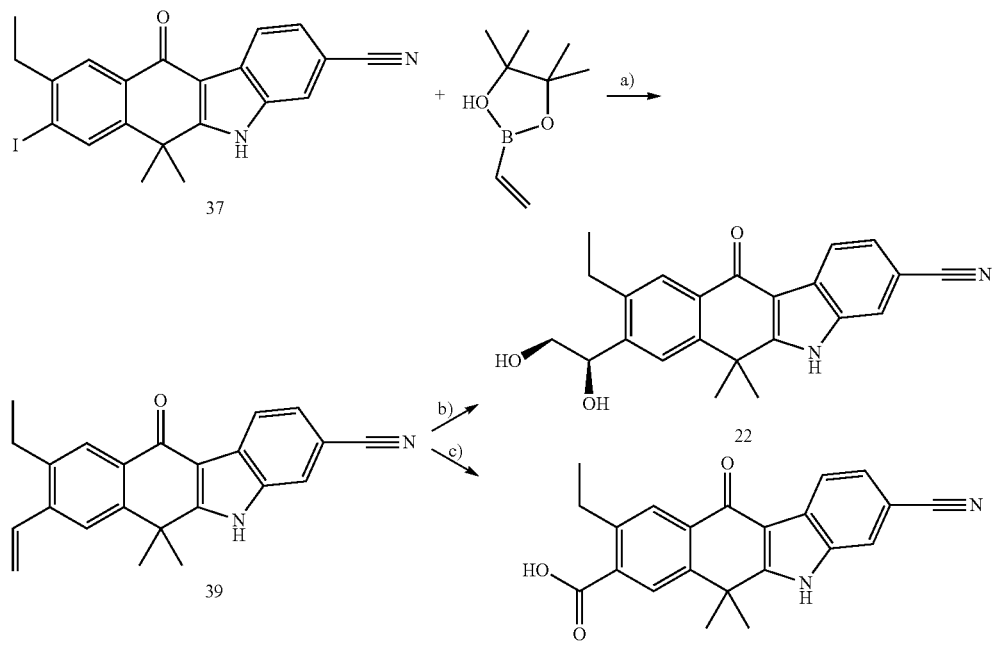

a) 6 mol % Pd(Dppf)Cl$_2$, 8 mol % t-BuXphos, 5 equi. 2M aq Na$_2$CO$_3$, 1,4-Dioxane 100° C., 1 h
b) 5 mol % ad-mix β, t-BuOH, H$_2$O, 0° C. to rt, 12 h, 51%
c) 1 mol % OsO$_4$, 4 equi. Oxone, rt, 6 h, 82%

-continued

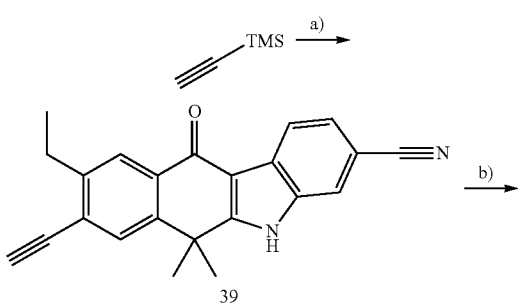

Scheme 4 provides the synthetic route to prepare Compounds 22 and 24 and a compound of the present application with similar structures.

A mixture of enantiomers, diastereomers, and/or cis/trans isomers resulting from the processes described above can be separated into their single components by chiral salt technique, chromatography using normal phase, or reverse phase or chiral column, depending on the nature of the separation.

It should be understood that in the description and formulae shown above, the various groups $R_1$-$R_6$, m, and n are as defined herein, except where otherwise indicated. Furthermore, for synthetic purposes, the compounds in the Schemes are mere representatives with elected sustituents to illustrate the general synthetic methodology of a compound disclosed herein.

Biological Assays
Growth Inhibition Assay

A compound of the present application is tested in various cells (e.g., Ba/F$_3$ cells, or tumor cell lines such as NSCLC) untransduced or transduced with wild-type ALK or ALK comprising one or more mutations (e.g., mutations described herein) in a growth inhibition assay at a fixed concentration or a series of concentrations. The cells are treated with the compounds for different durations, after which the percentage of viable cells was determined via a MTS assay. If necessary, the IC$_{50}$'s or EC$_{50}$'s are then calculated.

Western Blotting

Cell lysates from cells treated with a compound of the present application is equalized to protein content and loaded onto a gel with running buffer. Proteins are transferred from the gel to membranes, which are probed with primary antibodies against the protein (e.g., ALK). Secondary antibodies are added and after washing, the amount of the protein is determined, e.g., by detecting the signal intensity of a HRP substrate reagent with an imager.

Methods of the Application

In another aspect, the application provides a method of inhibiting a kinase (e.g., SRPK (e.g., SRPK1 and/or SRPK2), ALK or a mutant ALK (e.g., ALK G1202R)) with a compound disclosed herein (e.g., a compound of any of Formula I, Ia, II, IIa, or IIb, or any specific compound, such as Compounds 6-38, disclosed herein), or a pharmaceutically acceptable salt, hydrate, solvate, prodrug, stereoisomer, or tautomer thereof. In some embodiments, the ALK comprises one or more mutations selected from C1156Y, F1174L, L1196M, L1152R, 1151 Tins, G1202R, G1269A, and S1206Y. In further embodiments, the mutant ALK comprises at least the mutation G1202R.

Another aspect of the application provides a method of treating or preventing a disease, the method comprising administering to a subject in need thereof an effective amount of a compound disclosed herein (e.g., a compound of any of Formula I, Ia, II, IIa, or IIb, or any specific compound, such as Compounds 6-38, disclosed herein), or a pharmaceutically acceptable salt, hydrate, solvate, prodrug, stereoisomer, or tautomer thereof. In some embodiments, the disease is mediated by a kinase. In further embodiments, the kinase is ALK (e.g., a wild-type ALK or mutant ALK described herein). In another embodiment, the kinase is SRPK (e.g., SRPK1 and/or SRPK2).

In some embodiments, the disease is mediated by ALK (e.g., ALK plays a role in the initiation or development of the disease). In further embodiments, the disease is mediated by a mutant ALK described herein. In further embodiments, the ALK mutant comprises at least the mutation G1202R.

In some embodiments, the disease is mediated by SRPK (e.g., SRPK1 and/or SRPK2) (e.g., SRPK1 and/or SRPK2 plays a role in the initiation or development of the disease). In further embodiments any disease ordisorder associated with abnormal angiogenesis or abnormal over-production of proangiogenic VEGF isoforms.

In certain embodiments, the disease is cancer or a proliferative disease.

In further embodiments, the cancer is non-small-cell lung cancer (NSCLC), inflammatory myofibroblastic tumors (IMT), diffuse large B cell lymphoma (DLBCL), squamous cell carcinoma, neuroblastoma, adult and pediatric renal cell carcinomas, glioblastoma multiforme, anaplastic thyroid cancer, colon cancer, breast cancer, prostate cancer, liver cancer, pancreas cancer, brain cancer, kidney cancer, ovarian cancer, stomach cancer, skin cancer, bone cancer, gastric cancer, breast cancer, pancreatic cancer, glioma, glioblastoma, hepatocellular carcinoma, papillary renal carcinoma, head and neck squamous cell carcinoma, leukemias, lymphomas, myelomas, or solid tumors. In further embodiments, the cancer is NSCLC or neuroblastoma.

In some embodiments, the cancer is a cancer of the central nervous system (CNS). In some embodiments, the cancer is a cancer from the replase of a cancer previously treated with an ALK targeted therapy, such as a therapy with Alectinib (AF802), Ceritinib (LDK378), Brigatinib (AP26113), Crizotinib (Xalkori), and/or PF-06463922.

In another aspect, the application provides a method of treating or preventing cancer, wherein the cancer cell comprise activated ALK, comprising administering to a subject in need thereof an effective amount of a compound disclosed herein (e.g., a compound of any of Formula I, Ia, II, IIa, or IIb, or any specific compound, such as Compounds 6-38, disclosed herein), or a pharmaceutically acceptable salt, hydrate, solvate, prodrug, stereoisomer, or tautomer thereof. In some embodiments, the activated ALK is a wild-type ALK. In other embodiments, the activated ALK is a mutant ALK described herein. In further embodiments, the activated ALK is a mutant ALK comprising at least the mutation G1202R.

Another aspect of the application provides a method of treating or preventing cancer in a subject, wherein the subject is identified as being in need of ALK inhibition for the treatment of cancer, comprising administering to the subject an effective amount of a compound disclosed herein (e.g., a compound of any of Formula I, Ia, II, IIa, or IIb, or any specific compound, such as Compounds 6-38, disclosed herein), or a pharmaceutically acceptable salt, hydrate, solvate, prodrug, stereoisomer, or tautomer thereof. In some embodiments, the subject is in need of inhibition of a wild-type ALK. In other embodiments, the subject is in need of inhibition of a mutant ALK described herein. In further embodiments, the subject is in need of inhibition of a mutant ALK comprising at least the mutation G1202R.

Another aspect of the application provides a method of treating or preventing a disease or disorder (e.g., cancer), wherein the disease or disorder is resistant to an ALK targeted therapy, such as a therapy with Alectinib (AF802), Ceritinib (LDK378), Brigatinib (AP26113), Crizotinib (Xalkori), and/or PF-06463922.

In another aspect, the application provides a method of treating or preventing cancer, wherein the cancer cell comprises a mutant ALK, comprising administering to a subject in need thereof an effective amount of a compound disclosed herein (e.g., a compound of any of Formula I, Ia, II, IIa, or IIb, or any specific compound, such as Compounds 6-38, disclosed herein), or a pharmaceutically acceptable salt, hydrate, solvate, prodrug, stereoisomer, or tautomer thereof. In some embodiments, the ALK mutant comprises one or more mutations described herein. In further embodiments, the ALK mutant comprises at least the mutation G1202R.

Another aspect of the application provides a method of treating or preventing resistance to a known ALK inhibitor, including but not limited to, Alectinib, Ceritinib, Brigatinib, Crizotinib or PF-06463922, comprising administering to a subject in need thereof an effective amount of a compound disclosed herein (e.g., a compound of any of Formula I, Ia, II, IIa, or IIb, or any specific compound, such as Compounds 6-38, disclosed herein), or a pharmaceutically acceptable salt, hydrate, solvate, prodrug, stereoisomer, or tautomer thereof.

In certain embodiments, the application provides a method of treating any of the disorders described herein, wherein the subject is a human. In certain embodiments, the application provides a method of preventing any of the disorders described herein, wherein the subject is a human.

In another aspect, the application provides a compound disclosed herein (e.g., a compound of any of Formula I, Ia, II, IIa, or IIb, or any specific compound, such as Compounds 6-38, disclosed herein), or a pharmaceutically acceptable salt, hydrate, solvate, prodrug, stereoisomer, or tautomer thereof, for use in the manufacture of a medicament for treating or preventing a disease in which ALK plays a role.

In still another aspect, the application provides a compound disclosed herein (e.g., a compound of any of Formula I, Ia, II, IIa, or IIb, or any specific compound, such as Compounds 6-38, disclosed herein), or a pharmaceutically acceptable salt, hydrate, solvate, prodrug, stereoisomer, or tautomer thereof, for inhibiting a kinase (e.g., ALK or a mutant ALK (e.g., ALK G1202R), or SRPK (e.g., SRPK1 and/or SRPK2)); treating or preventing a disease or disorder (e.g., cancer) in which a kinase (e.g., ALK or a mutant ALK (e.g., ALK G1202R), or SRPK (e.g., SRPK1 and/or SRPK2)) plays a role; treating or preventing cancer, wherein the cancer cell comprises activated ALK or a mutant ALK; treating or preventing cancer in a subject identified as being in need of inhibition of ALK or the mutant ALK for the treatment or prevention of cancer; treating or preventing a disease or disorder (e.g., cancer) resistant to an ALK targeted therapy, such as a therapy with Alectinib (AF802), Ceritinib (LDK378), Brigatinib (AP26113), Crizotinib (Xalkori), and/or PF-06463922; regulating (e.g., inhibiting) VEGF mediated angiogenesis; treating or preventing a disease or disorder in which a VEGF mediated angiogenesis plays a role (e.g., AMD or angiogenesis-dependent cancers); treating or preventing AMD (e.g., in a subject identified in need of regulation (e.g., inhibition) of VEGF mediated angiogenesis for the treatment or prevention of AMD; and/or treating or preventing an angiogenesis-dependent cancer (e.g., tumorous cancer) (e.g., in a subject identified in need of regulation of VEGF mediated angiogenesis for the treatment or prevention of an angiogenesis-dependent cancer).

In still another aspect, the application provides use of a compound disclosed herein (e.g., a compound of any of Formula I, Ia, II, IIa, or IIb, or any specific compound, such as Compounds 6-38, disclosed herein), or a pharmaceutically acceptable salt, hydrate, solvate, prodrug, stereoisomer, or tautomer thereof, in the manufacture of a medicament for inhibiting a kinase (e.g., ALK or a mutant ALK (e.g., ALK G1202R), or SRPK (e.g., SRPK1 and/or SRPK2)); treating or preventing a disease or disorder (e.g., cancer) in which a kinase (e.g., ALK or a mutant ALK (e.g., ALK G1202R), or SRPK (e.g., SRPK1 and/or SRPK2)) plays a role; treating or preventing cancer, wherein the cancer cell comprises activated ALK or a mutant ALK; treating or preventing cancer in a subject identified as being in need of inhibition of ALK or the mutant ALK for the treatment or prevention of cancer; treating or preventing a disease or disorder (e.g., cancer) resistant to an ALK targeted therapy, such as a therapy with Alectinib (AF802), Ceritinib (LDK378), Brigatinib (AP26113), Crizotinib (Xalkori), and/or PF-06463922; regulating (e.g., inhibiting) VEGF mediated angiogenesis; treating or preventing a disease or disorder in which a VEGF mediated angiogenesis plays a role (e.g., AMD or angiogenesis-dependent cancers); treating or preventing AMD (e.g., in a subject identified in need of regulation (e.g., inhibition) of VEGF mediated angiogenesis for the treatment or prevention of AMD; and/or treating or preventing an angiogenesis-dependent cancer (e.g., tumorous cancer) (e.g., in a subject identified in need of regulation of VEGF mediated angiogenesis for the treatment or prevention of an angiogenesis-dependent cancer).

One aspect of this application provides compounds that are useful for the treatment of diseases, disorders, and conditions characterized by excessive or abnormal cell proliferation. Such diseases include, but are not limited to, a proliferative or hyperproliferative disease. Examples of proliferative and hyperproliferative diseases include, without limitation, cancer. The term "cancer" includes, but is not limited to, the following cancers: breast; ovary; cervix; prostate; testis, genitourinary tract; esophagus; larynx, glioblastoma; neuroblastoma; stomach; skin, keratoacanthoma; lung, epidermoid carcinoma, large cell carcinoma, small cell carcinoma, lung adenocarcinoma; bone; colon; colorectal; adenoma; pancreas, adenocarcinoma; thyroid, follicular carcinoma, undifferentiated carcinoma, papillary carcinoma; seminoma; melanoma; sarcoma; bladder carcinoma; liver carcinoma and biliary passages; kidney carcinoma; myeloid disorders; lymphoid disorders, Hodgkin's, hairy cells; buccal cavity and pharynx (oral), lip, tongue, mouth, pharynx; small intestine; colonrectum, large intestine, rectum, brain and central nervous system; chronic myeloid leukemia (CML), and leukemia. The term "cancer" includes, but is not limited to, the following cancers: myeloma, lymphoma, or a cancer selected from gastric, renal, or and the following cancers: head and neck, oropharangeal, non-small cell lung cancer (NSCLC), endometrial, hepatocarcinoma, Non-Hodgkins lymphoma, and pulmonary.

The term "cancer" refers to any cancer caused by the proliferation of malignant neoplastic cells, such as tumors, neoplasms, carcinomas, sarcomas, leukemias, lymphomas and the like. For example, cancers include, but are not limited to, mesothelioma, leukemias and lymphomas such as cutaneous T-cell lymphomas (CTCL), noncutaneous peripheral T-cell lymphomas, lymphomas associated with human T-cell lymphotrophic virus (HTLV) such as adult T-cell leukemia/lymphoma (ATLL), B-cell lymphoma, acute nonlymphocytic leukemias, chronic lymphocytic leukemia, chronic myelogenous leukemia, acute myelogenous leukemia, lymphomas, and multiple myeloma, non-Hodgkin lymphoma, acute lymphatic leukemia (ALL), chronic lymphatic leukemia (CLL), Hodgkin's lymphoma, Burkitt lymphoma, adult T-cell leukemia lymphoma, acute-myeloid leukemia (AML), chronic myeloid leukemia (CML), or hepatocellular carcinoma. Further examples include myelodisplastic syndrome, childhood solid tumors such as brain tumors, neuroblastoma, retinoblastoma, Wilms' tumor, bone tumors, and soft-tissue sarcomas, common solid tumors of adults such as head and neck cancers (e.g., oral, laryngeal, nasopharyngeal and esophageal), genitourinary cancers (e.g., prostate, bladder, renal, uterine, ovarian, testicular), lung cancer (e.g., small-cell and non-small cell), breast cancer, pancreatic cancer, melanoma and other skin cancers, stomach cancer, brain tumors, tumors related to Gorlin's syndrome (e.g., medulloblastoma, meningioma, etc.), and liver cancer. Additional exemplary forms of cancer which may be treated by the subject compounds include, but are not limited to, cancer of skeletal or smooth muscle, stomach cancer, cancer of the small intestine, rectum carcinoma, cancer of the salivary gland, endometrial cancer, adrenal cancer, anal cancer, rectal cancer, parathyroid cancer, and pituitary cancer.

Additional cancers that the compounds described herein may be useful in preventing, treating and studying are, for example, colon carcinoma, familiary adenomatous polyposis carcinoma and hereditary non-polyposis colorectal cancer, or melanoma. Further, cancers include, but are not limited to, labial carcinoma, larynx carcinoma, hypopharynx carcinoma, tongue carcinoma, salivary gland carcinoma, gastric carcinoma, adenocarcinoma, thyroid cancer (medullary and papillary thyroid carcinoma), renal carcinoma, kidney parenchyma carcinoma, cervix carcinoma, uterine corpus carcinoma, endometrium carcinoma, chorion carcinoma, testis carcinoma, urinary carcinoma, melanoma, brain tumors such as glioblastoma, astrocytoma, meningioma, medulloblastoma and peripheral neuroectodermal tumors, gall bladder carcinoma, bronchial carcinoma, multiple myeloma, basalioma, teratoma, retinoblastoma, choroidea melanoma, seminoma, rhabdomyosarcoma, craniopharyngeoma, osteosarcoma, chondrosarcoma, myosarcoma, liposarcoma, fibrosarcoma, Ewing sarcoma, and plasmocytoma. In one aspect of the application, the present application provides for the use of one or more a compound of the application in the manufacture of a medicament for the treatment of cancer, including without limitation the various types of cancer disclosed herein.

This application further embraces the treatment or prevention of cell proliferative disorders such as hyperplasias, dysplasias and pre-cancerous lesions. Dysplasia is the earliest form of pre-cancerous lesion recognizable in a biopsy by a pathologist. The subject compounds may be administered for the purpose of preventing said hyperplasias, dysplasias or pre-cancerous lesions from continuing to expand or from becoming cancerous. Examples of pre-cancerous lesions may occur in skin, esophageal tissue, breast and cervical intraepithelial tissue.

Another aspect of the application provides compounds that are useful for the treatment or prevention of any disease or disorder associated with abnormal angiogenesis or abnormal over-production of pro-angiogenicVEGF isoforms. Such diseases and disorders include, for example, vascular disease (e.g., vasoconstriction and disorders characterized by vasoconstriction, and cardiovascular disease), malignant and benign neoplasia (e.g., angiogenesis-dependent cancers, for example tumorous cancers), tumor metastasis, inflammatory disorders, diabetes, diabetic retinopathy and other complications of diabetes (e.g., diabetic neovascularisation), trachoma, retrolental hyperplasia, neovascular glaucoma, age-related macular degeneration, haemangioma, immune rejection of implanted corneal tissue, corneal angiogenesis associated with ocular injury or infection, Osier-Webber Syndrome, myocardial angiogenesis, wound granulation, telangiectasia, hemophiliac joints, angiofibroma, telangiectasia psoriasis scleroderma, pyogenic granuloma, coronary collaterals, ischemic limb abgiogenesis, rubeosis, obesity, arthritis (e.g., rheumatoid arthritis), hematopoieses, vasculogenesis, gingivitis, atherosclerosis, endometriosis, neointimal hyperplasia, psoriasis, hirsutism and proliferative retinopathy. In some embodiments, the application provides compounds that are useful for the treatment or prevention of AMD.

The anti-angiogenic treatment according to the present application may also include non-therapeutic treatments performed on healthy subjects, for example to inhibit vascular development for cosmetic purposes.

Other disorders in which the alternatively spliced VEGF isoform has been implicated, include but are not limited to microvascular hyperpermeability disorders, disorders of epithelial cell survival and disorders of fenestrations of epithelial filtration membranes. Examples of such conditions include, for example, proteinuria, uraemia, microalbuminuria, hypoalbuminemia, renal hyperfiltration, nephrotic syndrome, renal failure, pulmonary hypertension, capillary hyperpermeability, microaneurysms, oedema and vascular complications of diabetes (e.g., diabetic retinopathy, both proliferative and non-proliferative, and diabetic nephropathy).

Exemplary microvascular hyperpermeability disorders include, but are not limited to renal disorders, for example a permeability disorder of the glomerular filtration barrier (e.g., a permeability disorder of the podocytes).

Examples of disorders where treatment to support epithelial cell survival would be effective incude acute pulmonary fibrotic disease, adult respiratory distress syndrome, adult respiratory distress syndrome, advanced cancer, allergic respiratory disease, alveolar injury, angiogenesis, arthritis, ascites, asthma, asthma or edema following burns, atherosclerosis, autoimmune diseases, bone resorption, bullous disorder associated with subepidermal blister formation including bullous pemphigoid, cardiovascular condition, certain kidney diseases associated with proliferation of glomerular or mesangial cells, chronic and allergic inflammation, chronic lung disease, chronic occlusive pulmonary disease, cirrhosis, corneal angiogenisis, corneal disease, coronary and cerebral collateral vascularization, coronary restenosis, damage following heart disease, dermatitis herpetiformis, diabetes, diabetic nephropathy, diabetic retinopathy, endotoxic shock, erythema multiforme, fibrosis, glomerular nephritis, glomerulonophritis, graft rejection, gram negative sepsis, hemangioma, hepatic cirrhosis, hepatic failure, Herpes Zoster, host-versus-graft reaction (ischemia reperfusion injury and allograft rejections of kidney, liver, heart, and skin), impaired wound healing in infection, infection by Herpes simplex, infection from human immunodeficiency virus (HIV), inflammation, cancer, inflammatory bowel disease (Crohn's disease and ulcerative colitis), inflammatory conditions, in-stent restenosis, in-stent stenosis, ischemia, ischemic retinal-vein occlusion, ischemic retinopathy, Kaposi's sarcoma, keloid, liver disease during acute inflammation, lung allograft rejection (obliterative bronchitis), lymphoid malignancy, macular degeneration retinopathy of prematurity, myelodysplastic syndromes, myocardial angiogenesis, neovascular glaucoma, non-insulin-dependent diabetes mellitus (NIDDM), obliterative bronchiolitis, ocular conditions or diseases, ocular diseases associated with retinal vessel proliferation, Osier-Weber-Rendu disease, osteoarthritis, ovarian hyperstimulation syndrome, Paget's disease, pancreatitis, pemphigoid, polycystic kidney disease, polyps, postmenopausal osteoperosis, preeclampsia, psoriasis, pulmonary edema, pulmonary fibrosis, pulmonary sarcoidosis, restenosis, restenosis, retinopathy including diabetic retinopathy, retinopathy of prematurity, age related macular degeneration, rheumatoid arthritis, rubeosis, sarcoidosis, sepsis, stroke, synovitis, systemic lupus erythematosus, throiditis, thrombic micoangiopathy syndromes, transplant rejection, trauma, tumor-associated angiogenesis, vascular graft restenosis, vascular graft restenosis, von Hippel Lindau disease, and wound healing.

Yet another aspect of the application provides compounds that are useful for the treatment or prevention of macular dystrophy. Non-limiting examples of muscular dystrophy include Stargardt disease/fundus flavimaculatus, Stargardt-like macular dystrophy, Autosomal dominant bull's eye macular dystrophy, Best macular dystrophy, Adult vitelliform dystrophy, Pattern dystrophy, Doyne honeycomb retinal dystrophy, North Carolina macular dystrophy, Autosomal dominant macular dystrophy resembling MCDR1, North Carolina-like macular dystrophy associated with deafness, Progressive bifocal chorioretinal atrophy, Sorsby's fundus dystrophy, Central areolar choroidal dystrophy, Dominant cystoid macular dystrophy, Juvenile retinoschisis; Occult Macular Dystrophy, Non-familial Occult Macular Dystrophy. The disorder may particularly be a disorder of the retinal epithelium, such as geographic atrophy, or age related macular degeneration.

In still another aspect the application provides compounds that are useful for the treatment or prevention of neuropathic and neurodegenerative disorders. Neuropathic disorders to be treated or prevented according to the present application include neuropathic pain and diabetic and other neuropathies. Neurodegenerative disorders to be treated or prevented according to the present application include neurodegeneration of the cognitive and non-cognitive types, neuromuscular degeneration, motor-sensory neurodegeneration, and ocular neurodegeneration.

In a further aspect of the application, treatment of neuropathic and neurodegenerative disorders provides for the treatment or prevention of pain (e.g., neuropathic pain), dementia, age-related cognitive impairment, Alzheimer's disease, senile dementia of the Alzheimer's type (SDAT), Lewy body dementia, vascular dementia, Parkinson's disease, postencephalitic Parkinsonism, depression, schizophrenia, muscular dystrophy including facioscapulohumeral muscular dystrophy (FSH), Duchenne muscular dystrophy, Becker muscular dystrophy and Bruce's muscular dystrophy, Fuchs' dystrophy, myotonic dystrophy, corneal dystrophy, reflex sympathetic dystrophy syndrome (RSDSA), neurovascular dystrophy, myasthenia gravis, Lambert Eaton disease, Huntington's disease, motor neurone diseases including amyotrophic lateral sclerosis (ALS), multiple sclerosis, postural hypotension, traumatic neuropathy or neurodegeneration, for example following stroke or following an accident, (e.g., traumatic head injury or spinal cord injury), Batten's disease, Cockayne syndrome, Down syndrome, corticobasal ganglionic degeneration, multiple system atrophy, cerebral atrophy, olivopontocerebellar atrophy, dentatorubral atrophy, pallidoluysian atrophy, spinobulbar atrophy, optic neuritis, sclerosing pan-encephalitis (SSPE), attention deficit disorder, post-viral encephalitis, post-poliomyelitis syndrome, Fahr's syndrome, Joubert syndrome, Guillain-Barre syndrome, lissencephaly, Moyamoya disease, neuronal migration disorders, autistic syndrome, polyglutamine disease, Niemann-Pick disease, progressive multifocal leukoencephalopathy, pseudotumor cerebri, Refsum disease, Zellweger syndrome, supranuclear palsy, Friedreich's ataxia, spinocerebellar ataxia type 2, Rhett syndrome, Shy-Drager syndrome, tuberous sclerosis, Pick's disease, chronic fatigue syndrome, neuropathies including hereditary neuropathy, diabetic neuropathy and mitotic neuropathy, prion-based neurodegeneration, including Creutzfeldt-Jakob disease (CJD), variant CJD, new variant CJD, bovine spongiform encephalopathy (BSE), GSS, FFI, Kuru and Alper's syndrome, Joseph's disease, acute disseminated encephalomyelitis, arachnoiditis, vascular lesions of the central nervous system loss of extremity neuronal function, Charcot-Marie-Tooth disease, Krabbe's disease, leukodystrophies, susceptibility to heart failure, asthma, epilepsy, auditory neurodegeneration, macular degeneration, pigmentary retinitis and glaucoma-induced optic nerve degeneration.

In a still another aspect of the application, treatment of neuropathic and neurodegenerative disorders provides for the treatment of psychiatric disorders, which includes without limitation anxiety disorders (e.g., acute stress disorder, panic disorder, agoraphobia, social phobia, specific phobia, obsessive-compulsive disorder, sexual anxiety disorders, post-traumatic stress disorder, body dysmorphic disorder and generalized anxiety disorder), childhood disorders (e.g., attention-deficit hyperactivity disorder (ADHD), Asperger's disorder, autistic disorder, conduct disorder, oppositional defiant disorder, separation anxiety disorder and Tourette's disorder), eating disorders (for example, anorexia nervosa and bulimia nervosa), mood disorders (e.g., depression, major depressive disorder, bipolar disorder (manic depression), seasonal affective disorder (SAD), cyclothymic disorder and dysthymic disorder), sleeping disorders, cognitive psychiatric disorders (e.g., delirium, amnestic disorders), personality disorders (e.g., paranoid personality disorder, schizoid personality disorder, schizotypal personality disorder, antisocial personality disorder, borderline personality disorder, histrionic personality disorder, narcissistic personality disorder, avoidant personality disorder, dependent personality disorder andobsessive-compulsive personality disorder), psychotic disorders (e.g., schizophrenia, delusional disorder, brief psychotic disorder, schizophreniform disorder, schizoaffective disorder and shared psychotic disorder), and substance-related disorders (e.g., alcohol dependence, amphetamine dependence, cannabis dependence, cocaine dependence, hallucinogen dependence, inhalant dependence, nicotine dependence, opioid dependence, phencyclidine dependence and sedative dependence).

In another aspect of the application, the componds disclosed herein may be used to treat VEGFR2-mediated non-inflammatory pain. VEGFR2-mediated non-inflammatory pain to be treated or prevented according to the present application includes non-inflammatory neuropathic and nociceptive pain where the VEGFR2 receptor is involved in the cause or transmission of the pain. For example, the compounds according to the present application have activity against non-inflammatory allodynia and pain (antiallodynic and analgesic activity). Pain states of this type include chronic pain, whether of the intermittent or constant form. Such pain states may include, for example, low back pain, neuralgia, atypical pains such as atypical facial pain, pain exhibited post-surgery, post-injury (e.g., after surgery or injury causing nerve damage) or in association with cancer or with cancer therapy such as cytotoxic or radiation therapy, or neuropathy associated with diabetes (diabetic neuropathy, insulin neuritis) or other systemic or autoimmune disease or pathology, or the treatment thereof, alcoholism or HIV infection, ageing associated neuropathy, or neuropathy of unknown origin.

In accordance with the foregoing, the present application further provides a method for preventing or treating any of the diseases or disorders described above in a subject in need of such treatment, which method comprises administering to said subject a therapeutically effective amount of a compound of the application, or a pharmaceutically acceptable salt, hydrate, solvate, prodrug, stereoisomer, or tautomer thereof. For any of the above uses, the required dosage will vary depending on the mode of administration, the particular condition to be treated and the effect desired.

In another aspect, the application provides a method of labeling a SRPK protein with a compound of the present application, comprising interacting the SRPK protein with a compound of the present application (e.g., a compound of any of Formula I, Ia, II, IIa, or IIb, or any specific compound, such as Compounds 6-38, disclosed herein). In one embodiment, the SRPK protein is SRPK1. In another embodiment, the SRPK protein is SRPK2.

In one aspect, the SRPK protein (e.g., SRPK1) is labeled at one or more amino acid residues. In one embodiment, the SRPK protein (e.g., SRPK1) is labeled at one amino acid residue. In one embodiment, the SRPK1 protein is labeled at amino acid residue Y227. In one embodiment, the SRPK1 protein is labeled at amino acid residue Y227 with a compound of the present application (e.g., a compound of any of Formula I, Ia, II, IIa, or IIb, or any specific compound, such as Compounds 6-38, disclosed herein). In one embodiment, the SRPK1 protein is labeled at amino acid residue Y227 with Compound 37.

In one embodiment, interacting the SRPK protein with a compound of the present application (e.g., a compound of any of Formula I, Ia, II, IIa, or IIb, or any specific compound, such as Compounds 6-38, disclosed herein) involves binding of the compound with the SRPK protein. In one embodiment, the compound is bound to the SRPK protein at one or more amino acid residues. In one embodiment, the compound is bound to the SRPK protein at one amino acid residue. In one embodiment, the compound is bound to the SRPK protein at amino acid residue Y227.

The compound used to label the SRPK protein can itself be labeled. For example, the compound can be labeled radioactively or fluorescently, according to methods known in the art.

Pharmaceutical Compositions

In another aspect, the application provides a pharmaceutical composition comprising a compound disclosed herein, or a pharmaceutically acceptable ester, salt, or prodrug thereof, together with a pharmaceutically acceptable carrier.

A compound of the application can be administered as pharmaceutical compositions by any conventional route, in particular enterally, e.g., orally, e.g., in the form of tablets or capsules, or parenterally, e.g., in the form of injectable solutions or suspensions, topically, e.g., in the form of lotions, gels, ointments or creams, or in a nasal or suppository form. Pharmaceutical compositions comprising a compound of the present application in free form or in a pharmaceutically acceptable salt form in association. For example, oral compositions can be tablets or gelatin capsules comprising the active ingredient together with a) diluents, e.g., lactose, dextrose, sucrose, mannitol, sorbitol, cellulose and/or glycine; b) lubricants, e.g., silica, talcum, stearic acid, its magnesium or calcium salt and/or polyethyleneglycol; for tablets also c) binders, e.g., magnesium aluminum silicate, starch paste, gelatin, tragacanth, methylcellulose, sodium carboxymethylcellulose and or polyvinylpyrrolidone; if desired d) disintegrants, e.g., starches, agar, alginic acid or its sodium salt, or effervescent mixtures; and/or e) absorbents, colorants, flavors and sweeteners. Injectable compositions can be aqueous isotonic solutions or suspensions, and suppositories can be prepared from fatty emulsions or suspensions. The compositions may be sterilized and/or contain adjuvants, such as preserving, stabilizing, wetting or emulsifying agents, solution promoters, salts for regulating the osmotic pressure and/or buffers. In addition, they may also contain other therapeutically valuable substances. Suitable formulations for transdermal applications include an effective amount of a compound of the present application with a carrier. A carrier can include absorbable pharmacologically acceptable solvents to assist passage through the skin of the host. For example, transdermal devices are in the form of a bandage comprising a backing member, a reservoir containing the compound optionally with carriers, optionally a rate controlling barrier to deliver the compound to the skin of the host at a controlled and predetermined rate over a prolonged period of time, and means to secure the device to the skin. Matrix transdermal formulations may also be used. Suitable formulations for topical application, e.g., to the skin and eyes, are preferably aqueous solutions, ointments, creams or gels well-known in the art. Such may contain solubilizers, stabilizers, tonicity enhancing agents, buffers and preservatives.

The pharmaceutical compositions of the present application comprise a therapeutically effective amount of a compound of the present application formulated together with one or more pharmaceutically acceptable carriers. As used herein, the term "pharmaceutically acceptable carrier" means a non-toxic, inert solid, semi-solid or liquid filler, diluent, encapsulating material or formulation auxiliary of any type. The pharmaceutical compositions of this application can be administered to humans and other animals orally, rectally, parenterally, intracisternally, intravaginally, intraperitoneally, topically (as by powders, ointments, or drops), buccally, or as an oral or nasal spray.

Liquid dosage forms for oral administration include pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

In order to prolong the effect of a drug, it is often desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Compositions for rectal or vaginal administration are preferably suppositories which can be prepared by mixing a compound of this application with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid compositions of a similar type may also be employed as fillers in soft and hard filled gelatin capsules using such excipients as lactose or milk sugar as well as high molecular weight polyethylene glycols and the like.

The active compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents.

Dosage forms for topical or transdermal administration of a compound of this application include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, eye ointments, powders and solutions are also contemplated as being within the scope of this application.

The ointments, pastes, creams and gels may contain, in addition to an active compound of this application, excipients such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to a compound of this application, excipients such as lactose, talc, silicic acid, aluminum hydroxide, calcium silicates and polyamide powder, or mixtures of these substances. Sprays can additionally contain customary propellants such as chlorofluorohydrocarbons.

Transdermal patches have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

According to the methods of treatment of the present application, disorders are treated or prevented in a subject, such as a human or other animal, by administering to the subject a therapeutically effective amount of a compound of the application, in such amounts and for such time as is necessary to achieve the desired result. The term "therapeutically effective amount" of a compound of the application, as used herein, means a sufficient amount of the compound so as to decrease the symptoms of a disorder in a subject. As is well understood in the medical arts a therapeutically effective amount of a compound of this application will be at a reasonable benefit/risk ratio applicable to any medical treatment.

In general, a compound of the application will be administered in therapeutically effective amounts via any of the usual and acceptable modes known in the art, either singly or in combination with one or more therapeutic agents. A therapeutically effective amount may vary widely depending on the severity of the disease, the age and relative health of the subject, the potency of the compound used and other factors. Therapeutic amounts or doses will also vary depending on route of administration, as well as the possibility of co-usage with other agents.

Upon improvement of a subject's condition, a maintenance dose of a compound, composition or combination of this application may be administered, if necessary. Subsequently, the dosage or frequency of administration, or both, may be reduced, as a function of the symptoms, to a level at which the improved condition is retained when the symptoms have been alleviated to the desired level, treatment should cease. The subject may, however, require intermittent treatment on a long-term basis upon any recurrence of disease symptoms.

It will be understood, however, that the total daily usage of the compounds and compositions of the present application will be decided by the attending physician within the scope of sound medical judgment. The specific inhibitory dose for any particular patient will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts.

The term "pharmaceutical combination" as used herein means a product that results from the mixing or combining of more than one active ingredient and includes both fixed and non-fixed combinations of the active ingredients. The term "fixed combination" means that the active ingredients, e.g., a compound of the application and a co-agent, are both administered to a patient simultaneously in the form of a single entity or dosage. The term "non-fixed combination" means that the active ingredients, e.g., a compound of the application and a co-agent, are both administered to a patient as separate entities either simultaneously, concurrently or sequentially with no specific time limits, wherein such administration provides therapeutically effective levels of the two compounds in the body of the patient. The latter also applies to cocktail therapy, e.g., the administration of three or more active ingredients.

Some examples of materials which can serve as pharmaceutically acceptable carriers include, but are not limited to, ion exchangers, alumina, aluminum stearate, lecithin, serum proteins, such as human serum albumin, buffer substances such as phosphates, glycine, sorbic acid, or potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, polyacrylates, waxes, polyethylenepolyoxypropylene-block polymers, wool fat, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes, oils such as peanut oil, cottonseed oil; safflower oil; sesame oil; olive oil; corn oil and soybean oil; glycols; such a propylene glycol or polyethylene glycol; esters such as ethyl oleate and ethyl laurate, agar; buffering agents such as magnesium hydroxide and aluminum hydroxide; alginic acid; pyrogen-free water, isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator. The protein kinase inhibitors or pharmaceutical salts thereof may be formulated into pharmaceutical compositions for administration to animals or humans. These pharmaceutical compositions, which comprise an amount of the protein inhibitor effective to treat or prevent a protein kinase-mediated condition and a pharmaceutically acceptable carrier, are other embodiments of the present application.

In another aspect, the application provides a kit comprising a compound capable of inhibiting kinase activity selected from one or more compounds of disclosed herein, or a pharmaceutically acceptable salt, hydrate, solvate, prodrug, stereoisomer, or tautomer thereof, and instructions for use in treating cancer.

In another aspect, the application provides a kit comprising a compound capable of inhibiting ALK activity selected from a compound disclosed herein, or a pharmaceutically acceptable salt, hydrate, solvate, prodrug, stereoisomer, or tautomer thereof.

In a further aspect, the application provides a kit comprising a compound capable of inhibiting SRPK (e.g., SRPK1 and/or SRPK2) activity selected from a compound disclosed herein, or a pharmaceutically acceptable salt, hydrate, solvate, prodrug, stereoisomer, or tautomer thereof.

The application is further illustrated by the following examples and synthesis schemes, which are not to be construed as limiting this application in scope or spirit to the specific procedures herein described. It is to be understood that the examples are provided to illustrate certain embodiments and that no limitation to the scope of the application is intended thereby. It is to be further understood that resort may be had to various other embodiments, modifications, and equivalents thereof which may suggest themselves to those skilled in the art without departing from the spirit of the present application and/or scope of the appended claims.

EXAMPLES

Analytical Methods, Materials, and Instrumentation

All reactions were monitored by thin layer chromatography (TLC) with 0.25 mm E. Merck pre-coated silica gel plates (60 $F_{254}$) and Waters LCMS system (Waters 2489 UV/Visible Detector, Waters 3100 Mass, Waters 515 HPLC pump, Waters 2545 Binary Gradient Module, Waters Reagent Manager, Waters 2767 Sample Manager) using SunFire™ $C_{18}$ column (4.6×50 mm, 5 μm particle size): solvent gradient=100% A at 0 min, 1% A at 5 min; solvent A=0.035% TFA in Water; solvent B=0.035% TFA in $CH_3CN$; flow rate: 2.5 mL/min. Purification of reaction products was carried out by flash chromatography using CombiFlash®Rf with Teledyne Isco RediSep®Rf High Performance Gold or Silicycle SiliaSep™ High Performance columns (4 g, 12 g, 24 g, 40 g, 80 g, or 120 g).

The purity of all compounds was over 95% and was analyzed with Waters LCMS system. $^1$HNMR and $^{13}$C NMR spectra were obtained using a Varian Inova-400 (400 MHz for 1H, and 75 MHz for 13C) spectrometer. Chemical shifts are reported relative to chloroform (δ=7.24) for $^1$H NMR or dimethyl sulfoxide (δ=2.50) for $^1$H NMR and dimethyl sulfoxide (δ=39.51) for $^{13}$C NMR. Data are reported as (br=broad, s=singlet, d=doublet, t=triplet, q=quartet, m=multiplet).

Abbreviations used in the following examples and elsewhere herein are:
atm atmosphere
br broad
DIPEA N,N-diisopropylethylamine
DMF N,N-dimethylformamide
DMSO dimethyl sulfoxide
DIEA diisopropylethylamin
EtOAc ethyl acetate
HCl hydrochloric acid
h hour(s)
HATU bis(dimethylamino)methylene]-1H-1,2,3-triazolo[4,5-b]pyridinium 3-oxide hexafluoro-phosphate
HPLC high-performance liquid chromatography
LCMS liquid chromatography—mass spectrometry
m multiplet
MeOH methanol
MHz megahertz
min minutes
MS mass spectrometry
NMR nuclear magnetic resonance
$Pd_2(dba)_3$ tris(dibenzylideneaceione)dipaliadium(0)
$Pd(dppf)Cl_2$ bis(diphenylphosphino)ferrocene]palladium (II) dichloride
ppm parts per million
THF tetrahydrofuran
TLC thin layer chromatography
TBAF tetra-n-butylammonium fluoride
Xphos 2-dicyclohexylphosphino-2",4",6"-triisopropylbiphenyl Example 1: Synthesis of 9-ethyl-6,6-dimethyl-8-(1-methyl-1H-pyrazol-4-yl)-11-oxo-6,11-dihydro-5H-benzo[b]carbazole-3-carbonitrile (Compound 7)

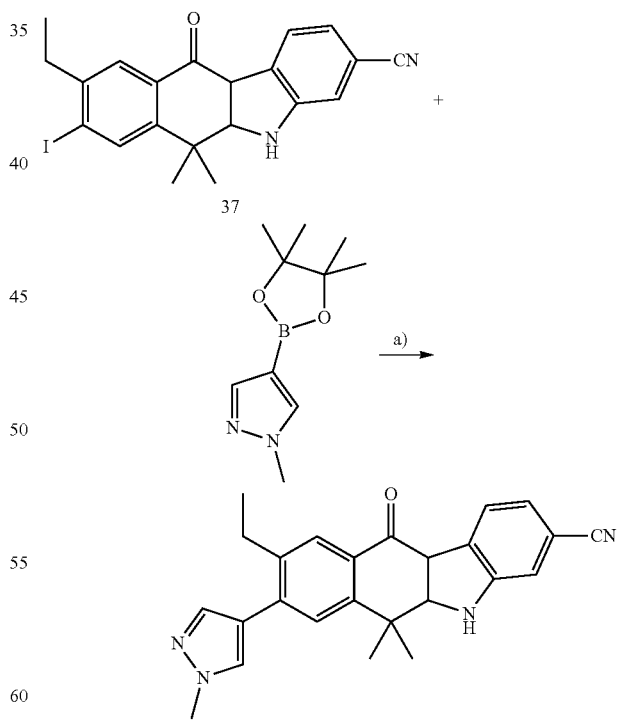

1-methyl-4-(4,4,5,5-tetramethyl-1,3,2-dioxaborolan-2-yl)-1H-pyrazole (34 mg, 0.16 mmol) and 37 (60 mg, 0.13 mmol) were dissolved in 1,4-dioxane (5 mL) and 2M $Na_2CO_3$ sat. aq. solution (0.17 mL, 0.34 mmol) and thoroughly degassed. Pd(dppf)C₁₂ (6 mg, 0.008 mmol) and t-Butyl XPhos (4 mg, 0.005 mmol) were added and mixture was heated to 100° C. in a sealed vial. After stirring for 1 hour, LC-MS analysis indicated the reaction was finished. The reaction mixture was filtered through celite and purified by reversed-phase HPLC using a gradient of 30-100% CH₃CN/H₂O with 0.035% TFA to give the desired compound as a beige solid. ¹H NMR (DMSO-d6, 400 MHz) δ 12.75 (s, 1H), 8.35 (d, J=8 Hz, 1H), 8.11 (s, 1H) 8.07 (s, 1H), 8.01 (S, 1H), 7.79 (d, J=8 Hz, 2H), 7.63 (d, J=8 Hz, 2H), 3.93 (s, 3H), 2.82 (q, J=7.2 Hz, 2H) 1.79 (s, 6H), 1.17 (t, J=7.2 Hz, 3H), MS m/z 395.73 [M+1].

Example 2: Synthesis of 8-(4-(dimethylamino)piperidin-1-yl)-9-ethyl-6,6-dimethyl-11-oxo-6,11-dihydro-5H-benzo[b]carbazole-3-carbonitrile (Compound 17)

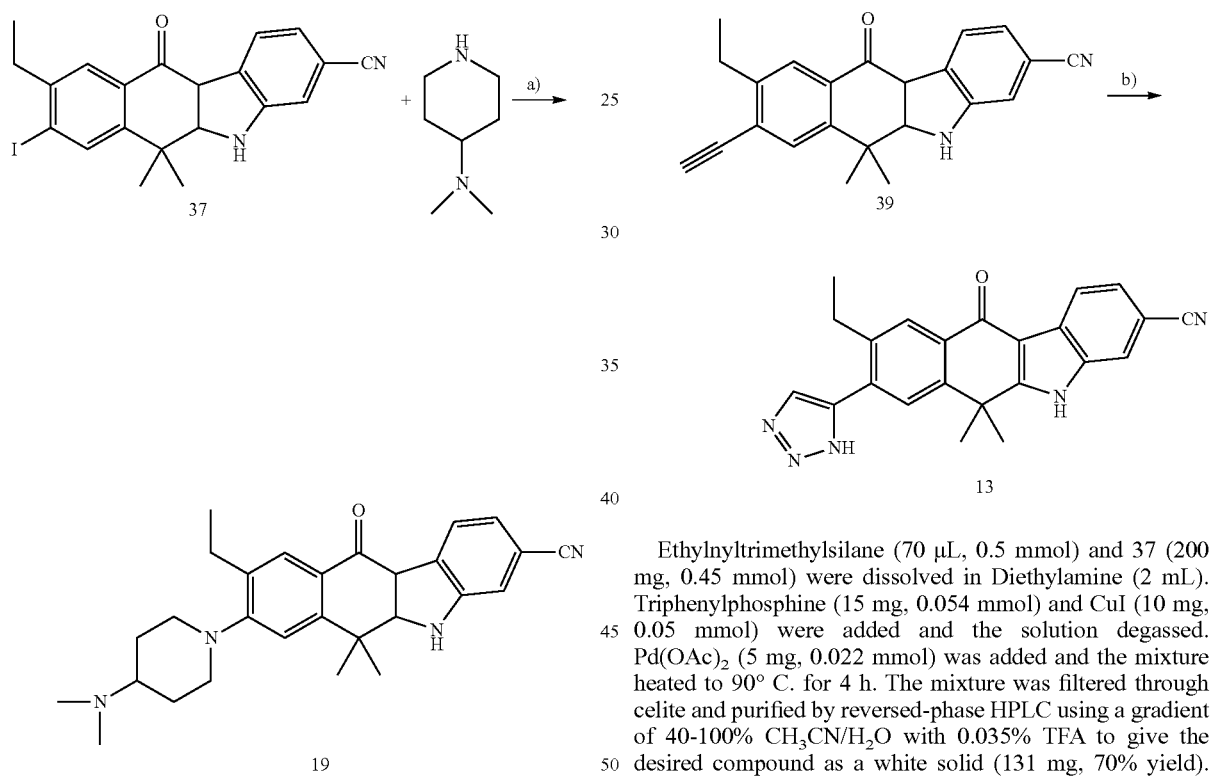

N,N-dimethylpiperidin-4-amine (30 mg, 0.15 mmol), NaOt-Bu (70 mg, 0.73 mmol) and 37 (40 mg, 0.09 mmol) were dissolved in 1,4-Dioxane (3 mL), and the mixture thoroughly degassed. Pd2(dba)₃ (5 mg, 0.05 mmol) and tri(o-tolyl) (3 mg, 0.09 mmol) were added. The mixture was heated to 110° C. for 4 hours. LC-MS analysis showed conversion to the desired product. The mixture was filtered and purified by reversed-phase HPLC using a gradient of 10-60% CH₃CN/H₂O with 0.035% TFA to give the desired compound as a brown solid (18 mg, 45% yield). ¹H NMR (DMSO-d6, 400 MHz) δ 12.76 (s, 1H), 8.31 (d, J=8 Hz, 2H), 8.04 (s, 1H) 7.98 (s, 1H), 7.58 (d, J=8 Hz, 1H), 7.34 (s, 1H), 6.51 (s, 1H), 4.07 (m, 4H), 2.80 (s, 6H), 3.14 (m, 4H), 2.71 (q, J=7.2 Hz, 2H) 1.74 (s, 6H), 1.23 (t, J=8 Hz, 3H), MS m/z 382.43 [M+1].

Example 3: Synthesis of 9-ethyl-6,6-dimethyl-11-oxo-8-(1H-1,2,3-triazol-5-yl)-6,11-dihydro-5H-benzo[b]carbazole-3-carbonitrile (Compound 13)

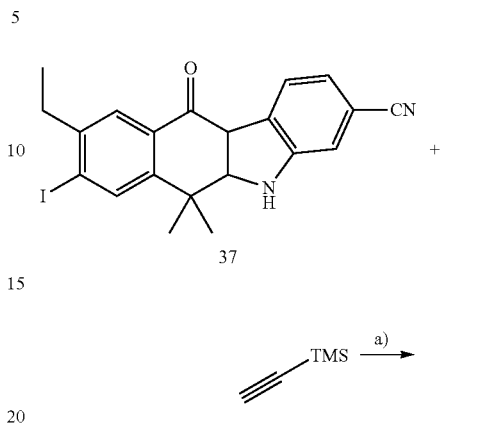

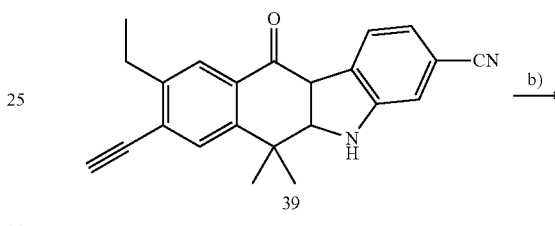

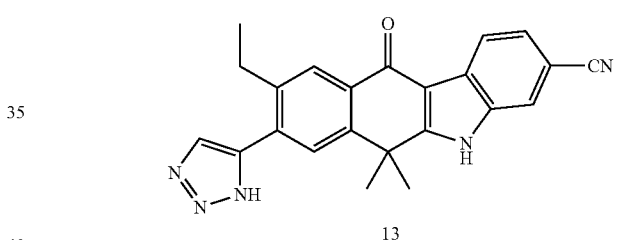

Ethylnyltrimethylsilane (70 μL, 0.5 mmol) and 37 (200 mg, 0.45 mmol) were dissolved in Diethylamine (2 mL). Triphenylphosphine (15 mg, 0.054 mmol) and CuI (10 mg, 0.05 mmol) were added and the solution degassed. Pd(OAc)₂ (5 mg, 0.022 mmol) was added and the mixture heated to 90° C. for 4 h. The mixture was filtered through celite and purified by reversed-phase HPLC using a gradient of 40-100% CH₃CN/H₂O with 0.035% TFA to give the desired compound as a white solid (131 mg, 70% yield). This material was dissolved in THF (5 mL) and TBAF 1M in THF (0.95 mL, 0.95 mmol) was added. The mixture was stirred for 5 h at rt. The reaction was quenched with water and extracted with EtOAc (3×50 mL) washed with brine, dried over MgSO₄, and condensed to give the alkyne as a white solid in quantitative yield. TMS-Azide (30 μL, 0.22 mmol) was added to a solution of the alkyne 39 (50 mg, 0.15 mmol) and CuI (3 mg, 0.007 mmol) in a 9:1 mixture of DMF/MeOH (1 mL) and stirred at 100° C. for 4 h. The mixture was filtered through celite and purified by reversed-phase HPLC using a gradient of 40-100% CH₃CN/H₂O with 0.035% TFA to give the desired compound as a white solid (20 mg, 36% yield). ¹H NMR (DMSO-d6, 400 MHz) δ 13.15 (s, 1H), 12.06 (br, 1H), 8.31 (d, J=8 Hz, 1H), 8.11 (s, 1H) 8.04 (s, 1H), 7.95 (s, 1H), 7.71 (s, 1H), 7.60 (d, J=7.2 Hz, 1H), 2.91 (q, J=7.2 Hz, 2H) 1.81 (s, 6H), 1.17 (t, J=7.2 Hz, 3H), MS m/z 382.19 [M+1].

Example 4: Synthesis of (R)-8-(1,2-dihydroxy-ethyl)-9-ethyl-6,6-dimethyl-11-oxo-6,11-dihydro-5H-benzo[b]carbazole-3-carbonitrile (Compound 22)

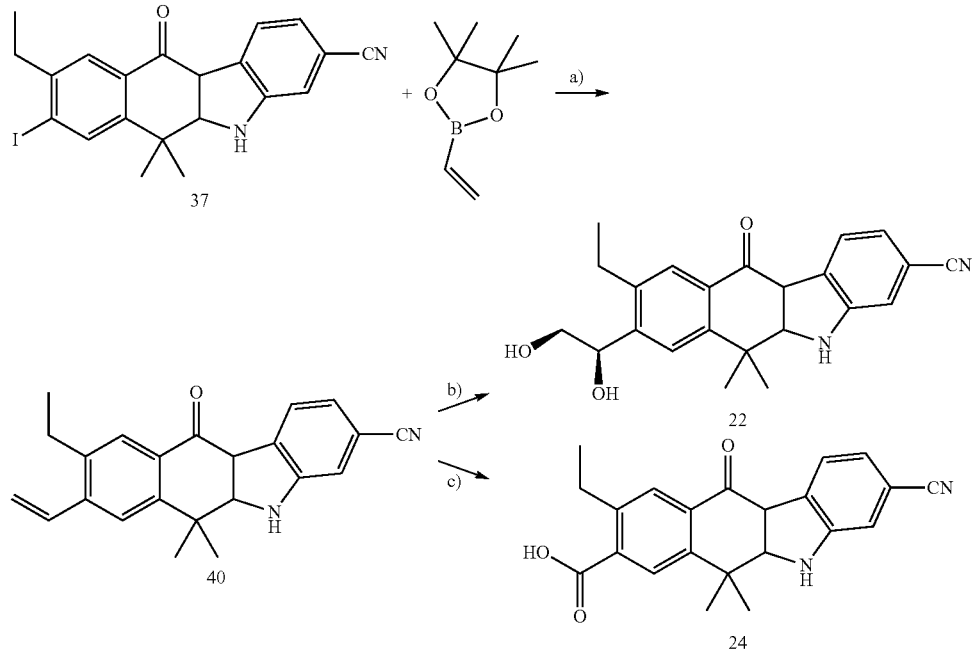

Step 1. 9-ethyl-6,6-dimethyl-11-oxo-8-vinyl-6,11-dihydro-5H-benzo[b]carbazole-3-carbonitrile (40)

The procedure used to prepare Compound 7 was used to prepare Compound 40 (32 mg, 68% yield).

Step 2. (R)-8-(1,2-dihydroxyethyl)-9-ethyl-6,6-dimethyl-11-oxo-6,11-dihydro-5H-benzo[b]carbazole-3-carbonitrile (Compound 22)

AD-mix 13 (206 mg) and Compound 40 (50 mg, 0.15 mmol) were dissolved in a 0° C. solution of $H_2O$ (3 mL) and t-BuOH. The mixture was slowly warmed to rt and stirred for 12 h at rt. LC-MS analysis showed complete conversion of the starting material to the desired product. The reaction mixture was filtered and purified by reversed-phase HPLC using a gradient of 20-70% $CH_3CN/H_2O$ with 0.035% TFA to give the desired compound as a white solid (28 mg, 51% yield). $^1$H NMR (DMSO-d6, 400 MHz) δ 12.75 (s, 1H), 8.32 (d, J=8 Hz, 1H), 7.99 (m, 2H), 7.85 (s, 1H), 7.63 (d, J=8 Hz, 1H), 5.38 (d, J=4 Hz, 1H), 4.87 (m, 2H), 3.48 (m, 2H), 2.75 (m, 2H), 1.75 (s, 6H), 1.25 (t, J=7 Hz, 3H), MS m/z 375.74 [M+1].

Example 5: Synthesis of the Compounds of the Present Application

The following compounds in Table 1 were synthesized according to the procedures outlined in Examples 1-4.

TABLE 1

| Cmpd No. | MS (m/z) and/or $^1$H NMR data |
|---|---|
| 6 | MS m/z 466.19 [M + 1]; $^1$H NMR (DMSO-d6, 400 MHz) δ 12.77 (s, 1H), 8.57 (S, 1H), 8.34 (d, J = 8 Hz, 1H), 8.13 (d, J = 8 Hz, 2H), 8.02 (s, 1H), 7.86 (S, 1H), 7.64 (d, J = 8 Hz, 1H), 5.21 (s, 2H), 3.01 (s, 3H), 2.89 (s, 3H), 2.83 (q, J = 8 Hz, 2H), 1.80 (s, 6H), 1.22 (t, J = 8 Hz, 3H); $^{13}$C NMR 100 MHz (DMSO-d6) δ 179.61, 167.01, 160.63, 147.78, 146.10, 139.58, 138.93, 136.61, 136.16, 131.37, 129.83, 128.13, 127.3, 126.22, 125.33, 122.09, 120.42, 116.85, 109.97, 105.15, 53.34, 36.74, 36.36, 35.68, 30.39, 26.32, 15.27. |
| 8 | MS m/z 381.65 [M + 1]; $^1$H NMR (DMSO-d6, 400 MHz) δ 13.6 (s, 1H), 8.34 (d, J = 8 Hz, 1H), 8.11 (s, 1H) 8.01 (s, 1H), 7.97 (s, 1H), 7.78 (s, 1H), 7.60 (d, J = 7.2 Hz, 1H), 3.46 (br, 1H), 2.85 (q, J = 7.2 Hz, 2H) 1.79 (s, 6H), 1.22 (t, J = 7.2 Hz, 3H). |
| 9 | MS m/z: 381.73 (M + 1); $^1$H NMR (DMSO-d6, 400 MHz) δ 12.78 (s, 1H), 8.33 (d, J = 8 Hz, 1H), 8.14 (s, 1H), 8.01 (d, J = 8 Hz, 2H), 7.83 (s, 1H), 7.76 (s, 1H), 7.64 (d, J = 8 Hz, 1H), 6.89 (m, 1H), 2.81 (q, J = 8 Hz, 2H), 1.85 (s, 6H), 1.21 (t, J = 8 Hz, 3H). |
| 10 | MS m/z: 382.43 [M + 1]; $^1$H NMR (DMSO-d6, 400 MHz) δ 12.87 (s, 1H), 9.25 (s, 1H), 9.02 (s, 1H), 8.31 (d, J = 8 Hz, 1H), 8.13 (s, 1H) 7.98 (s, 1H), 7.84 (S, |

TABLE 1-continued

| Cmpd No. | MS (m/z) and/or ¹H NMR data |
|---|---|
| | 1H), 7.6 (d, J = 8 Hz, 1H), 2.75 (q, J = 7.2 Hz, 2H) 1.76 (s, 6H), 1.17 (t, J = 8 Hz, 3H). |
| 11 | MS m/z: 381.48 (M + 1); ¹H NMR (DMSO-d6, 400 MHz) δ 12.81 (s, 1H), 8.34 (d, J = 8 Hz, 1H), 8.15 (s, 1H), 7.96 (s, 1H), 7.90, (s, 1H), 7.70 (s, 1H), 7.61 (d, J = 8 Hz, 1H), 7.43 (d, J = 8 Hz, 1H), 7.32 (d, J = 6 Hz, 1H), 2.81 (q, J = 8 Hz, 2), 1.81 (s, 6H), 1.26 (t, J = 8 Hz, 3H). |
| 12 | MS m/z: 397.26 (M + 1); ¹H NMR (DMSO-d6, 400 MHz) δ 12.78 (s, 1H), 8.36 (d, J = 8 Hz, 1H), 8.15 (s, 1H), 8.02 (s, 1H), 7.71 (m, 2H), 7.65 (m, 2H), 7.32 (d, J = 6 Hz, 1H), 2.81 (q, J = 8 Hz, 2H), 1.78 (s, 6H), 1.21 (t, J = 8 Hz, 3H). |
| 14 | MS m/z 392.31 [M + 1]; ¹H NMR (DMSO-d6, 400 MHz) δ 12.88 (s, 1H), 8.85 (m, 2H), 8.36 (d, J = 8 Hz, 1H), 8.23 (s, 1H) 8.04 (s, 1H), 7.78 (s, 1H), 7.65 (d, J = 7.2 Hz, 1H), 2.70 (q, J = 8 Hz, 2H) 1.79 (s, 6H), 1.13 (t, J = 8 Hz, 3H). |
| 15 | MS m/z 392.48 [M + 1]; ¹H NMR (DMSO-d6, 400 MHz) δ 12.85 (s, 1H), 8.78 (m, 2H), 8.36 (d, J = 8 Hz, 1H), 8.22 (s, 1H), 8.13 (d, J = 8 Hz, 1H), 8.03 (s, 1H), 7.77 (s, 1H), 7.73 (m, 1H), 7.65 (d, J = 7.2 Hz, 1H), 2.66 (q, J = 8 Hz, 2H) 1.79 (s, 6H), 1.13 (t, J = 8 Hz, 3H). |
| 16 | MS m/z 393.71 [M + 1]; ¹H NMR (DMSO-d6, 400 MHz) δ 12.83 (s, 1H), 9.28 (s, 1H), 8.95 (s, 2H), 8.36 (d, J = 8 Hz, 1H), 8.22 (s, 1H), 8.03 (s, 1H), 7.84 (s, 1H), 7.64 (d, J = 7.2 Hz, 1H), 2.67 (q, J = 8 Hz, 2H) 1.8 (s, 6H), 1.13 (t, J = 7.2 Hz, 3H). |
| 18 | MS m/z 399.69 [M + 1]; ¹H NMR (DMSO-d6, 400 MHz) δ 12.81 (s, 1H), 8.29 (d, J = 8 Hz, 1H), 8.06 (s, 1H) 7.98 (s, 1H), 7.59 (d, J = 7 Hz, 1H), 7.35 (s, 1H), 3.14 (m, 4H), 2.71 (q, J = 7.2 Hz, 2H), 2.49 (m, 4H), 1.74 (s, 6H), 1.25 (t, J = 8 Hz, 3H). |
| 19 | MS m/z 413.27 [M + 1]; ¹H NMR (DMSO-d6, 400 MHz) δ 12.75 (s, 1H), 8.27 (d, J = 8 Hz, 1H), 8.06 (s, 1H) 7.96 (s, 1H), 7.58 (d, J = 7 Hz, 1H), 7.35 (s, 1H), 3.21 (m, 4H), 2.71 (q, J = 7.2 Hz, 2H), 2.10 (m, 4H), 1.76 (s, 6H), 1.17 (t, J = 8 Hz, 3H). |
| 20 | MS m/z 400.49 [M + 1]; ¹H NMR (DMSO-d6, 400 MHz) δ 12.76 (s, 1H), 8.31 (d, J = 8 Hz, 1H), 8.02 (s, 1H) 7.97 (s, 1H), 7.76 (d, J = 8 Hz, 1H), 7.58 (s, 1H), 7.34 (S, 1H), 3.78 (m, 2H), 2.98 (m, 2H) 2.71 (q, J = 7.2 Hz, 2H) 1.76 (s, 6H), 1.23 (t, J = 8 Hz, 3H). |
| 21 | MS m/z 340.53 [M + 1]; ¹H NMR (DMSO-d6, 400 MHz) δ 12.92 (s, 1H), 8.44 (s, 1H), 8.33 (d, J = 8 Hz, 1H), 8.24 (s, 1H) 8.05 (s, 1H), 7.66 (d, J = 8 Hz, 1H), 2.92 (q, J = 7.2 Hz, 2H), 1.79 (s, 6H), 1.31 (t, J = 8 Hz, 3H). |
| 22 | MS m/z 375.74 [M + 1]; ¹H NMR (DMSO-d6, 400 MHz) δ 12.75 (s, 1H), 8.32 (d, J = 8 Hz, 1H), 7.99 (m, 2H), 7.85 (s, 1H), 7.63 (d, J = 8 Hz, 1H), 5.38 (d, J = 4 Hz, 1H), 4.87 (m. 2H), 3.48 (m, 2H), 2.75 (m, 2H), 1.75 (s, 6H), 1.25 (t, J = 7 Hz, 3H). |
| 23 | MS m/z 375.68 [M + 1]; ¹H NMR (DMSO-d6, 400 MHz) δ 12.82 (s, 1H), 8.34 (d. J = 8 Hz, 1H), 8.03 (m, 2H), 7.85 (s, 1H), 7.63 (d, J = 8 Hz, 1H), 5.40 (d, J = 4 Hz, 1H), 4.78 (m, 2H), 3.69 (m, 2H), 2.68 (m, 2H), 1.81 (s, 6H), 1.13 (t, J = 7 Hz, 3H). |
| 24 | MS m/z 359.43 [M + 1]; ¹H NMR (DMSO-d6, 400 MHz) δ 12.89 (s, 1H), 8.34 (d, J = 8 Hz, 1H), 8.13 (d, J = 8 Hz, 2H), 8.03 (s, 1H), 7.64 (d, J = 8 Hz, 1H), 2.98 (q, J = 7.2 Hz, 2H) 1.76 (s, 6H), 1.23 (t, J = 8 Hz, 3H). |
| 25 | MS m/z: 440.84 [M + 1]; ¹H NMR (DMSO-d6, 400 MHz) δ 12.82 (s, 1H), 8.30 (d, J = 8 Hz, 1H), 8.03 (m, 3H), 8.03 (s, 1H), 7.64 (d, J = 8 Hz, 1H), 7.19 (d, J = 16 Hz, 1H), 6.48 (m, 1H), 3.99 (m 4H), 2.80 (q, J = 8 Hz, 2H) 1.79 (s, 6H), 1.20 (t, J = 7.2 Hz, 3H). |
| 26 | MS m/z 408.29 [M + 1]; ¹H NMR (DMSO-d6, 400 MHz) δ 12.88 (s, 1H), 8.34 (d, J = 8 Hz, 1H), 8.18 (s, 1H), 8.06 (d, J = 7 Hz, 2H), 7.98 (d, J = 8 Hz, 1H), 7.89 (br, 1H), 7.73 (s, 1H), 7.64 (d, J = 8 Hz, 1H), 7.03 (d, J = 8 Hz, 1H), 2.68 (q, J = 7.2 Hz, 2H), 1.78 (s, 6H), 1.18 (t, J = 7 Hz, 3H). |
| 27 | MS m/z 407.72 [M + 1]; ¹H NMR (DMSO-d6, 400 MHz) δ 12.78 (s, 1H), 11.84 (br, 1H), 8.36 (d, J = 8 Hz, 1H), 8.14 (s, 1H), 7.67 (s, 1H), 7.63 (d, J = 8 Hz, 1H), 7.55 (d, J = 7.2 Hz, 1H), 7.46 (s, 1H), 6.46 (d, J = 8.2 Hz, 1H), 2.69 (q, J = 8 Hz, 2H), 1.78 (s, 6H), 1.17 (t, J = 7 Hz, 3H). |
| 28 | MS m/z: 415.33 [M + 1]; ¹H NMR (400 MHz, DMSO-d₆) δ 12.78 (br, 1H), 8.29 (d, J = 4 Hz, 1H), 8.05 (s, 1H), 7.99 (s, 1H), 7.58 (d, J = 7.2 Hz, 1H), 7.47 (s, 1H), 2.8 (s, 3H), 2.73 (m, 5H), 2.48 (s, 6H), 2.73 (m, 5H), 1.79 (s, 6H), 0.88 (t, J = 8 Hz, 3H). |
| 29 | MS m/z 465.84 [M + 1]; ¹H NMR (DMSO-d6, 400 MHz) δ 12.76 (s, 1H), 8.34 (d, J = 8 Hz, 1H), 8.18 (s, 1H), 8.11 (S, 1H), 8.01 (S, 1H), 7.78 (d, J = 8 Hz, 2H), 7.62 (d, J = 8 Hz, 1H), 4.49 (q, J = 7.2 Hz, 1H), 3.98 (m, 4H), 3.50 (m 4H), 2.85 (q, J = 7.2 Hz, 2H), 1.76 (s, 6H), 1.23 (t, J = 8 Hz, 3H). |
| 30 | MS m/z 464.47 [M + 1]; ¹H NMR (DMSO-d6, 400 MHz) δ 12.82 (s, 1H), 8.33 (d, J = 8 Hz, 1H), 8.13 (d, J = 8 Hz, 2H), 8.03 (S, 1H), 7.87 (s, 1H), 7.79 (s, 1H), 7.63 (d, J = 8 Hz, 2H), 4.59 (m, 1H), 3.47 (m, 2H), 3.13 (m, 2H), 2.85 (q, J = 7.2 Hz, 2H), 2.26 (m, 4H), 1.79 (s, 6H), 1.23 (t, J = 8 Hz, 3H). |
| 31 | MS m/z: 452.57 [M + 1]; ¹H NMR (DMSO-d6, 400 MHz) δ 12.83 (s, 1H), 8.34 (d, J = 8 Hz, 1H), 8.22 (s, 1H), 8.14 (s, 1H), 8.03 (s, 1H), 7.95 (s, 1H), 7.78 (s, 1H), 7.63 (d, J = 8 Hz, 1H), 4.21 (m, 2H), 3.65 (m, 2H), 2.86 (s, 6H), 1.79 (s, 6H), 1.24 (t, J = 8 Hz, 3H). |
| 32 | MS m/z 466.37 [M + 1]; ¹H NMR (DMSO-d6, 400 MHz) δ 13.05 (s, 1H), 8.36 (d, J = 8 Hz, 1H), 8.18 (s, 1H), 8.11 (S, 1H), 8.15 (S, 1H), 8.06 (S, 1H), 7.90 (S, 1H), 7.82 (S, 1H), 7.62 (d, J = 8 Hz, 1H), 4.32 (m, 2H), 3.15 (m, 2H), 2.86 (m, 5H), 2.27 (m, 2H), 1.83 (s, 6H), 1.26 (t, J = 8 Hz, 3H); ¹³C NMR 100 MHz |

TABLE 1-continued

| Cmpd No. | MS (m/z) and/or $^1$H NMR data |
|---|---|
| | (DMSO-d$_6$) δ 179.61, 160.69, 150.93, 146.15, 139.55, 139.25, 136.12, 136.26, 130.09, 128.13, 127.41, 126.17, 125.25, 122.09, 120.52, 116.95, 109.94, 105.11, 54.78, 48.95, 42.70, 36.75, 30.35, 26.31, 25.38, 15.20. |
| 33 | MS m/z 452.59 [M + 1]; $^1$H NMR (DMSO-d6, 400 MHz) δ 12.87 (s, 1H), 8.51 (S, 1H), 8.31 (d, J = 8 Hz, 1H), 8.13 (d, J = 8 Hz, 2H), 8.02 (s, 1H), 7.86 (S, 1H), 7.64 (d, J = 8 Hz, 1H), 6.43 (s, 1H), 5.32 (s, 2H), 3.27 (s, 3H), 2.83 (q, J = 8 Hz, 2H), 1.80 (s, 6H), 1.22 (t, J = 8 Hz, 3H). |
| 34 | MS m/z: 438.59 [M + 1]; $^1$H NMR (DMSO-d6, 400 MHz) δ 12.86 (s, 1H), 8.63 (S, 1H), 8.25 (d, J = 8 Hz, 1H), 8.08 (d, J = 8 Hz, 2H), 7.96 (s, 1H), 7.87 (S, 1H), 7.64 (d, J = 8 Hz, 1H), 5.31 (s, 2H), 2.87 (q, J = 8 Hz, 2H), 1.77 (s, 6H), 1.18 (t, J = 8 Hz, 3H) |
| 35 | MS m/z: 494.61 [M + 1]; $^1$H NMR (DMSO-d6, 400 MHz) δ 12.76 (s, 1H), 8.33 (d, J = 8 Hz, 1H), 8.22 (s, 1H), 8.11 (s, 1H), 8.02 (s, 1H), 7.87 (s, 1H), 7.82 (s, 1H), 7.64 (d, J = 8 Hz, 1H), 2.85 (q, J = 8 Hz, 2H), 1.81 (s, 6H), 1.77 (s, 6H), 1.19 (t, J = 8 Hz, 3H). |
| 36 | MS m/z 452.68 [M + 1]; $^1$H NMR (DMSO-d6, 400 MHz) δ 12.77 (s, 1H), 8.52 (S, 1H), 8.34 (d, J = 8 Hz, 1H), 8.13 (d, J = 8 Hz, 2H), 8.02 (s, 1H), 7.86 (S, 1H), 7.63 (d, J = 8 Hz, 1H), 2.83 (q, J = 8 Hz, 2H), 2.51 (S, 6H), 1.85 (s, 6H), 1.22 (t, J = 8 Hz, 3H). |

Example 6: Biochemical Studies

Growth and inhibition of growth was assessed by MTS assay and was performed according to previously established methods (Zhou et al., Nature 2009). The MTS assay is a colorimetric method for determining the number of viable cells that is based on the bioreduction of MTS by cells to a formazan product that is soluble in cell culture medium and can be detected spectrophotometrically. Ba/F$_3$ cells of activated ALK and different ALK secondary mutations were exposed to treatment for 72 hours and the number of cells used per experiment determined empirically and has been previously established (Zhou et al., Nature 2009). All experimental points were set up in six wells and all experiments were repeated at least three times. The data was graphically displayed using GraphPad Prism version 5.0 for Windows, (GraphPad Software; www.graphpad.com). The curves were fitted using a nonlinear regression model with a sigmoidal dose response.

Example 7: Activities Against ALK Mutants in Comparison with Clinical ALK Inhibitors A compound of the present application, together with clinical ALK inhibitors, was tested against a panel of the most common secondary ALK mutants. EML4-ALK$^{WT}$ or secondary mutants transformed Ba/F$_3$ cells, or untransduced Ba/F$_3$ as cytotoxicity control, were treated with ALK inhibitors in a dose escalation MTS assay and assessed for viability after 72 hours. Average IC$_{50}$ values (nM) (n=3) are shown in Table 2. As shown in Table 2, the G1202R mutant confers resistance to all clinical stage ALK inhibitors. In contrast, Compound 6 displays potent activity against the G1202R mutant as well as the most common reported mutants.

Example 8: Activity Against G1202R Mutant ALK of the Compounds of the Present Application The compounds of the present application were tested against Ba/F$_3$ cells in a single point inhibition assay. EML4-ALK or EML4-ALK$^{G1202R}$ transformed Ba/F$_3$ cells or untransduced Ba/F$_3$ control were treated with a single dose (1 μM) of the compounds of the present application. Percent viability of untreated control for each compound was determined by MTS assay after 72 hours. The results are shown in Table 3.

TABLE 3

| Cmpd No. | wt | G1202R | Parental Ba/F3 |
|---|---|---|---|
| 6 | 0 | 0 | 71 |
| 7 | 1 | 1 | 65 |
| 8 | 0 | 1 | 17 |
| 9 | 1 | 1 | 17 |
| 10 | 2 | 3 | 121 |
| 11 | 6 | 8 | 112 |
| 12 | 12 | 10 | 41 |
| 13 | 6 | 7 | 88 |
| 14 | 2 | 5 | 132 |
| 15 | 1 | 3 | 81 |
| 16 | 3 | 4 | 150 |
| 17 | 2 | 9 | 18 |
| 18 | 1 | 7 | 74 |
| 19 | 0.1 | 0.1 | 37 |
| 20 | 2 | 4 | 68 |
| 21 | 19 | 28 | 70 |
| 22 | 4 | 39 | 54 |
| 23 | 4 | 53 | 59 |
| 24 | 57 | 39 | 68 |
| 25 | 93 | 103 | 120 |
| 26 | 4 | 12 | 5 |
| 27 | 12 | 42 | 62 |
| 28 | 2 | 7 | 83 |

TABLE 2

| | wt | C1156Y | F1174L | L1196M | L1152R | 1151 Tins | G1202R | G1269A | S1206Y | Untrans. |
|---|---|---|---|---|---|---|---|---|---|---|
| Alectinib | 2 | 2 | 3 | 90 | 169 | 72 | 207 | 9 | 2 | >10$^3$ |
| Ceritinib | 41 | 164 | 101 | 64 | 2747 | 668 | 444 | 57 | 33 | 5512 |
| Brigatinib | 5 | 3 | 12 | 3 | 2300 | 142 | 56 | 2 | 12 | 1921 |
| Crizotinib | 56 | 144 | 81 | 549 | 645 | 857 | 328 | 512 | 65 | 927 |
| PF-06463922 | 1.3 | 1.6 | 0.2 | 21 | 9.0 | 38 | 77 | 15 | 4.2 | N/A |
| Compound 6 | 2 | 2 | 2 | 58 | 196 | 107 | 2 | 3 | 2 | 591 |

TABLE 3-continued

| Cmpd No. | wt | G1202R | Parental Ba/F3 |
|---|---|---|---|
| 29 | 0 | 0.2 | 54 |
| 30 | 1 | 1 | 5 |
| 31 | 1 | 1 | 34 |
| 32 | 0 | 0 | 30 |
| 33 | 0 | 0 | 1 |
| 34 | 38 | 12 | 91 |
| 35 | 0 | 0 | 71 |
| 36 | 0 | 0 | 44 |

Example 9: Activities Against ALK Mutants of the Compounds of the Present Application Compounds that showed potent inhibition of the G1202R mutant without showing potent inhibition of untransduced Ba/F$_3$ cells in the single point inhibition assay were tested against a panel of the most common secondary ALK mutants. The compounds of the present application were tested against Ba/F$_3$ cells in a dose escalation MTS assay in EML4-ALK$^{WT}$ or secondary mutant transformed Ba/F$_3$ cells. Untransduced Ba/F$_3$ control was used as a cytotoxicity control. Viability of the cells was determined after 72 hours, and the IC$_{50}$'s (nM) were shown in Table 4.

Figure 4A:
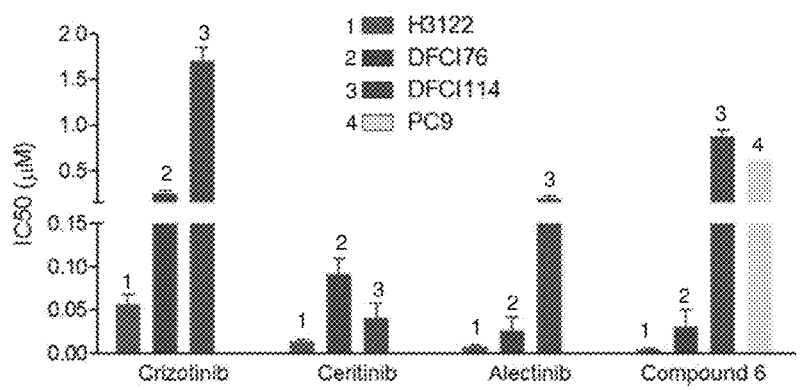
FIG. 4A is a series of bar graphs showing the IC$_{50}$'s of Crizotinib, Ceritinib, Alectinib, and Compound 6 against proliferation of an untransduced tumor cell line (H3122), the tumor cell line transduced with ALK mutant L1152R (DFCI76) or G1269A (DFCI114), and EGFR mutant cell line (PC9).
Figure 4B:
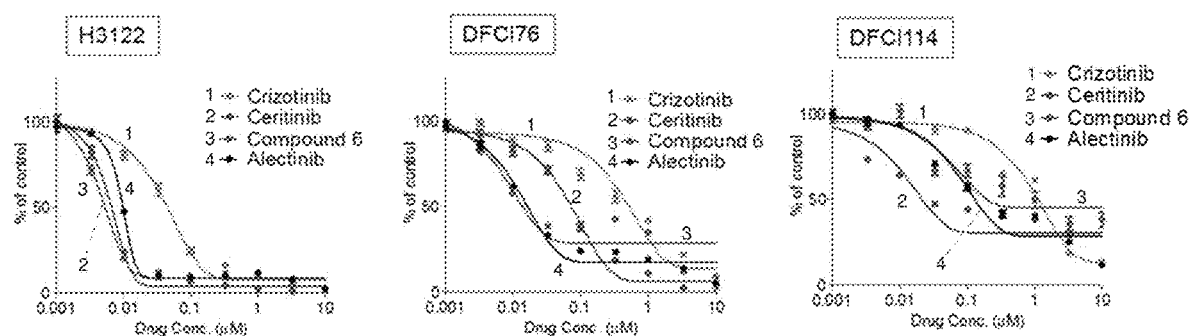
FIG. 4B is a series of graphs showing the viability (as a percentage of the control) of the cell lines H3122, DFCI76, and DFCI114 in FIG. 4A treated with increasing concentrations of Crizotinib, Ceritinib, Alectinib, and Compound 6.
Figure 5:
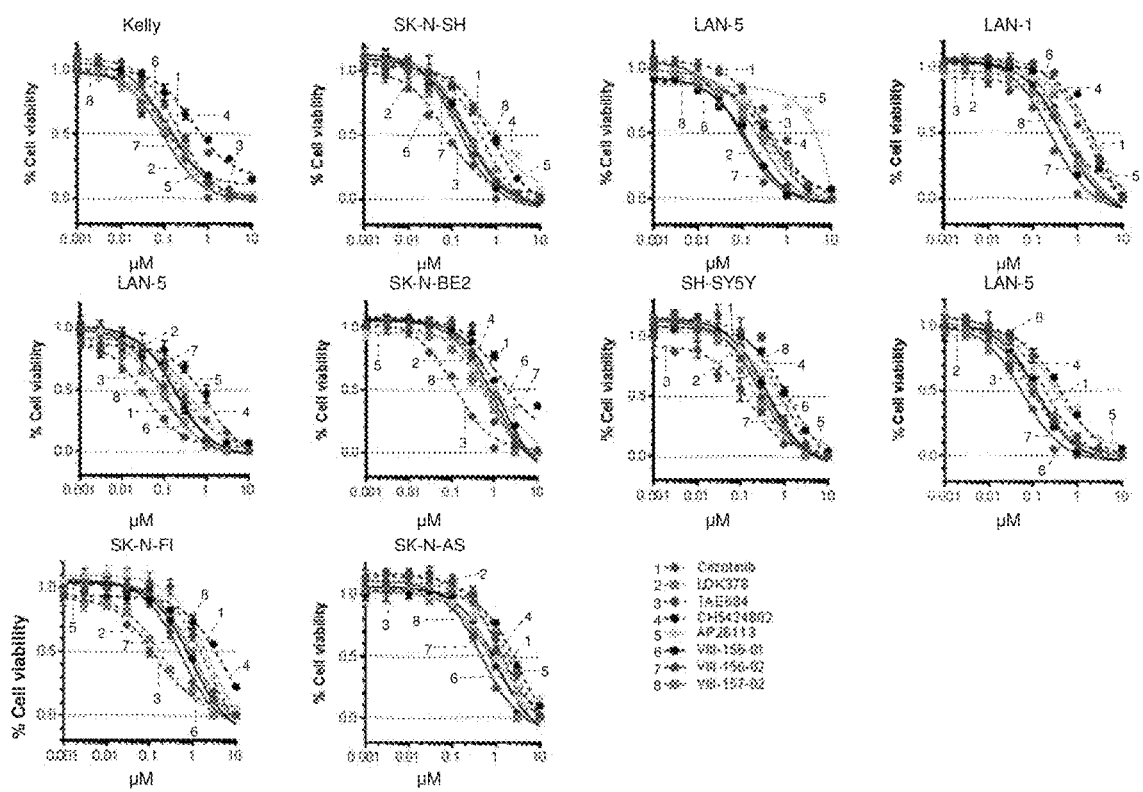
FIG. 5 is a series of graphs showing the viability of various cell lines transduced with ALK mutants treated with increasing concentrations of ALK inhibitors or Compound 6.

(H3122, DFCI76, and DFCI114), and neuroblastoma (Kelly, LAN-1, SH-SYSY (F1174L), SK-N-SH (F1174L), LAN-5 (R1275Q), SMS-KCNR (R1275Q), CHLA-20 (R1275Q), SK-N-BE2 (wt), SK-N-FI (wt), and SK-N-AS (wt) (Table 5 and FIGS. 4A, 4B, and 5).

Cells were seeded at 4000 per well in 96 well plates and exposed to each compound in triplicate at 1 nM to 10 μM for 72 hours. Cell viability was evaluated using CellTiter-Glo Luminescent Cell Viability Assay (Promega) following manufacturer's instruction. IC$_{50}$ values were calculated by nonlinear regression (variable slope) using GraphPad Prism 5 software. Each experiment was repeated for at least twice.

These selected cell lines showed varied patterns of sensitivity to the growth inhibitory activity of the compounds, which likely reflects a combination of the degree to which the antiproliferative activity is 'on-target' to ALK versus other targets of these compounds and the degree to which each of these cell lines are dependent upon ALK kinase activity. For example, Compounds 6 and 32 possessed submicromolar EC$_{50}$s across the entire panel of cell lines, and Compound 6 showed a marked increase in potency against all of the neuroblastoma cell lines and the ALK™ sensitive H3122 cells. The L1152R EML4-ALK mutant

TABLE 4

| Cmpd. | wt | C1156Y | F1174L | L1196M | L1152R | 1151Tins | G1202R | G1269A | S1206Y | Untrans. Ba/F3 |
|---|---|---|---|---|---|---|---|---|---|---|
| 6 | 2 | 2 | 2 | 58 | 196 | 107 | 2 | 3 | 2 | 591 |
| 7 | 61 | 150 | 84 | 370 | 5750 | 4409 | 21 | 200 | 104 | 1651 |
| 8 | 64 | 59 | 94 | 422 | 284 | 376 | 22 | 94 | 60 | 564 |
| 9 | 50 | 91 | 81 | 273 | 167 | 925 | 82 | 123 | 55 | 545 |
| 10 | 59 | 116 | 131 | 634 | 345 | 821 | 80 | 186 | 728 | 7324 |
| 13 | 115 | 177 | 188 | 629 | 345 | 53 | 214 | 256 | 1609 | 3014 |
| 17 | 2 | 2 | 2 | 10 | 695 | 203 | 478 | 3 | 2 | 6255 |
| 19 | 2 | 9 | 27 | 199 | 617 | 203 | 478 | 50 | 2 | 5646 |
| 29 | 78 | 58 | 105 | 535 | 781 | 620 | 20 | 177 | 53 | 924 |
| 30 | 40 | 24 | 87 | 262 | 297 | 161 | 37 | 146 | 29 | 768 |
| 31 | 2 | 24 | 54 | 80 | 548 | 77 | 8 | 11 | 6 | 1338 |
| 32 | 14 | 8 | 19 | 94 | 286 | 67 | 14 | 23 | 11 | 831 |
| 35 | 6 | 12 | 14 | 91 | 219 | 115 | 2 | 39 | 8 | 577 |
| 36 | 56 | 58 | 112 | 483 | 711 | 628 | 25 | 153 | 59 | 1647 |

Figure 6A:
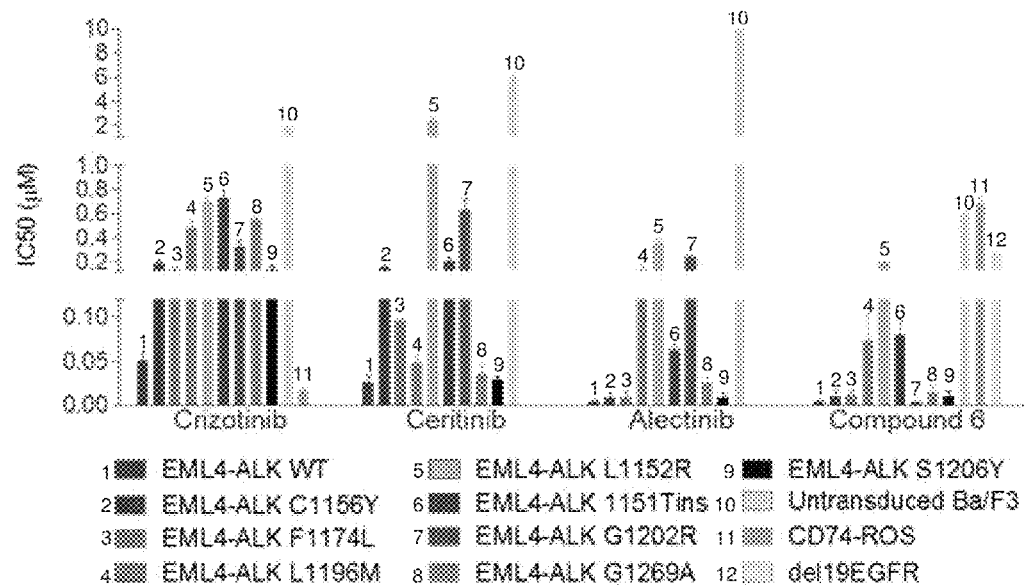
FIG. 6A is a series of bar graphs showing the IC$_{50}$'s of Crizotinib, Ceritinib, Alectinib, and Compound 6 against proliferation of an untransduced Ba/F3 cell line and Ba/F3 cell lines transduced with various ALK mutants or del19EGFR or CD74-ROS.
Figure 6B:
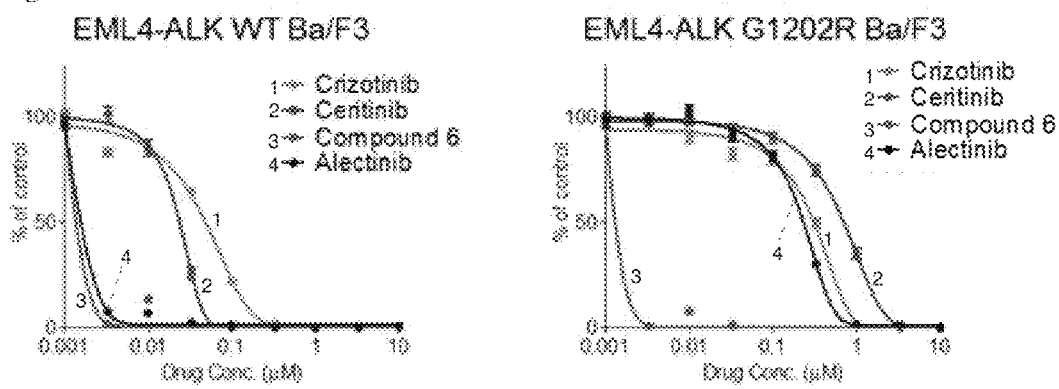
FIG. 6B is a series of graphs showing the viability (as a percentage of the control) of the cell lines in FIG. 6A treated with increasing concentrations of Crizotinib, Ceritinib, Alectinib, and Compound 6.
Figure 8:
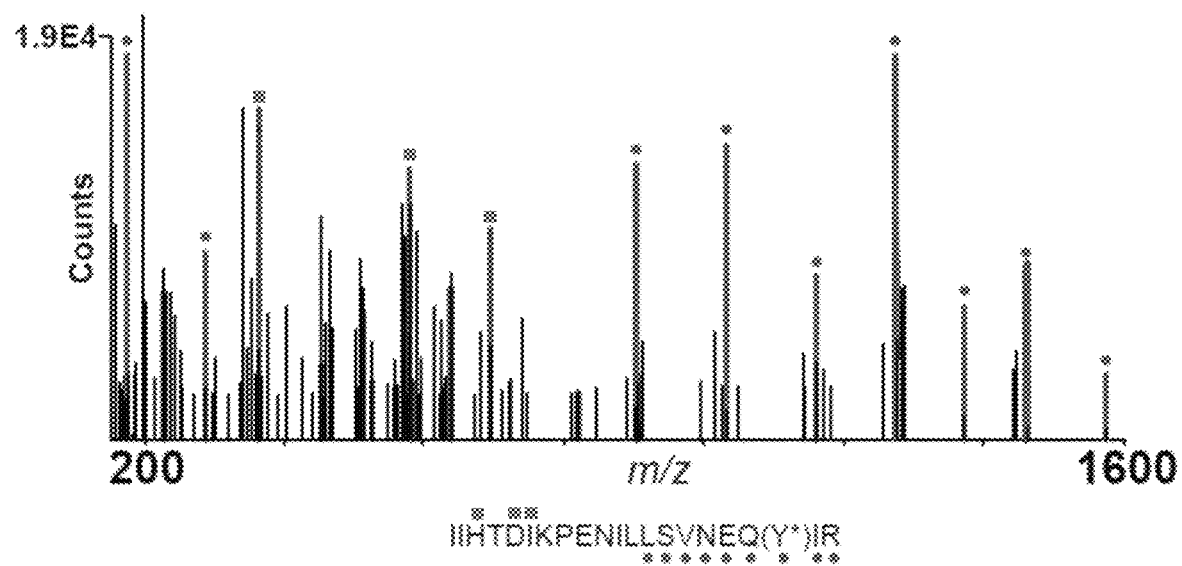
FIG. 8 shows the MS/MS spectrum of the tryptic SRPK1 peptide (residues 209-229) labeled at Y227 with Compound 37.

Example 10: Inhibition of Proliferation of Cells Bearing ALK Mutants by the Compounds of the Present Application The inhibitory activity of the compounds of the present application, as well as the clinical stage ALK inhibitors Alectinib, Ceritinib (LDK378), AP26113 (Brigatinib) and Crizotinib (Xalkori), were test against different ALK mutants in a panel of cell lines derived from NSCLC Ba/F$_3$ cells were more potently inhibited by Compound 6 than Alectinib (Table 5 and FIGS. 6A and 6B) possibly due to the fact that in DFCI76 the EML4-ALK activity of Compound 6 was masked by the activation of EGFR signaling, an additional known resistance mechanism in DFCI76. The mutant EGFR PC9 cell line was not inhibited by Compound 6, further demonstrating the on-target effect of this compound. Compound 32 was more potent in the neuroblastoma cell lines than Compound 6.

TABLE 5

EC$_{50}$'s of the compounds of the present application against a panel of NSCLC and neuroblastoma cell lines transduced with ALK mutants

| Cell Line | MYCN | Histology | EC$_{50}$(nM) | | | | | | |
|---|---|---|---|---|---|---|---|---|---|
| | | | 31 | 32 | 6 | Alectinib | LDK378 | AP26113 | Crizotinib |
| H3122 | | NSCL | 13 | 9 | 5 | 9 | 15 | 5 | 32 |
| DFCI76 (L1152R) | | NSCL | 45 | 30 | 19 | 511 | 72 | 30 | 233 |
| DFCI114 (G1269A) | | NSCL | 535 | 863 | 419 | 207 | 18 | 9 | 1615 |
| Kelly (F1174L) | Amplified | Neuroblastoma | 164 | 91 | 147 | 434 | 142 | 127 | 211 |

TABLE 5-continued

EC$_{50}$'s of the compounds of the present application against a panel of NSCLC and neuroblastoma cell lines transduced with ALK mutants

| Cell Line | MYCN | Histology | EC$_{50}$(nM) | | | | | | |
|---|---|---|---|---|---|---|---|---|---|
| | | | 31 | 32 | 6 | Alectinib | LDK378 | AP26113 | Crizotinib |
| LAN-1 (F1174L) | Amplified | Neuroblastoma | 494 | 265 | 571 | 2004 | 549 | 2853 | 1346 |
| SH-SY5Y (F1174L) | Non-Amplified | Neuroblastoma | 451 | 264 | 413 | 1150 | 186 | 986 | 523 |
| SK-N-SH (F1174L) | Non-Amplified | Neuroblastoma | 252 | 161 | 245 | 872 | 303 | 1988 | 370 |
| LAN-5 (R1275Q) | Amplified | Neuroblastoma | 152 | 83 | 192 | 617 | 122 | 790 | 232 |
| SMS-KCNR (R1275Q) | Amplified | Neuroblastoma | 129 | 74 | 133 | 765 | 92 | 535 | 179 |
| CHLA-20 (R1275Q) | Non-Amplified | Neuroblastoma | 119 | 92 | 218 | 430 | 363 | 8667 | 439 |
| SK-N-BE2 (wt) | Amplified | Neuroblastoma | 1149 | 752 | 623 | 1554 | 593 | 2928 | 710 |
| SK-N-FI (wt) | Non-Amplified | Neuroblastoma | 914 | 567 | 973 | 2401 | 349 | 2645 | 1469 |
| SK-N-AS (wt) | Non-Amplified | Neuroblastoma | 871 | 465 | 775 | 2139 | 1045 | 776 | 1473 |

TABLE 6

IC$_{50}$'s of Compound 6 against Ba/F3 or tumor cells transduced with various ALK mutants in comparison with clinical ALK inhibitors

| | | Crizotinib IC50 (µM) | Ceritinib IC50 (µM) | Afectinib IC50 (µM) | Compound 6 IC50 (µM) |
|---|---|---|---|---|---|
| Ba/F3 | EML4-ALK WT | 0.050 ± 0.016 | 0.026 ± 0.014 | 0.004 ± 0.003 | 0.004 ± 0.003 |
| | EML4-ALK G1202R | 0.315 ± 0.096 | 0.624 ± 0.159 | 0.235 ± 0.025 | 0.003 ± 0.002 |
| | EML4-ALK C1156Y | 0.184 ± 0.039 | 0.153 ± 0.022 | 0.008 ± 0.010 | 0.010 ± 0.012 |
| | EML4-ALK F1174L | 0.130 ± 0.045 | 0.095 ± 0.005 | 0.009 ± 0.012 | 0.011 ± 0.011 |
| | EML4-ALK L1196M | 0.482 ± 0.102 | 0.048 ± 0.015 | 0.132 ± 0.056 | 0.074 ± 0.049 |
| | EML4-ALK L1152R | 0.697 ± 0.062 | 2.364 ± 0.541 | 0.350 ± 0.069 | 0.195 ± 0.005 |
| | EML4-ALK 1151Tins | 0.724 ± 0.115 | 0.205 ± 0.052 | 0.062 ± 0.013 | 0.079 ± 0.030 |
| | EML4-ALK G1269A | 0.553 ± 0.035 | 0.035 ± 0.019 | 0.024 ± 0.014 | 0.015 ± 0.011 |
| | EML4-ALK S1206Y | 0.133 ± 0.059 | 0.029 ± 0.006 | 0.008 ± 0.010 | 0.010 ± 0.009 |
| | CD74-ROS | 0.017 ± 0.005 | | | 0.678 ± 0.109 |
| | del19EGFR | | | | 0.281 ± 0.001 |
| | Untransduced | 1.859 ± 0.059 | 6.064 ± 0.480 | >10 | 0.605 ± 0.013 |
| Tumor Cell Line | H3122 | 0.056 ± 0.021 | 0.013 ± 0.005 | 0.007 ± 0.004 | 0.004 ± 0.002 |
| | DFC176 (L1152R) | 0.248 ± 0.064 | 0.092 ± 0.031 | 0.026 ± 0.027 | 0.030 ± 0.034 |
| | DFCl114 (G1269A) | 1.697 ± 0.262 | 0.041 ± 0.029 | 0.194 ± 0.050 | 0.876 ± 0.131 |
| | PC9 | | | | 0.595 ± 0.011 |

Example 11: KINOMEscAN™ Analysis of the Compounds of the Present Application

Figure 3:
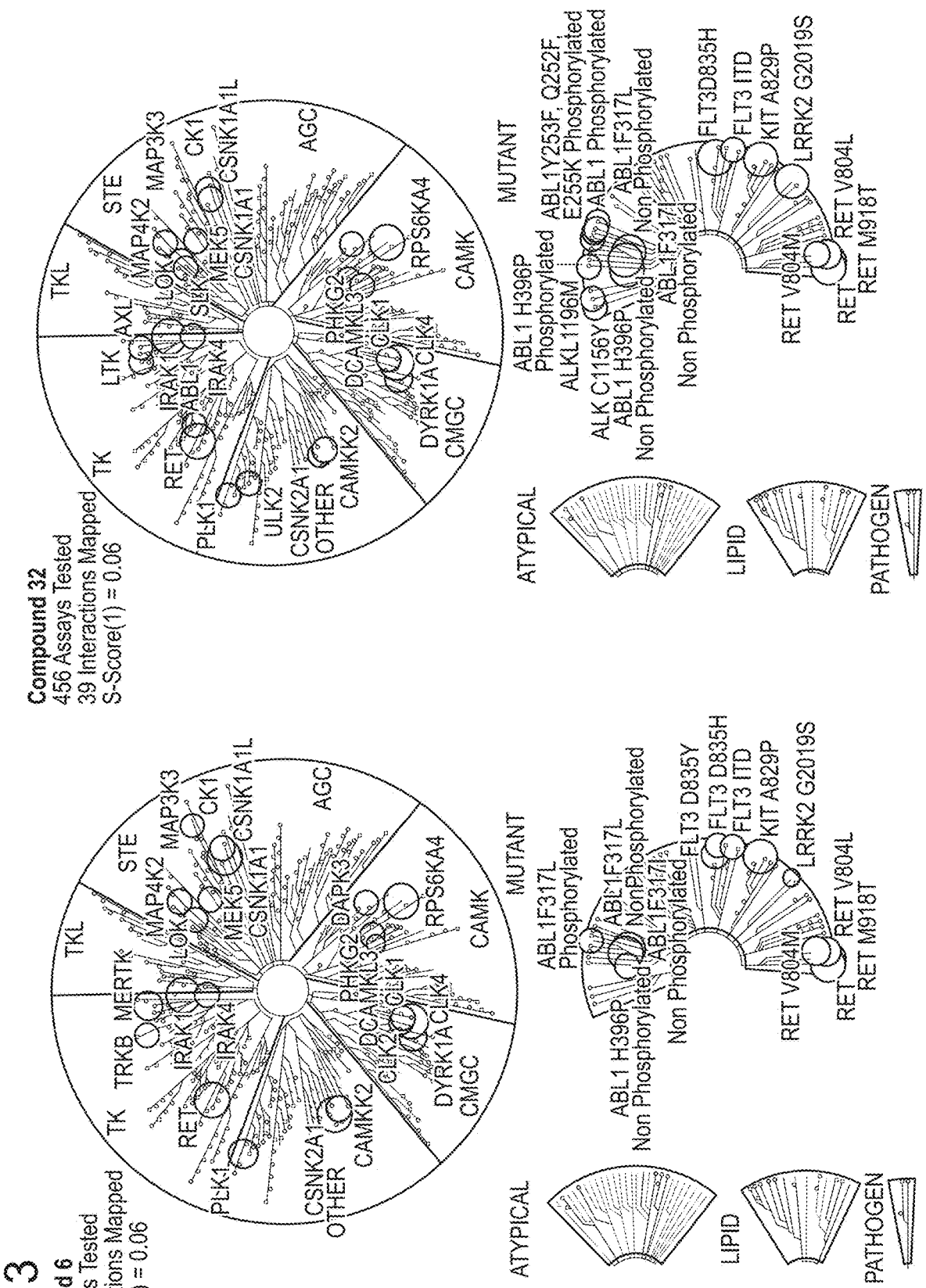
FIG. 3 shows the Ambit KINOMESCAN™ selectivity results for Compounds 6 and 32.

The kinase selectivity of the compounds of the present application was assessed using the KINOMEscAN™ methodology across a panel of 456 kinases (Ambit Biosciences, San Diego, Calif.). Compounds 6 and 32 were screened at a concentration of 1 µM. Both compounds were slightly less selective than Alectinib. Compound 6 was more selective than compound 32 with 34 interactions mapped compared to 39 with an S-score (1)=0.06, which may explain the increase in cytotoxicity against the neuroblastoma cell lines (FIG. 3). Dose—response analysis using Compound 6 revealed inhibition of CSNK2A1<10 µM, IRAK1 with an IC$_{50}$=14 nM, IRAK 4 with an IC$_{50}$=465 nM, CLK4 with an IC$_{50}$=14 nM, RET with an IC$_{50}$=3 nM, RET V804L with an IC$_{50}$=13 nM, and RET V804M with an IC$_{50}$=12 nM. Dose—response analysis using compound 32 revealed inhibition of CSNK2A1<10 µM, IRAK1 with an IC$_{50}$=15 nM, IRAK 4 with an IC$_{50}$=234 nM, CLK4 with an IC$_{50}$=4 nM, RET with an IC$_{50}$=2 nM, RET V804L with an IC$_{50}$=9 nM, and RET V804M with an IC$_{50}$=23 nM.

Example 12: Pharmacokinetics and CNS Bioavailability of the Compounds of the Present Application The mouse pharmacokinetic profile of Compound 6 demonstrated good oral bioavailability (87% F), a half-life of 1.69 hours, and a plasma exposure of 64,635 (min*ng/mL, AUClast), following an oral dose of 10 mg/kg (Table 7). Additionally, 2 hours after an oral dose of 10 mg/kg, Compound 6 showed a plasma exposure of 0.34 µM, and a brain exposure of 0.03 µM which equates to a brain/plasma concentration ratio of 0.1. Compared to Compound 6, Compound 32 showed lower oral bioavailability (26% F), a half-life of 4.7 hours, and a plasma exposure of 109,909 (min*ng/mL, AUClast), following an oral dose of 10 mg/kg (Table 8). Additionally, 2 hours after an oral dose of 10 mg/kg, Compound 32 showed a plasma exposure of 0.21 µM, and a brain exposure of 0.03 µM which equates to a brain/plasma concentration ratio of 0.14.

TABLE 7

Pharmacokinetic properties of Compounds 6 and 32

| | matrix | route | Dose (mg/kg) | $T_{1/2}$ (hr) | $T_{max}$ (hr) | $C_{max}$ (ng/mL) | $C_{max}$ (μM) | $AUC_{last}$ (min*ng/mL) | $AUC_{last}$ (μM•hr) | $AUC_{INF\_obs}$ (min*ng/mL) | AUC (% extrap) | $Cl_{obs}$ (mL/min/kg) | $Vss_{obs}$ (L/kg) | % F |
|---|---|---|---|---|---|---|---|---|---|---|---|---|---|---|
| 6 | plasma | i.v. | 2 | 1.64 | 0.08 | 35250 | 75.71 | 769853 | 27.56 | 780621 | 1.74 | 3.55 | 0.38 | — |
|   |        | p.o. | 10 | 1.69 | 0.83 | 373 | 0.8 | 64635 | 2.31 | 67036 | 3.66 | 154.83 | — | 87 |
| 32 | plasma | i.v. | 2 | 3.06 | 0.08 | 1005 | 2.16 | 85807 | 3.07 | 96619 | 12.68 | 23.27 | 4.98 | — |
|    |        | p.o. | 10 | 4.79 | 0.92 | 640 | 1.38 | 109909 | 3.94 | 154859 | 29.71 | 67.98 | — | 26 |

TABLE 8

In Vivo CNS Availability of Compounds 6 and 32

| Cmpd | matrix | route | Dose (mg/kg) | Time (hr) | Conc. (ng/mL) | Conc. (μM) |
|---|---|---|---|---|---|---|
|   |        | i.v. | 2  | 2 | 960 | 2.06 |
| 6 | plasma | p.o. | 10 |   | 159 | 0.34 |
|   |        | i.v. | 2  | 8 | 76  | 0.16 |
|   |        | p.o. | 10 |   | 16  | 0.04 |
|   |        | i.v. | 2  | 2 | 19  | 0.04 |
| 6 | brain  | p.o. | 10 |   | 12  | 0.03 |
|   |        | i.v. | 2  | 8 | 2   | 0.004 |
|   |        | p.o. | 10 |   | 2   | 0.004 |
|   |        | i.v. | 2  | 2 | 100 | 0.21 |
| 32 | plasma | p.o. | 10 |   | 96  | 0.21 |
|   |        | i.v. | 2  |   | 22  | 0.05 |
|   |        | p.o. | 10 | 8 | 77  | 0.17 |
|   |        | i.v. | 2  | 2 | 53.8 | 0.12 |
| 32 | brain  | p.o. | 10 |   | 12.1 | 0.03 |
|   |        | i.v. | 2  |   | 35.4 | 0.08 |
|   |        | p.o. | 10 | 8 | 28.1 | 0.06 |

Example 13: Molecular Modeling

Figure 1B:
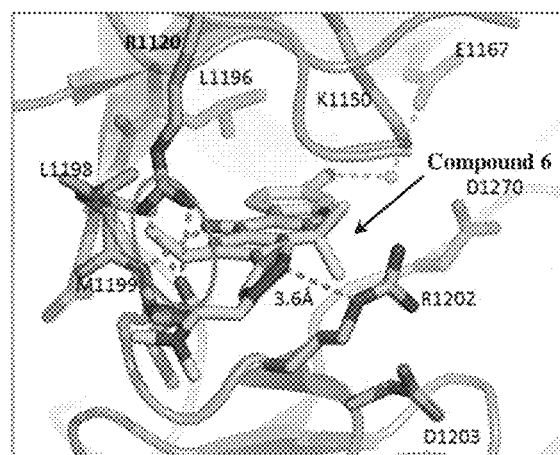

Molecular modeling study based upon the co-crystal structure of ALK with Alectinib (PDB: 3AOX) (Sakamoto, H. et al., Cancer Cell 2011, 19, 679) was performed to assess the structure-activity relationship of inhibition of ALK and/or ALK mutants by the compounds of the present application. The modeling showed that Compound 6 makes the same backbone hinge contact as Alectinib, however, Compound 6 forms two additional hydrogen bond interactions between the guanidine moiety of R1120 and the carbonyl group of the dimethyl acetamide group (FIG. 1A). Furthermore, in the G1202R mutant, Compound 6 forms an additional hydrogen bond interaction between the guanidine moiety of R1202 and the nitrogen of the pyrazole ring (FIG. 1B). The modeling study predicted that the methylene spacer between the pyrazole ring and the dimethylacetamide moiety is preferable for the carbonyl amide of Compound 6 to interact with the guanidine moiety of R1120.

Example 14: SRPK1 Inhibitory Activities of the Compounds of the Present Application, Measured as $IC_{50}$ (nM), are Shown in Table 9

TABLE 9

| Cmpd. | SRPK1 ($IC_{50}$ (nM)) | SRPK2 ($IC_{50}$ (nM)) |
|---|---|---|
| Alectinib | 11 | 28.2 |
| 7  | 3.01  | 12.4 |
| 9  | 1.15  | N/A |
| 10 | 5.09  | 14.5 |
| 13 | 0.884 | 7.46 |
| 14 | 2.61  | 13.2 |
| 16 | 2.53  | 12.5 |
| 17 | >$10^3$ | N/A |
| 19 | 2.66  | 8.57 |
| 31 | 1.91  | 6.6 |
| 36 | 4.75  | 23.6 |
| 37 | 35.6  | N/A |
| 38 | 41    | N/A |

EQUIVALENTS

Those skilled in the art will recognize, or be able to ascertain, using no more than routine experimentation, numerous equivalents to the specific embodiments described specifically herein. Such equivalents are intended to be encompassed in the scope of the following claims.

The invention claimed is:

1. A compound selected from the group consisting of:

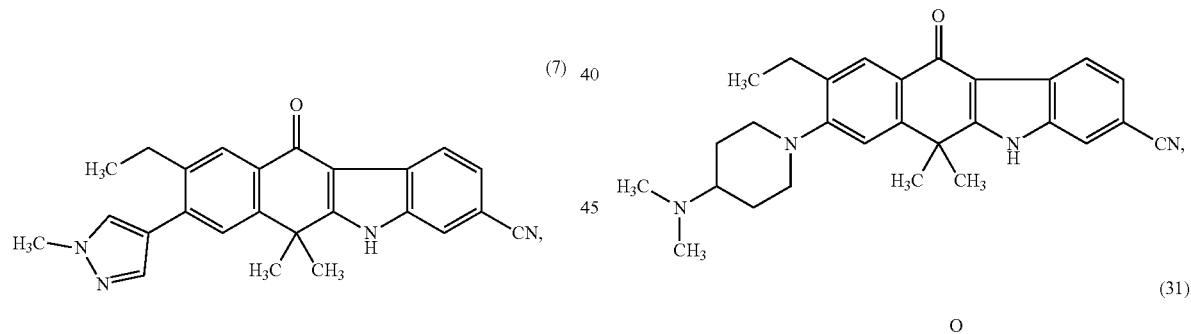

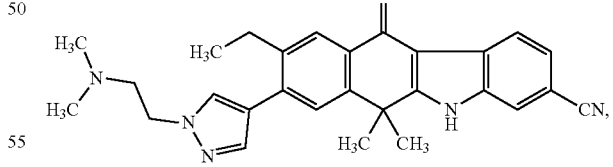

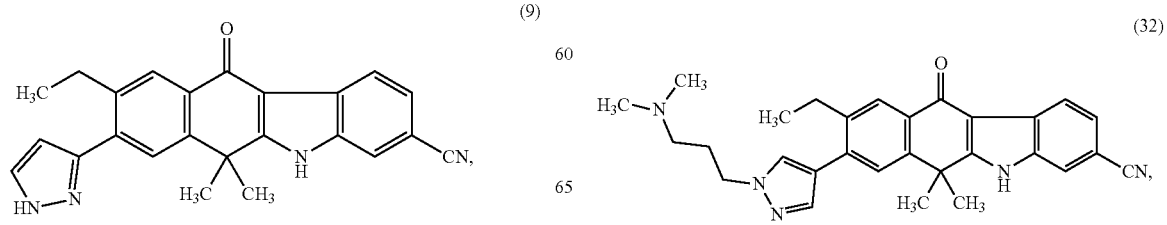

85
-continued

(33)
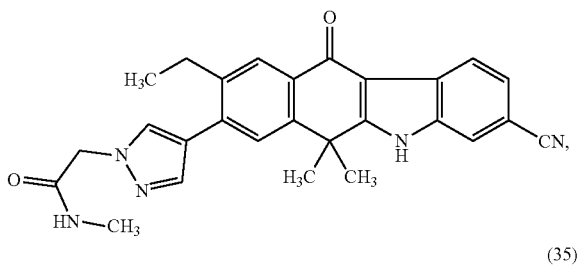

(35)
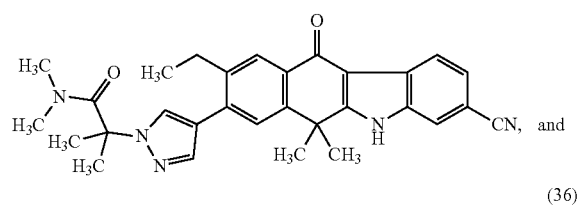
and

(36)
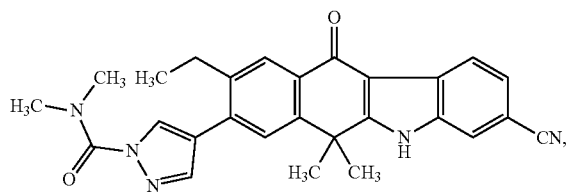

or a pharmaceutically acceptable salt or tautomer thereof.

2. A pharmaceutical composition comprising a pharmaceutically acceptable carrier and a therapeutically effective amount of the compound of claim 1, or a pharmaceutically acceptable salt or tautomer thereof.

3. A method for inhibiting anaplastic lymphoma kinase activity in a subject, wherein the method comprises administering to the subject in need thereof a therapeutically effective amount of the compound of claim 1, or a pharmaceutically acceptable salt or tautomer thereof.

4. The method of claim 3, wherein the subject has cancer.

5. The method of claim 4, wherein the cancer is neuroblastoma or non-small cell lung cancer.

6. A method for inhibiting serine-rich protein kinase activity in a subject, wherein the method comprises administering to the subject in need thereof a therapeutically effective amount of the compound of claim 1, or a pharmaceutically acceptable salt or tautomer thereof.

7. The method of claim 6, wherein the serine-rich protein kinase is serine-rich protein kinase-1.

* * * * *

SEQUENCE LISTING

```
<160> NUMBER OF SEQ ID NOS: 1

<210> SEQ ID NO 1
<211> LENGTH: 655
<212> TYPE: PRT
<213> ORGANISM: Homo sapiens

<400> SEQUENCE: 1

Met Glu Arg Lys Val Leu Ala Leu Gln Ala Arg Lys Lys Arg Thr Lys
1               5                   10                  15

Ala Lys Lys Asp Lys Ala Gln Arg Lys Ser Glu Thr Gln His Arg Gly
            20                  25                  30
```

```
Ser Ala Pro His Ser Glu Ser Asp Leu Pro Glu Gln Glu Glu Ile
         35                  40                  45
Leu Gly Ser Asp Asp Glu Gln Glu Asp Pro Asn Asp Tyr Cys Lys
 50                  55                  60
Gly Gly Tyr His Leu Val Lys Ile Gly Asp Leu Phe Asn Gly Arg Tyr
 65                  70                  75                  80
His Val Ile Arg Lys Leu Gly Trp Gly His Phe Ser Thr Val Trp Leu
                 85                  90                  95
Ser Trp Asp Ile Gln Gly Lys Lys Phe Val Ala Met Lys Val Val Lys
             100                 105                 110
Ser Ala Glu His Tyr Thr Glu Thr Ala Leu Asp Glu Ile Arg Leu Leu
             115                 120                 125
Lys Ser Val Arg Asn Ser Asp Pro Asn Asp Pro Asn Arg Glu Met Val
130                 135                 140
Val Gln Leu Leu Asp Asp Phe Lys Ile Ser Gly Val Asn Gly Thr His
145                 150                 155                 160
Ile Cys Met Val Phe Glu Val Leu Gly His His Leu Leu Lys Trp Ile
                 165                 170                 175
Ile Lys Ser Asn Tyr Gln Gly Leu Pro Leu Pro Cys Val Lys Lys Ile
             180                 185                 190
Ile Gln Gln Val Leu Gln Gly Leu Asp Tyr Leu His Thr Lys Cys Arg
             195                 200                 205
Ile Ile His Thr Asp Ile Lys Pro Glu Asn Ile Leu Leu Ser Val Asn
         210                 215                 220
Glu Gln Tyr Ile Arg Arg Leu Ala Ala Glu Ala Thr Glu Trp Gln Arg
225                 230                 235                 240
Ser Gly Ala Pro Pro Pro Ser Gly Ser Ala Val Ser Thr Ala Pro Gln
                 245                 250                 255
Pro Lys Pro Ala Asp Lys Met Ser Lys Asn Lys Lys Lys Lys Leu Lys
             260                 265                 270
Lys Lys Gln Lys Arg Gln Ala Glu Leu Leu Glu Lys Arg Met Gln Glu
             275                 280                 285
Ile Glu Glu Met Glu Lys Glu Ser Gly Pro Gly Gln Lys Arg Pro Asn
         290                 295                 300
Lys Gln Glu Glu Ser Glu Ser Pro Val Glu Arg Pro Leu Lys Glu Asn
305                 310                 315                 320
Pro Pro Asn Lys Met Thr Gln Glu Lys Leu Glu Glu Ser Ser Thr Ile
                 325                 330                 335
Gly Gln Asp Gln Thr Leu Met Glu Arg Asp Thr Glu Gly Gly Ala Ala
             340                 345                 350
Glu Ile Asn Cys Asn Gly Val Ile Glu Val Ile Asn Tyr Thr Gln Asn
             355                 360                 365
Ser Asn Asn Glu Thr Leu Arg His Lys Glu Asp Leu His Asn Ala Asn
370                 375                 380
Asp Cys Asp Val Gln Asn Leu Asn Gln Glu Ser Ser Phe Leu Ser Ser
385                 390                 395                 400
Gln Asn Gly Asp Ser Ser Thr Ser Gln Glu Thr Asp Ser Cys Thr Pro
                 405                 410                 415
Ile Thr Ser Glu Val Ser Asp Thr Met Val Cys Gln Ser Ser Ser Thr
             420                 425                 430
Val Gly Gln Ser Phe Ser Glu Gln His Ile Ser Gln Leu Gln Glu Ser
             435                 440                 445
Ile Arg Ala Glu Ile Pro Cys Glu Asp Glu Gln Glu Gln Glu His Asn
```

|     | 450 |     |     |     | 455 |     |     |     | 460 |     |     |
|-----|-----|-----|-----|-----|-----|-----|-----|-----|-----|-----|-----|
| Gly | Pro | Leu | Asp | Asn | Lys | Gly | Lys | Ser | Thr | Ala | Gly | Asn | Phe | Leu | Val |
| 465 |     |     |     |     | 470 |     |     |     | 475 |     |     |     |     |     | 480 |
| Asn | Pro | Leu | Glu | Pro | Lys | Asn | Ala | Glu | Lys | Leu | Lys | Val | Lys | Ile | Ala |
|     |     |     |     | 485 |     |     |     |     | 490 |     |     |     |     | 495 |     |
| Asp | Leu | Gly | Asn | Ala | Cys | Trp | Val | His | Lys | His | Phe | Thr | Glu | Asp | Ile |
|     |     |     | 500 |     |     |     |     | 505 |     |     |     |     | 510 |     |     |
| Gln | Thr | Arg | Gln | Tyr | Arg | Ser | Leu | Glu | Val | Leu | Ile | Gly | Ser | Gly | Tyr |
|     |     | 515 |     |     |     |     | 520 |     |     |     |     |     | 525 |     |     |
| Asn | Thr | Pro | Ala | Asp | Ile | Trp | Ser | Thr | Ala | Cys | Met | Ala | Phe | Glu | Leu |
|     | 530 |     |     |     |     | 535 |     |     |     |     | 540 |     |     |     |     |
| Ala | Thr | Gly | Asp | Tyr | Leu | Phe | Glu | Pro | His | Ser | Gly | Glu | Glu | Tyr | Thr |
| 545 |     |     |     |     | 550 |     |     |     |     | 555 |     |     |     |     | 560 |
| Arg | Asp | Glu | Asp | His | Ile | Ala | Leu | Ile | Ile | Glu | Leu | Leu | Gly | Lys | Val |
|     |     |     |     | 565 |     |     |     |     | 570 |     |     |     |     | 575 |     |
| Pro | Arg | Lys | Leu | Ile | Val | Ala | Gly | Lys | Tyr | Ser | Lys | Glu | Phe | Phe | Thr |
|     |     |     | 580 |     |     |     |     | 585 |     |     |     |     | 590 |     |     |
| Lys | Lys | Gly | Asp | Leu | Lys | His | Ile | Thr | Lys | Leu | Lys | Pro | Trp | Gly | Leu |
|     |     | 595 |     |     |     |     | 600 |     |     |     |     | 605 |     |     |     |
| Phe | Glu | Val | Leu | Val | Glu | Lys | Tyr | Glu | Trp | Ser | Gln | Glu | Glu | Ala | Ala |
|     | 610 |     |     |     |     | 615 |     |     |     |     | 620 |     |     |     |     |
| Gly | Phe | Thr | Asp | Phe | Leu | Leu | Pro | Met | Leu | Glu | Leu | Ile | Pro | Glu | Lys |
| 625 |     |     |     |     | 630 |     |     |     |     | 635 |     |     |     |     | 640 |
| Arg | Ala | Thr | Ala | Ala | Glu | Cys | Leu | Arg | His | Pro | Trp | Leu | Asn | Ser |     |
|     |     |     |     | 645 |     |     |     |     | 650 |     |     |     |     | 655 |     |